US007332575B2

(12) United States Patent
Lee et al.

(10) Patent No.: US 7,332,575 B2
(45) Date of Patent: Feb. 19, 2008

(54) GROWTH DIFFERENTIATION FACTOR-8 NUCLEIC ACID AND POLYPEPTIDE FROM AQUATIC SPECIES, AND TRANSGENIC AQUATIC SPECIES

(75) Inventors: Se-Jin Lee, Baltimore, MD (US); Alexandra C. McPherron, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 29 days.

(21) Appl. No.: 10/991,343

(22) Filed: Nov. 15, 2004

(65) Prior Publication Data

US 2005/0216962 A1   Sep. 29, 2005

Related U.S. Application Data

(63) Continuation of application No. 09/640,887, filed on Aug. 17, 2000, now abandoned, which is a continuation-in-part of application No. 09/378,238, filed on Aug. 19, 1999, now Pat. No. 6,465,239, which is a continuation-in-part of application No. 08/795,071, filed on Feb. 5, 1997, now Pat. No. 5,994,618, which is a continuation-in-part of application No. 08/525,596, filed as application No. PCT/US94/03019 on Mar. 18, 1994, now Pat. No. 5,827,733.

(51) Int. Cl.
*C07K 14/00* (2006.01)
*A61K 38/16* (2006.01)

(52) U.S. Cl. .................. 530/350; 424/198.1; 435/69.1
(58) Field of Classification Search ............... None
See application file for complete search history.

(56) References Cited

U.S. PATENT DOCUMENTS

| 5,585,479 A | 12/1996 | Hoke et al. |
| 5,616,561 A | 4/1997 | Barcellos-Hoff |
| 5,639,638 A | 6/1997 | Wozney et al. |
| 5,814,491 A | 9/1998 | Vijg et al. |
| 5,827,733 A | 10/1998 | Lee et al. |
| 6,103,466 A | 8/2000 | Grobet et al. |

FOREIGN PATENT DOCUMENTS

| WO | WO 91/08291 | 6/1991 |
| WO | WO 94/21681 | 9/1994 |
| WO | WO 96/01845 | 1/1996 |
| WO | WO 98/33887 | 8/1998 |
| WO | WO 99/92667 A1 | 1/1999 |
| WO | WO 99/40181 A1 | 8/1999 |
| WO | WO 99/42573 A1 | 8/1999 |

OTHER PUBLICATIONS

Harrison et al., J. Biol. Chem., 2004, 279(27):28036-44.*
Bradley et al., "Modifying The Mouse: Design and Desire," Biotechnology 10:534-539 (1992).
Bowie et al., Science, 1990, 247:1307-1310.
Callard et al., The Cytokine FactBook, Academic Press, London, p. 31-32 (1994).
Constam & Robertson, "Regulation of Bone Morphogenetic Protein Activity by Pro Domains and Proprotein Convertases," J. Cell. Biol., vol. 144, No. 1, Jan. 1999, pp. 139-149.
Deli et al., "Biochemical Study of Muscle Samples from Chicken Embryos Affected by Wofatox 50 EC," Archives of Toxicology 8:277-279 (1985).
Dickman, "Gene Mutation Provides More Meat on the Hoof," Science 277:1922-1923 (1997).
Ebert et al., "A Moloney MLV-Rat Somatotropin Fusion Gene Produces Biologically Active Somatotropin in a Transgenic Pig," Molecular Enocrinology, 2:277-283.
Evock et al., "Pituitary Procine Growth Hormone (pGH) and a Recombinant pGH Analog Stimulate Pig Growth Performance in a Similar Manner," Journal of Animal Science 66:1928-1941.
Faulkner et al., "Effect of Testosterone Propionate on Performance and Carcass Characteristics of Heifers and Cows," Jounral of Animal Science, 67:1907-1915.
Flakroll et al., "Influence of alpha-ketoisocaproate on lamb growth, feed conversion, and carcass composition," Journal of Animal Science, 69:1461-1467, Abstract only.
Grobet et al., "A deletion in the bovine myostatin gene causes the double-muscled phenotype in cattle," Journal of Animal Science 69:1461-1467, Abstract only.
Grobet et al., "Molecular definitiono f an allelic series of mutations disrupting the myostatin function and causing double-muscleing in cattle," Mammalian Genome, 9:210-213 (1998).
Gura, Trisha, "Antisense Has Growing Pains," Science 270:575-577 (1995).
Hammer et al., "Genetic Engineering of Mammalian Embryos," Journal of Animal Science, 63:269-278 (1986).
Kambadur et al., "Mutations in myostating (GDF8) in Double-Muscled Belgian Blue and Piedmontese Cattle," Genome Research, 7:910-915 (1997).
Kappel et al., "Regulating gene expression in transgenic animals," Current Opinion in Biotechnology, 3:548-553 (1992).
Love et al., "Transgenic Birds by DNA Microinjection," Bio/Technology 12(1):60-63 (1994).
Massague, Cell, 49:437-438 (1987).
McDowell et al., "Effects of Exogenous Growth Hormone on Milk Production and Nutrient Uptake by Muscle and Mammary Tissues of dairy Cows in Mid-lactation," Australian Journal of Biological Sciences, 40:295-306 (1987).
McPherron et al., "Double muscling in cattle due to mutations in the myostating gene," Proc. Natl. Acad. Sci., USA, 94:12457-12461 (1997).

(Continued)

*Primary Examiner*—Eileen B. O'Hara
*Assistant Examiner*—Xiaozhen Xie
(74) *Attorney, Agent, or Firm*—DLA Piper US LLP

(57) ABSTRACT

Purified GDF-8 polypeptides of aquatic organisms.

2 Claims, 37 Drawing Sheets

OTHER PUBLICATIONS

McPherron et al., "Regulation of skeletal muscle mass in mice by a new TGF-β superfamily member," Nature, 387:83-90 (1997).

Moreadith et al., "Gene targeting in embryonic stem cells: the new physiology and metabolism," J. Mol. Med. 75:208-216 (1997).

Mullins et al., "Perspectives Series: Molecular Medicine in Genetically Engineered Animals," Journal of Clinical Investigation 98(11):S37-S40 (1996).

Research Genetics (advertisement), "designer PCR," Nucleic Acids Research 22(15) (1994).

Seamark, R.F., "Progress and Emerging Problems in Livestock Transgenesis: a Summary Perspective," Reproduction, Fertility and Development 6:653-657 (1994).

Slack, J.M.W., "Growth control: Action mouse," Current Biology, 7:R467-R469 (1997).

Strojeck et al., "The Use of Transgenic Animal Techniques for Livestock Improvement," Genetic Engineering: Principles and Methods, 10:221-246 (1988).

Wall, R.J., "The Transgenic Livestock: Progerss and Prospects for the Future," Theriogenology, 45:57-58 (1996).

Westhusin, Mark, "From mighty mouse to mighty cows," Nature Genetics, 17:4-5 (1997).

Zhu et al., "Survey of Major Histocompatibility Complex Class II Haplotypes in Four Turkey Lines Using Restriction Fragment Length Polymorphism Analysis with Nonradioactive DNA Detection," Poultry Science, 74:1067-1073 (1995).

Prelle et al., Establishment of pluripotent cell lines from vertebrate species-present status and future prospects. Cell Tissues Organs 1999; vol. 165, pp. 220-236.

Gonzalez-Cadavid et al., "Organization of the human myostatin gene and expression in healthy men and HIV-infected men with muscle wasting," Proc Natl Acd Sci USA, Dec. 1998, 95(25):14938-14943.

Rudinger, Peptide Hormones, Parsons ed., University Park Press, Baltimore, pp. 1-7, 1976.

Wells, Biochemistry, 29:8507-17, 1990.

Ngo et al., "The Protein Folding Problem and Tertiary Structure Prediction," Merz et al.,, Birkhauser, Boston, pp. 491-495, 1994.

McPherron et al., GenBank Accession No. AF019626, Nov. 21, 1997.

* cited by examiner

HEART
LUNG
THYMUS
BRAIN
KIDNEY
SEMINAL VESICLE
PANCREAS
INTESTINE
SPLEEN
TESTIS
FAT
UTERUS
OVARY
LIVER
MUSCLE

```
  1 TTAAGGTAGGAAGGATTTCAGGCTCTATTTACATAATTGTTCTTTCCTTTTCACACAGAA  60
                                                              N
 61 TCCCTTTTTAGAAGTCAAGGTGACAGACACACCCAAGAGGTCCCGGAGAGACTTTGGGCT 120
      P  F  L  E  V  K  V  T  D  T  P  |K  R| S  |R  R| D  F  G  L
121 TGACTGCGATGAGCACTCCACGGAATCCCGGTGCTGCCGCTACCCCCTCACGGTCGATTT 180
     D  C  D  E  H  S  T  E  S  R  C  C  R  Y  P  L  T  V  D  F
181 TGAAGCCTTTGGATGGGACTGGATTATCGCACCCAAAAGATATAAGGCCAATTACTGCTC 240
     E  A  F  G  W  D  W  I  I  A  P  K  R  Y  K  A  N  Y  C  S
241 AGGAGAGTGTGAATTTGTGTTTTACAAAAATATCCGCATACTCATCTTGTGCACCAAGC  300
     G  E  C  E  F  V  F  L  Q  K  Y  P  H  T  H  L  V  H  Q  A
301 AAACCCCAGAGGCTCAGCAGGCCCTTGCTGCACTCCGACAAAAATGTCTCCCATTAATAT 360
     N  P  R  G  S  A  G  P  C  C  T  P  T  K  M  S  P  I  N  M
361 GCTATATTTTAATGGCAAAGAACAAATAATATATGGGAAAATTCCAGCCATGGTAGTAGA 420
     L  Y  F  N  G  K  E  Q  I  I  Y  G  K  I  P  A  M  V  V  D
421 CCGCTGTGGGTGCTCATGAGCTTTGCATTAGGTTAGAAACTTCCCAAGTCATGGAAGGTC 480
     R  C  G  C  S  *
481 TTCCCCTCAATTTCGAAACTGTGAATTCCTGCAGCCCGGGGGATCCACTAGTTCTAGAGC 540
541 GGCCGCCACC    550
```

FIG. 2A

```
  1 CAAAAAGATCCAGAAGGGATTTTGGTCTTGACTGTGATGAGCACTCAACAGAATCACGAT  60
    |K  R| S  |R  R| D  F  G  L  D  C  D  E  H  S  T  E  S  R  C
 61 GCTGTCGTTACCCTCTAACTGTGGATTTTGAAGCTTTTGGATGGGATTGGATTATCGCTC 120
     A  V  V  T  L  T  V  D  F  E  A  F  G  W  D  W  I  I  A  P
121 CTAAAAGATATAAGGCCAATTACTGCTCTGGAGAGTGTGAATTTGTATTTTACAAAAAT  180
     K  R  Y  K  A  N  Y  C  S  G  E  C  E  F  V  F  L  Q  K  Y
181 ATCCTCATACTCATCTGGTACACCAAGCAAACCCCAGAGGTTCAGCAGGCCCTTGCTGTA 240
     P  H  T  H  L  V  H  Q  A  N  P  R  G  S  A  G  P  C  C
241 CTCCCACAAAGATGTCTCCAATTAATATGCTATATTTTAATGGCAAAGAACAAATAATAT 300
     T  P  T  K  M  S  P  I  N  M  L  Y  F  N  G  K  E  Q  I  I  Y
301 ATGGGAAAATTCCAGCGATGGTAGTA  326
     G  K  I  P  A  M  V  V
```

FIG. 2B

GAA GAT GGG CTG AAT CCC TTT TTA GAA GTC AAA GTA ACA GAC ACA CCC AAG AGG TCC CGG
 E   D   G   L   N   P   F   L   E   V   K   V   T   D   T   P   K   R   S   R

AGA GAC TTT GGG CTT GAC TGT GAT GAA CAC TCC ACG GAA TCG CGG TGC TGT CGC TAC CCC
 R   D   F   G   L   D   C   D   E   H   S   T   E   S   R   C   C   R   Y   P

CTC ACG GTC GAT TTC GAA GCC TTT GGA TGG GAC TGG ATT ATT GCA CCC AAA AGA TAT AAG
 L   T   V   D   F   E   A   F   G   W   D   W   I   I   A   P   K   R   Y   K

GCT AAT TAC TGC TCT GGA GAG TGT GAA TTT GTG TTC TTA CAA AAA TAT CCG CAT ACT CAT
 A   N   Y   C   S   G   E   C   E   F   V   F   L   Q   K   Y   P   H   T   H

CTT GTG CAC CAA GCA AAC CCC AGA GGC TCG GCA GGC CCT TGC TGC ACG CCA ACA AAA ATG
 L   V   H   Q   A   N   P   R   G   S   A   G   P   C   C   T   P   T   K   M

TCT CCC ATT AAT ATG CTA TAT TTT AAT GGC AAA GAA CAA ATA ATA TAT GGG AAA ATT CCA
 S   P   I   N   M   L   Y   F   N   G   K   E   Q   I   I   Y   G   K   I   P

GCC ATG GTA GTA GAC CGG TGT GGG TGC.TCG TGA GCT TTG CAT TAG CTT TAA AAT TTC CCA
 A   M   V   V   D   R   C   G   C   S   *

AAT CGT GGA AGG TCT TCC CCT CGA TTT CGA AAC TGT GAA TTT ATG TAC CAC AGG CTG TAG

RAT GDF-8

FIG. 2C

```
TTA GTA AAG GCA CAA TTA TGG ATA TAC TTG AGG CAA GTC CAA AAA CCT ACA GTG
 L   V   K   A   Q   L   W   I   Y   L   R   Q   V   Q   K   P   T   V
TTT GTG CAG ATC CTG AGA CTC ATT AAG CCC ATG AGA GAC GGT ACA GGT TAT ATT
 F   V   Q   I   L   R   L   I   K   P   M   R   D   G   T   G   Y   I
GGA AAA TTG GAC TTT AAA ATG GAC CCA AAC CCA CAA GGC ACG ATT GAT GTG AAA
 G   K   L   D   F   K   M   D   P   N   P   Q   G   T   I   D   V   K
ACA GTG CAA CTG CTC TTG AAT ATG ACG CTC TCC AAA ATC CAG AGT ATT GAA ATA
 T   V   Q   L   L   L   N   M   T   L   S   K   I   Q   S   I   E   I
TTT GAT GAG ACT GGA CGA GAT CTT GCT ACA GTC CGT GAA ATC GGC GGT GAT TTT
 F   D   E   T   G   R   D   L   A   T   V   R   E   I   G   G   D   F
AAC CCA CCA TTA TTG AGA GTT CGA TCA ACG GAT ACG GAC AAA CAC CCG TCC CTA
 N   P   P   L   L   R   V   R   S   T   D   T   D   K   H   P   S   L
CTT GAC TGC GAG GAG CAC TGG TCC CGA TGT TGT AAA TAC CCG TAC CGC CGG GGA
 L   D   C   E   E   H   W   S   R   C   C   K   Y   P   Y   R   R   G
TTC GAA GCT TTC GGA TGG GAC TGG ATT ATA GCA CCT AAA AGA TAC CAC GCC AAA
 F   E   A   F   G   W   D   W   I   I   A   P   K   R   Y   H   A   K
TCC GGA GAA TGC GAA TTT GTG TTT CTA CAG CAA TAT CCG CAC ACC CAC ACG CTG
 S   G   E   C   E   F   V   F   L   Q   Q   Y   P   H   T   H   T   L
GCA AAT CCC CGA AGC AGG GGC TCA GAG GCA AAA GAA CAA GAA CCT CCT GAG ATG
 A   N   P   R   S   R   G   S   E   A   K   E   Q   E   P   P   E   M
ATG CTG TAT TTC AAT GGG GGC TGC TGA GGA AAA AAG CTA TAT GAA ATC ACG TAC GCT
 M   L   Y   F   N   G   G   C   *   G   K   K   L   Y   E   I   T   Y   A
GAT CGT TGC TGC TCA GGC TGT CGT TGA GGC ATA AAT GGA AGC
 D   R   C   C   S   G   C   R   *   G   I   N   G   S

AGG CAT TGC C
```

CHICKEN GDF-8

FIG. 2D zebrafish.nucleotide
[Strand]

```
1    ATGCATTTTA CACAGGTTTT AATTTCTCTA AGTGTATTAA TTGCATGTGG TCCAGTGGGT TATGGAGATA
      M  H  F  T   Q  V  L   I  S  L   S  V  L  I   A  C  G   P  V  G   Y  G  D

71   TAACGGGGCA CCAGCAGCCT CCACAGCCA CGGAGGAAAG CGAGCTGTGT TCCACATGTG AGTTCAGACA
      I  T  A  H   Q  Q  P   S  T  A   T  E  E  S   E  L  C   S  T  C   E  F  R  Q

141  ACACAGCAAG CTGATGAGAC TGCATGCCAT CAAGTCCCAA ATTCTTAGCA AACTCCGACT CAAGCAGGCT
      H  S  K   L  M  R  L   H  A  I   K  S  Q   I  L  S  K   L  R  L   K  Q  A

211  CCAAACATCA GCCGGGACGT GGTCAAGCAG CTGTTACCCA AAGCACCGCC TTTGCAACAA CTTCTGGATC
      P  N  I  S   R  D  V   V  K  Q   L  L  P  K   A  P  P   L  Q  Q   L  L  D

281  AGTACGATGT TTTAGGAGAT GACAGTAAGG ATGGAGCTGT GGAAGAGGAC GATGAACATG CCACCACAGA
      Q  Y  D  V   L  G  D   D  S  K  D   G  A  V   E  E  D   D  E  H  A   T  T  E

351  GACCATCATG ACCATGGCCA CAGAACCTGA CCCCATTGTT CAAGTAGATC GGAAACCGAA GTGTTGCTTT
      T  I  M   T  M  A  T   E  P  D   P  I  V   Q  V  D  R   K  P  K   C  C  F

421  TTCTCCTTCA GTCCGAAGAT CCAAGCAAAT CGGATCGTAA GAGCGCAGCT CTGGTTCAT CTGAGACCGG
      F  S  F  S   P  K  I   Q  A  N   R  I  V  R   A  Q  L   W  V  H   L  R  P

491  CGGAGGAGGC GACCACCGTC TTCTTACAGA TATCTCGGCT GATGCCCGTT AAGGACGGAG GAAGACACCG
      A  E  E  A   T  T  V   F  L  Q  I   S  R  L   M  P  V   K  D  G   G  R  H  R
```

FIG. 2E-1

```
561   AATACGATCC CTGAAAATCG ACGTGAACGC AGGAGTCACG TCTTGGCAGA GTATAGACGT AAAGCAGTG
       I  R  S   L  K  I  D   V  N  A   G  V  T   S  W  Q  S   I  D  V   K  Q  V
631   CTCACGGTGT GGTTAAAACA ACCGGAGACC AACCGAGGCA TCGAGATTAA CGCATATGAC GCGAAGGAA
       L  T  V  W  L  K  Q   P  E  T   N  R  G   I  E  I  N   A  Y  D   A  K  G
701   ACGACTTGGC CGTCACTTCA ACGGAGACTG GGGAGGATGG ACTGCTCCCC TTTATGGAGG TGAAAATATC
       N  D  L  A  V  T  S   T  E  T  G   E  D  G   L  L  P   F  M  E  V   K  I  S
771   AGAGGGCCCA AAACGAATCC GGAGGGACTC CGGACTGGAC TGCGATGAGA ATTCCCTAGA GTCTCGCTGC
       E  G  P   K  R  I  R   R  D  S   G  L  D   C  D  E  N   S  S  E   S  R  C
841   TGCAGGTACC CTCTCACTGT GGACTTCGAG GACTTTGGCT GGGACTGGAT TATTGCTCCA AAACGCTATA
       C  R  Y  P   L  T  V   D  F  E   D  F  G  W   D  W  I   I  A  P   K  R  Y
911   AGGCGAATTA CTGTTCAGGA GAATGCGACT ACATGTACCT GCAGAAGTAT CCCCACACCC ATCTGGTGAA
       K  A  N  Y   C  S  G   E  C  D  Y   M  Y  L   Q  K  Y   P  H  T  H   L  V  N
981   CAAGGCCAGT CCGAGAGGAA CGGCTGGGCC CTGCTGCACT CCCACCAAGA TGTCTCCCAT CAACATGCTT
       K  A  S   P  R  G  T   A  G  P   C  C  T   P  T  K  M   S  P  I  N   M  L
1051  TACTTTAACG GCAAAGAGCA GATCATCTAC GGCAAAGATCC CTTCGATGGT AGTAGACCGC TGTGGCTGCT
       Y  F  N  G   K  E  Q   I  I  Y   G  K  I  P   S  M  V   V  D  R   C  G  C
1121  CATGA
       S
```

FIG. 2E-2 salmon GDF-8.nucleotide1
[Strand]

```
1    GGCAGCCGGA GACGAATTGG GGGATCGAGA TTAATGCGTT CGACTCGAAG GGAAATGATC TGGCCGTTAC
      Q  P  E   T  N  W   G  I  E  I   N  A  F   D  S  K    G  N  D  L   A  V  T

71   CTCAGCAGAA GCGGGAGAAG GACTGCAACC CTTCATGGAG GTGACGATTT CAGAGGGCCC GAAGGCCTCC
      S  A  E   A  G  E  G   L  Q  P   F  M  E   V  T  I   S  E  G  P   K  R  S

141  AGGAGAGACT CGGGCCCTGA CTGTGACGAG AACTCCCCCG AGTCCCGCTG TTGCCGCTAC CCCCTCACGG
      R  R  D  S   G  L  D   C  D  E   N  S  P   E  S  R  C   R  Y   P  L  T

211  TAGACTTTGA AGACTTTGGC TGGGACTGGA TTATTGCCCC CAAGCGCTAC AAGGCCAACT ACTGCTCTGG
      V  D  F  E   D  F  G   W  D  W   I  I  A  P   K  R  Y   K  A  N  Y   C  S  G

281  TGAGTGTGAG TACATGCACC TGCAGAAGTA CCCCCACAAG ATGTCCCCA TCAACATGCT CTACTTCAAC CGCAAAGAGC
      E  C  E   Y  M  H  L   Q  K  Y   P  H  T   H  L  V  N   K  A  N   P  R  G

351  ACCGCAGGGC CCTGCTGCAC CCCCACCAAG ATGTCCCCA TCAACATGCT CTACTTCAAC CGCAAAGAGC
      T  A  G  P   C  C  T   P  T  K   M  S  P   I  N  M  L   Y  F  N   R  K  E

421  AGATCATCTA CGGCAAGATC CCCTCCATG TGGTGGACCG TTGCGGATGC TCGTGA
      Q  I  I  Y   G  K  I   P  S  M  V   V  D  R   C  G  C   S
```

FIG. 2F salmon GDF8.nucleotide2
[Strand]

```
1    GGTTACCTCA ACTGAAGCCG GAGAAGGACT GCAACCCTTC ATGGAGGTGA AGATTTCGGA GGGCCCGAAG
      V  T  S   T  E  A  G   E  G  L    Q  P  F   M  E  V  K   I  S  E   G  P  K

71   CGCTCCAGGA GAGATTCGGG CCTGGACTGT GATGAGAACT CCCCCGAGTC CCGCTGCTGC CGGTACCCCC
      R  S  R  R   D  S  G   L  D  C   D  E  N  S   P  E  S   R  C  C   R  Y  P

141  TCACGGGTGA CTTTGAAGAC TTTGGCTGGG ACTGGATTAT TGCCCCCAAG CGGTACAAGG CCAACTACTG
      L  T  V  D   F  E  D   F  G  W  D   W  I  I   A  P  K   R  Y  K  A   N  Y  C

211  CTCTGGTGAG TGCGAGTACA TGCACCTGCA GAAGTACCCC CACACCCACC TGGTGAACAA GGCTAACCCT
      S  G  E   C  E  Y  M   H  L  Q   K  Y  P   H  T  H  L   V  N  K   A  N  P

281  CGCGGGCACCG CGGGGCCCTG CTGCACCACC ACCAGAGATGT CCCCCATCAA CATGCTCTAC TTCAACCGCA
      R  G  T  A   G  P  C   C  T  P   T  K  M  S   P  I  N   M  L  Y   F  N  R

351  AAGAGCAGAT CATCTACGGC AAGATCCCCT CCATGGTGGT GGACCGCTGC GGCTGCTCGT GA
      K  E  Q  I   I  Y  G   K  I  P  S   M  V  V   D  R  C   G  C  S
```

FIG. 2G

```
GDF-8         SRRDFGLDCDEHSTESRCCRYPLTVDF-EAFGWD-WIIAPKRYKANYCSGECEFVFLQKYP------------
GDF-1         RPRRDAEPVLGGGPGGACRARRLYVSF-REVGWHRWVIAPRGFLANYCQGQCALPVALSGSGGPP
BMP-2         REKRQAKHKQRKRLKSSCKRHPLYVDF-SDVGWNDWIVAPPGYHAFYCHGECPFPLADHLNS-----
BMP-4         KRSPKHHSQRARKKNKNCRRHSLYVDF-SDVGWNDWIVAPPGYQAFYCHGDCPFPLADHLNS-----
Vgr-1         SRGSGSSDYNGSELKTACKKHELYVSF-QDLGWQDWIIAPKGYAANYCDGECSFPLNAHMNA-----
CP-1          LRMANVAENSSSDQRQACKKHELYVSF-RDLGWQDWIIAPEGYAAYYCEGECAFPLNSYMNA-----
BMP-5         SRMSSVGDYNTSEQKQACKKHELYVSF-RDLGWQDWIIAPEGYAAFYCDGECSFPLNAHMNA-----
BMP-3         EQTLKKARRKQWIEPRNCARRYLKVDF-ADIGWSEWIISPKSFDAYYCSGACQFPMPKSLKPS----
MIS           GPGRAQRSAGATAADGPCALRELSVDL--------RAERSVLIPETYQANNCQGVCGWPQSDRNPRY
Inhibinα      ALRLLQRPPEEPAAHANCHRVALNISF-QELGWERWIVYPPSFIFHYCHGQCGLHIPPNLSLPV--
Inhibinβa     HRRRRGLECDGKV-NICCKKQFFVSF-KDIGWNDWIIAPSGYHANYCEGECPSHIAGISGSSL---
InhibinβB     HRIRKRGLECDGRT-NLCCRQQFFIDF-RLIGWNDWIIAPTGYYGNYCEGSCPAYLAGVPGSAS---
TGF-β1        HRRALDTNYCFSSTEKNCCVRQLYIDFRKDLGWK-WIHEPKGYHANFCLGPCPYIWSLD--------
TGF-β2        KKRALDAAYCFRNVQDNCCLRPLYIDFKRDLGWK-WIHEPKGYNANFCAGACPYLWSSD--------
TGF-β3        KKRALDTNYCFRNLEENCCVRPLYIDFRQDLGWK-WVHEPKGYYANFCSGPCPYLRSAD--------

GDF-8         -HTHLVHQANPRG------------SAGPCCT--PTKMSPINMLYF-NGKEQIIYGKIPAMVVDRCGCS
GDF-1         ALNHAVLRALMHA--AAPGAADLPCCV--PARLSPISVLFF-DNSDNVVLRQYEDMVVDECGCR
BMP-2         -TNHAIVQTLVNS------VNSKIPKACCV--PTELSAISMLYL-DENEKVVLKNYQDMVVEGCGCR
BMP-4         -TNHAIVQTLVNS------VNSSIPKACCV--PTELSAISMLYL-DEYDKVVLKNYQEMVVEGCGCR
Vgr-1         -TNHAIVQTLVHL------MNPEYVPKPCCA-PTKLNAISVLYF-DDNSNVILKKYRNMVVRACGCH
OP-1          -TNHAIVQTLVHF------INPETVPKPCCA-PTQLNAISVLYF-DDSSNVILKKYRNMVVRAGCH
BMP-5         -TNHAIVQTLVHL------MFPDHVPKPCCA-PTKLNAISVLYF-DDSSNVILKKYRNMVVRSCGCH
BMP-3         --NHATIQSIVRA-VGVVPGIPEPCCV-----PEKMSSLSILFF-DENKNVVLKVYPNMTVESCACR
MIS           -GNHVVLLKMQA--RGAALARPPCCV------PTAYAGKLLISLSEER----ISAHHVPNMVATECGCR
Inhibinα      -PGAPPTPAQPYS--------LLPGAQPCCAALPGTMRPLHVRTTSDGGYSFKYETVPNLLTCHCACI
Inhibinβa     -SFHSTVINHYRMRGHSPFANLKSCCV----PTKLRPMSMLYY-DDGQNIIKKDIQNMIVEECGCS
InhibinβB     -SFHTAVVNQYRMRGLNPGT-VNSCCI----PTKLSTMSMLYF-DDEYNIVKRDVPNMIVEECGCA
TGF-β1        -TQYSKVLALYNQ--HNPGASAAPCCV----PQALEPLPIVYY-VGRKPKV-EQLSNMIVRSCKCS
TGF-β2        -TQHSRVLSLYNT----INPEASASPCCV---SQDLEPLTILYY-IGKTPKI-EQLSNMIVKSCKCS
TGF-β3        -TTHSTVLGLYNT----LNPEASASPCCV---PQDLEPLTILYY-VGRTPKV-EQLSNMVVKSCKCS
```

FIG. 3A

```
human    1   MQKLQLCVYIYLFMLIVAGPVDLNENSEQKENVEKEGLCNACTWRQNTKSRIEAIKIQILSKLRLETAPNISKDVIRQ    80
murine       MMQKLQMVYIYLFMLIAAGPVDLNEGSEKEENVEKEGLCNACAWRQNTRYSRIEAIKIQILSKLRLETAPNISKDAIRQ
rat
chicken human    81  LLPKAPPLRELIDQYDVQRDDSSDGSLEDDDYHATTETIITMPTESDFLMQVDGKPKCCFFKFSSKIQNKVVKAQLWIY   160
murine       LLPRAPPLRELIDQYDVQRDDSSDGSLEDDDYHATTETIITMPTESDFLMQADGKPKCCFFKFSSKIQNKVVKAQLWIY
rat
chicken                                                                              LVVKAQLWIY human   161  LRPVETPTTVFVQILRLIKPMKDGTRYTGIRSLKLDMNPGTGIWQSIDVKTVLQNWLKQPESNLGIEIKALDENGHDLAV  240
murine       LRPVKTPTTVFVQILRLIKPMKDGTRYTGIRSLKLDMNPGTGIWQSIDVKTVLQNWLKQPESNLGIEIKALDENGHDLAV
rat          LRQVQKPTTVFVQILRLIKPMKDGTRYTGI
chicken                                   GSLKLDMNPGTGIWQSIDVKTVLQNWLKQPESNLGIEIKAFDETGRDLAV human   241  TFPGPGEDGLNPFLEVKVTDTPKRSRRDFGLDCDEHSTESRCCRTPLTVDFEAFGWDWIIAPKRYKANYCSGECEFVFLQ  320
murine       TFPGPGEDGLNPFLEVKVTDTPKRSRRDFGLDCDEHSTESRCCRYPLTVDFEAFGWDWIIAPKRYKANYCSGECEFVFLQ
rat          EDGLNPFLEVKVTDTPKRSRRDFGLDCDEHSTESRCCRYPLTVDFEAFGWDWIIAPKRYKANYCSGECEFVFLQ
chicken      TFPGPGEDGLNPFLEVRVTDTPKRSRRDFGLDCDEHSTESRCCRYPLTVDFEAFGWDWIIAPKRYKANYCSGECEFVFLQ human   321  KYPHTHLVHQANPRGSAGPCCTPTKMSPINMLYFNGKEQIIYGKIPAMVVDRCGCS                            376
murine       KYPHTHLVHQANPRGSAGPCCTPTKMSPINMLYFNGKEQIIYGKIPAMVVDRCGCS
rat          KYPHTHLVHQANPRGSAGPCCTPTKMSPINMLYFNGKEQIIYGKIPAMVVDRCGCS
chicken      KYPHTHLVHQANPRGSAGPCCTPTKMSPINMLYFNGKEQIIYGKIPAMVVDRCGCS
```

```
  1 M M Q K L Q M Y - - - V Y I Y L F M L I A A G P V D L N E G S E R   murine
  1 M H F T Q - - - - V L I H S L L S V L I A C G P V G Y G D I T A H   zebrafish
  1 - - - - - - - - - - - - - - - - - - - - - - - - - - - - - - - -   salmon1
  1 - - - - - - - - - - - - - - - - - - - - - - - - - - - - - - - -   salmon2
              10                  20                  30

31 E E - - N V E K E G L C N A C A W R Q N T R Y S R I E A I         murine
 28 Q Q P S T A T E E S E L C S T C E F R Q H S K L M R L H A I       zebrafish
  1 - - - - - - - - - - - - - - - - - - - - - - - - - - - -           salmon1
  1 - - - - - - - - - - - - - - - - - - - - - - - - - - - -           salmon2
              40                  50                  60

58 K I Q I L S K L R L E T A P N I S K D A I R Q L L P R A P P       murine
 58 K S Q I L S K L R L K Q A P N I S R D V V K Q L L P K A P P       zebrafish
  1 - - - - - - - - - - - - - - - - - - - - - - - - - - - - -         salmon1
  1 - - - - - - - - - - - - - - - - - - - - - - - - - - - - -         salmon2
              70                  80                  90

88 L R E L I D Q Y D V Q R D D S S D G S L E D D D Y H A T T E       murine
 88 L L Q Q L L D Q Y D V L G D D S K D G A V E E D D E H A T T E     zebrafish
  1 - - - - - - - - - - - - - - - - - - - - - - - - - - - - -         salmon1
  1 - - - - - - - - - - - - - - - - - - - - - - - - - - - - -         salmon2
             100                 110                 120

118 T I T M P T E S D F L M Q A D G K P K C C F F K F S S K I         murine
118 T I M M A T E P D P I V Q V D R K P K C C F F S F S P K I         zebrafish
  1 - - - - - - - - - - - - - - - - - - - - - - - - - - - -           salmon1
  1 - - - - - - - - - - - - - - - - - - - - - - - - - - - -           salmon2
             130                 140                 150
```

FIG. 3D

```
                        310                 320                 330
298 W I I A P K R Y K A N Y C S G E C E F V F L Q K Y P H T H L   murine
296 W I I A P K R Y K A N Y C S G E C D Y M Y L Q K Y P H T H L   zebrafish
 79 W I I A P K R Y K A N Y C S G E C E Y M H L Q K Y P H T H L   salmon1
 58 W I I A P K R Y K A N Y C S G E C E Y M H L Q K Y P H T H L   salmon2

340                 350                 360
328 V H Q A N P R G S A G P C C T P T K M S P I N M L Y F N G K   murine
326 V N K A S P R G T A G P C C T P T K M S P I N M L Y F N G K   zebrafish
109 V N K A N P R G T A G P C C T P T K M S P I N M L Y F N R K   salmon1
 88 V N K A N P R G T A G P C C T P T K M S P I N M L Y F N R K   salmon2

370
358 E Q I I Y G K I P A M V V D R C G C S                         murine
356 E Q I I Y G K I P S M V V D R C G C S                         zebrafish
139 E Q I I Y G K I P S M V V D R C G C S                         salmon1
118 E Q I I Y G K I P S M V V D R C G C S                         salmon2
```

Decoration 'Decoration #1': The outlined residues that match the Concensus exactly.

FIG. 3E

| | GDF-1 | GDF-2 | GDF-3 | GDF-5 | GDF-6 | GDF-7 | GDF-8 | GDF-9 | BMP-2 | BMP-4 | Vgr-1 | OP-1 | BMP-5 | BMP-3 | MIS | Inhibinα | InhibinβA | InhibinβB | TGF-β1 | TGF-β2 | TGF-β3 |
|---|---|---|---|---|---|---|---|---|---|---|---|---|---|---|---|---|---|---|---|---|---|
| TGF-β3 | 33 | 30 | 32 | 37 | 38 | 38 | 37 | 25 | 36 | 35 | 39 | 38 | 36 | 32 | 25 | 24 | 36 | 37 | 74 | 78 | 82 | 100 |
| TGF-β2 | 32 | 28 | 31 | 34 | 36 | 35 | 37 | 25 | 34 | 33 | 37 | 38 | 35 | 32 | 23 | 22 | 37 | 34 | 74 | 100 | - | - |
| TGF-β1 | 33 | 26 | 36 | 33 | 35 | 36 | 34 | 23 | 35 | 34 | 35 | 34 | 34 | 32 | 28 | 23 | 41 | 35 | 100 | - | - | - |
| InhibinβB | 35 | 25 | 41 | 37 | 39 | 36 | 42 | 31 | 42 | 42 | 41 | 42 | 37 | 37 | 25 | 25 | 63 | 100 | - | - | - | - |
| InhibinβA | 37 | 32 | 42 | 40 | 43 | 41 | 38 | 30 | 42 | 41 | 44 | 43 | 43 | 36 | 24 | 26 | 100 | - | - | - | - | - |
| Inhibinα | 23 | 20 | 25 | 24 | 27 | 26 | 26 | 27 | 22 | 22 | 25 | 24 | 24 | 29 | 18 | 100 | - | - | - | - | - | - |
| MIS | 34 | 20 | 22 | 27 | 26 | 25 | 31 | 21 | 27 | 27 | 24 | 27 | 24 | 30 | 100 | - | - | - | - | - | - | - |
| BMP-3 | 42 | 34 | 42 | 47 | 46 | 46 | 38 | 29 | 48 | 47 | 44 | 42 | 43 | 100 | - | - | - | - | - | - | - | - |
| BMP-5 | 46 | 55 | 50 | 52 | 54 | 52 | 42 | 31 | 61 | 59 | 91 | 88 | 100 | - | - | - | - | - | - | - | - | - |
| OP-1 | 47 | 52 | 50 | 51 | 53 | 53 | 42 | 30 | 60 | 58 | 87 | 100 | - | - | - | - | - | - | - | - | - | - |
| Vgr-1 | 46 | 55 | 53 | 51 | 53 | 52 | 45 | 31 | 61 | 60 | 100 | - | - | - | - | - | - | - | - | - | - | - |
| BMP-4 | 43 | 51 | 50 | 57 | 56 | 57 | 38 | 34 | 92 | 100 | - | - | - | - | - | - | - | - | - | - | - | - |
| BMP-2 | 42 | 52 | 53 | 57 | 57 | 57 | 41 | 33 | 100 | - | - | - | - | - | - | - | - | - | - | - | - | - |
| GDF-9 | 27 | 32 | 33 | 33 | 34 | 33 | 27 | 100 | - | - | - | - | - | - | - | - | - | - | - | - | - | - |
| GDF-8 | 35 | 31 | 41 | 37 | 38 | 37 | 100 | - | - | - | - | - | - | - | - | - | - | - | - | - | - | - |
| GDF-7 | 48 | 48 | 46 | 80 | 80 | 100 | - | - | - | - | - | - | - | - | - | - | - | - | - | - | - | - |
| GDF-6 | 44 | 51 | 49 | 86 | 100 | - | - | - | - | - | - | - | - | - | - | - | - | - | - | - | - | - |
| GDF-5 | 46 | 47 | 49 | 100 | - | - | - | - | - | - | - | - | - | - | - | - | - | - | - | - | - | - |
| GDF-3 | 50 | 42 | 100 | - | - | - | - | - | - | - | - | - | - | - | - | - | - | - | - | - | - | - |
| GDF-2 | 33 | 100 | - | - | - | - | - | - | - | - | - | - | - | - | - | - | - | - | - | - | - | - |
| GDF-1 | 100 | - | - | - | - | - | - | - | - | - | - | - | - | - | - | - | - | - | - | - | - | - |

FIG. 4

```
  1 GTCTCTCGGACGGTACATGCACTAATATTTCACTTGGCATTACTCAAAAGCAAAAAGAAG  60
 61 AAATAAGAACAAGGGAAAAAAAAAGATTGTGCTGATTTTTAAAATGATGCAAAAACTGCA 120
                                              M  M  Q  K  L  Q
121 AATGTATGTTTATATTTACCTGTTCATGCTGATTGCTGCTGGCCCAGTGGATCTAAATGA 180
     M  Y  V  Y  I  Y  L  F  M  L  I  A  A  G  P  V  D  L  N  E
181 GGGCAGTGAGAGAGAAGAAAATGTGGAAAAAGAGGGGCTGTGTAATGCATGTGCGTGGAG 240
     G  S  E  R  E  E  N  V  E  K  E  G  L  C  N  A  C  A  W  R
241 ACAAAACACGAGGTACTCCAGAATAGAAGCCATAAAAATTCAAATCCTCAGTAAGCTGCG 300
     Q  N  T  R  Y  S  R  I  E  A  I  K  I  Q  I  L  S  K  L  R
301 CCTGGAAACAGCTCCTAACATCAGCAAAGATGCTATAAGACAACTTCTGCCAAGAGCGCC 360
     L  E  T  A  P [N  I  S] K  D  A  I  R  Q  L  L  P  R  A  P
361 TCCACTCCGGGAACTGATCGATCAGTACGACGTCCAGAGGGATGACAGCAGTGATGGCTC 420
     P  L  R  E  L  I  D  Q  Y  D  V  Q  R  D  D  S  S  D  G  S
421 TTTGGAAGATGACGATTATCACGCTACCACGGAAACAATCATTACCATGCCTACAGAGTC 480
     L  E  D  D  D  Y  H  A  T  T  E  T  I  I  T  M  P  T  E  S
481 TGACTTTCTAATGCAAGCGGATGGCAAGCCCAAATGTTGCTTTTTTAAATTTAGCTCTAA 540
     D  F  L  M  Q  A  D  G  K  P  K  C  C  F  F  K  F  S  S  K
541 AATACAGTACAACAAAGTAGTAAAAGCCCAACTGTGGATATATCTCAGACCCGTCAAGAC 600
     I  Q  Y  N  K  V  V  K  A  Q  L  W  I  Y  L  R  P  V  K  T
601 TCCTACAACAGTGTTTGTGCAAATCCTGAGACTCATCAAACCCATGAAAGACGGTACAAG 660
     P  T  T  V  F  V  Q  I  L  R  L  I  K  P  M  K  D  G  T  R
661 GTATACTGGAATCCGATCTCTGAAACTTGACATGAGCCCAGGCACTGGTATTTGGCAGAG 720
     Y  T  G  I  R  S  L  K  L  D  M  S  P  G  T  G  I  W  Q  S
721 TATTGATGTGAAGACAGTGTTGCAAAATTGGCTCAAACAGCCTGAATCCAACTTAGGCAT 780
     I  D  V  K  T  V  L  Q  N  W  L  K  Q  P  E  S  N  L  G  I
781 TGAAATCAAAGCTTTGGATGAGAATGGCCATGATCTTGCTGTAACCTTCCCAGGACCAGG 840
     E  I  K  A  L  D  E  N  G  H  D  L  A  V  T  F  P  G  P  G
841 AGAAGATGGGCTGAATCCCTTTTTAGAAGTCAAGGTGACAGACACACCCAAGAGGTCCCG 900
     E  D  G  L  N  P  F  L  E  V  K  V  T  D  T  P  K [R  S  R
901 GAGAGACTTTGGGCTTGACTGCGATGAGCACTCCACGGAATCCCGGTGCTGCCGCTACCC 960
     R] D  F  G  L  D  C  D  E  H  S  T  E  S  R  C  C  R  Y  P
961 CCTCACGGTCGATTTTGAAGCCTTTGGATGGGACTGGATTATCGCACCCAAAAGATATAA 1020
     L  T  V  D  F  E  A  F  G  W  D  W  I  I  A  P  K  R  Y  K
1021 GGCCAATTACTGCTCAGGAGAGTGTGAATTTGTGTTTTTACAAAAATATCCGCATACTCA 1080
      A  N  Y  C  S  G  E  C  E  F  V  F  L  Q  K  Y  P  H  T  H
1081 TCTTGTGCACCAAGCAAACCCCAGAGGCTCAGCAGGCCCTTGCTGCACTCCGACAAAAAT 1140
      L  V  H  Q  A  N  P  R  G  S  A  G  P  C  C  T  P  T  K  M
1141 GTCTCCCATTAATATGCTATATTTTAATGGCAAAGAACAAATAATATATGGGAAAATTCC 1200
      S  P  I  N  M  L  Y  F  N  G  K  E  Q  I  I  Y  G  K  I  P
1201 AGCCATGGTAGTAGACCGCTGTGGGTGCTCATGAGCTTTGCATTAGGTTAGAAACTTCCC 1260
      A  M  V  V  D  R  C  G  C  S  *
```

FIG. 5A

1261 AAGTCATGGAAGGTCTTCCCCTCAATTTCGAAACTGTGAATTCAAGCACCACAGGCTGTA 1320
1321 GGCCTTGAGTATGCTCTAGTAACGTAAGCACAAGCTACAGTGTATGAACTAAAAGAGAGA 1380
1381 ATAGATGCAATGGTTGGCATTCAACCACCAAAATAAACCATACTATAGGATGTTGTATGA 1440
1441 TTTCCAGAGTTTTTGAAATAGATGGAGATCAAATTACATTTATGTCCATATATGTATATT 1500
1501 ACAACTACAATCTAGGCAAGGAAGTGAGAGCACATCTTGTGGTCTGCTGAGTTAGGAGGG 1560
1561 TATGATTAAAAGGTAAAGTCTTATTTCCTAACAGTTTCACTTAATATTTACAGAAGAATC 1620
1621 TATATGTAGCCTTTGTAAAGTGTAGGATTGTTATCATTTAAAAACATCATGTACACTTAT 1680
1681 ATTTGTATTGTATACTTGGTAAGATAAAATTCCACAAAGTAGGAATGGGGCCTCACATAC 1740
1741 ACATTGCCATTCCTATTATAATTGGACAATCCACCACGGTGCTAATGCAGTGCTGAATGG 1800
1801 CTCCTACTGGACCTCTCGATAGAACACTCTACAAAGTACGAGTCTCTCTCTCCCTTCCAG 1860
1861 GTGCATCTCCACACACACAGCACTAAGTGTTCAATGCATTTTCTTTAAGGAAAGAAGAAT 1920
1921 CTTTTTTTCTAGAGGTCAACTTTCAGTCAACTCTAGCACAGCGGGAGTGACTGCTGCATC 1980
1981 TTAAAAGGCAGCCAAACAGTATTCATTTTTTAATCTAAATTTCAAAATCACTGTCTGCCT 2040
2041 TTATCACATGGCAATTTTGTGGTAAAATAATGGAAATGACTGGTTCTATCAATATTGTAT 2100
2101 AAAAGACTCTGAAACAATTACATTTATATAATATGTATACAATATTGTTTTGTAAATAAG 2160
2161 TGTCTCCTTTTATATTTACTTTGGTATATTTTACACTAATGAAATTTCAAATCATTAAA 2220
2221 GTACAAAGACATGTCATGTATCACAAAAAAGGTGACTGCTTCTATTTCAGAGTGAATTAG 2280
2281 CAGATTCAATAGTGGTCTTAAAACTCTGTATGTTAAGATTAGAAGGTTATATTACAATCA 2340
2341 ATTTATGTATTTTTTACATTATCAACTTATGGTTTCATGGTGGCTGTATCTATGAATGTG 2400
2401 GCTCCCAGTCAAATTTCAATGCCCCACCATTTAAAAATTACAAGCATTACTAAACATAC 2460
2461 CAACATGTATCTAAAGAAATACAAATATGGTATCTCAATAACAGCTACTTTTTTATTTTA 2520
2521 TAATTTGACAATGAATACATTTCTTTTATTTACTTCAGTTTTATAAATTGGAACTTTGTT 2580
2581 TATCAAATGTATTGTACTCATAGCTAAATGAAATTATTTCTTACATAAAAATGTGTAGAA 2640
2641 ACTATAAATTAAAGTGTTTTCACATTTTTGAAAGGC 2676

FIG. 5B

```
  1 AAGAAAAGTAAAAGGAAGAAACAAGAACAAGAAAAAAGATTATATTGATTTTAAAATCAT   60
                                                              M
 61 GCAAAAACTGCAACTCTGTGTTTATATTTACCTGTTTATGCTGATTGTTGCTGGTCCAGT  120
     Q  K  L  Q  L  C  V  Y  I  Y  L  F  M  L  I  V  A  G  P  V
121 GGATCTAAATGAGAACAGTGAGCAAAAAGAAAATGTGGAAAAAGAGGGGCTGTGTAATGC  180
     D  L  N  E  N  S  E  Q  K  E  N  V  E  K  E  G  L  C  N  A
181 ATGTACTTGGAGACAAAACACTAAATCTTCAAGAATAGAAGCCATTAAGATACAAATCCT  240
     C  T  W  R  Q  N  T  K  S  S  R  I  E  A  I  K  I  Q  I  L
241 CAGTAAACTTCGTCTGGAAACAGCTCCTAACATCAGCAAAGATGTTATAAGACAACTTTT  300
     S  K  L  R  L  E  T  A  P  N  I  S  K  D  V  I  R  Q  L  L
301 ACCCAAAGCTCCTCCACTCCGGGAACTGATTGATCAGTATGATGTCCAGAGGGATGACAG  360
     P  K  A  P  P  L  R  E  L  I  D  Q  Y  D  V  Q  R  D  D  S
361 CAGCGATGGCTCTTTGGAAGATGACGATTATCACGCTACAACGGAAACAATCATTACCAT  420
     S  D  G  S  L  E  D  D  D  Y  H  A  T  T  E  T  I  I  T  M
421 GCCTACAGAGTCTGATTTTCTAATGCAAGTGGATGGAAAACCCAAATGTTGCTTCTTTAA  480
     P  T  E  S  D  F  L  M  Q  V  D  G  K  P  K  C  C  F  F  K
481 ATTTAGCTCTAAAATACAATACAATAAAGTAGTAAAGGCCCAACTATGGATATATTTGAG  540
     F  S  S  K  I  Q  Y  N  K  V  V  K  A  Q  L  W  I  Y  L  R
541 ACCCGTCGAGACTCCTACAACAGTGTTTGTGCAAATCCTGAGACTCATCAAACCTATGAA  600
     P  V  E  T  P  T  T  V  F  V  Q  I  L  R  L  I  K  P  M  K
601 AGACGGTACAAGGTATACTGGAATCCGATCTCTGAAACTTGACATGAACCCAGGCACTGG  660
     D  G  T  R  Y  T  G  I  R  S  L  K  L  D  M  N  P  G  T  G
661 TATTTGGCAGAGCATTGATGTGAAGACAGTGTTGCAAAATTGGCTCAAACAACCTGAATC  720
     I  W  Q  S  I  D  V  K  T  V  L  Q  N  W  L  K  Q  P  E  S
721 CAACTTAGGCATTGAAATAAAAGCTTTAGATGAGAATGGTCATGATCTTGCTGTAACCTT  780
     N  L  G  I  E  I  K  A  L  D  E  N  G  H  D  L  A  V  T  F
781 CCCAGGACCAGGAGAAGATGGGCTGAATCCGTTTTTAGAGGTCAAGGTAACAGACACACC  840
     P  G  P  G  E  D  G  L  N  P  F  L  E  V  K  V  T  D  T  P
841 AAAAAGATCCAGAAGGGATTTTGGTCTTGACTGTGATGAGCACTCAACAGAATCACGATG  900
     K  R  S  R  R  D  F  G  L  D  C  D  E  H  S  T  E  S  R  C
901 CTGTCGTTACCCTCTAACTGTGGATTTTGAAGCTTTTGGATGGGATTGGATTATCGCTCC  960
     C  R  Y  P  L  T  V  D  F  E  A  F  G  W  D  W  I  I  A  P
961 TAAAAGATATAAGGCCAATTACTGCTCTGGAGAGTGTGAATTTGTATTTTTACAAAAATA 1020
     K  R  Y  K  A  N  Y  C  S  G  E  C  E  F  V  F  L  Q  K  Y
1021 TCCTCATACTCATCTGGTACACCAAGCAAACCCCAGAGGTTCAGCAGGCCCTTGCTGTAC 1080
      P  H  T  H  L  V  H  Q  A  N  P  R  G  S  A  G  P  C  C  T
1081 TCCCACAAAGATGTCTCCAATTAATATGCTATATTTTAATGGCAAAGAACAAATAATATA 1140
      P  T  K  M  S  P  I  N  M  L  Y  F  N  G  K  E  Q  I  I  Y
1141 TGGGAAAATTCCAGCGATGGTAGTAGACCGCTGTGGGTGCTCATGAGATTTATATTAAGC 1200
      G  K  I  P  A  M  V  V  D  R  C  G  C  S  *
```

FIG. 5C

```
1201 GTTCATAACTTCCTAAAACATGGAAGGTTTTCCCCTCAACAATTTTGAAGCTGTGAAATT 1260
1261 AAGTACCACAGGCTATAGGCCTAGAGTATGCTACAGTCACTTAAGCATAAGCTACAGTAT 1320
1321 GTAAACTAAAAGGGGAATATATGCAATGGTTGGCATTTAACCATCCAAACAAATCATAC 1380
1381 AAGAAAGTTTTATGATTTCCAGAGTTTTTGAGCTAGAAGGAGATCAAATTACATTTATGT 1440
1441 TCCTATATATTACAACATCGGCGAGGAAATGAAAGCGATTCTCCTTGAGTTCTGATGAAT 1500
1501 TAAAGGAGTATGCTTTAAAGTCTATTTCTTTAAAGTTTTGTTTAATATTTACAGAAAAAT 1560
1561 CCACATACAGTATTGGTAAAATGCAGGATTGTTATATACCATCATTCGAATCATCCTTAA 1620
1621 ACACTTGAATTTATATTGTATGGTAGTATACTTGGTAAGATAAAATTCCACAAAAATAGG 1680
1681 GATGGTGCAGCATATGCAATTTCCATTCCTATTATAATTGACACAGTACATTAACAATCC 1740
1741 ATGCCAACGGTGCTAATACGATAGGCTGAATGTCTGAGGCTACCAGGTTTATCACATAAA 1800
1801 AAACATTCAGTAAAATAGTAAGTTTCTCTTTTCTTCAGGTGCATTTTCCTACACCTCCAA 1860
1861 ATGAGGAATGGATTTTCTTTAATGTAAGAAGAATCATTTTTCTAGAGGTTGGCTTTCAAT 1920
1921 TCTGTAGCATACTTGGAGAAACTGCATTATCTTAAAAGGCAGTCAAATGGTGTTTGTTTT 1980
1981 TATCAAAATGTCAAAATAACATACTTGGAGAAGTATGTAATTTGTCTTTGGAAAATTAC 2040
2041 AACACTGCCTTTGCAACACTGCAGTTTTTATGGTAAAATAATAGAAATGATCGACTCTAT 2100
2101 CAATATTGTATAAAAAGACTGAAACAATGCATTTATATAATATGTATACAATATTGTTTT 2160
2161 GTAAATAAGTGTCTCCTTTTTTATTTACTTTGGTATATTTTTACACTAAGGACATTTCAA 2220
2221 ATTAAGTACTAAGGCACAAAGACATGTCATGCATCACAGAAAAGCAACTACTTATATTTC 2280
2281 AGAGCAAATTAGCAGATTAAATAGTGGTCTTAAAACTCCATATGTTAATGATTAGATGGT 2340
2341 TATATTACAATCATTTTATATTTTTTACATGATTAACATTCACTTATGGATTCATGATG 2400
2401 GCTGTATAAAGTGAATTTGAAATTTCAATGGTTTACTGTCATTGTGTTTAAATCTCAACG 2460
2461 TTCCATTATTTTAATACTTGCAAAAACATTACTAAGTATACCAAAATAATTGACTCTATT 2520
2521 ATCTGAAATGAAGAATAAACTGATGCTATCTCAACAATAACTGTTACTTTTATTTTATAA 2580
2581 TTTGATAATGAATATATTTCTGCATTTATTTACTTCTGTTTGTAAATTGGGATTTTGTT 2640
2641 AATCAAATTTATTGTACTATGACTAAATGAAATTATTTCTTACATCTAATTTGTAGAAAC 2700
2701 AGTATAAGTTATATTAAAGTGTTTTCACATTTTTTTGAAAGAC 2743
```

FIG. 5D

```
  1  MMQKLQMYVYIYLFMLIAAGPVDLNEGSEREENVEKEGLCNACAWRQNTR   50
     |||||  |||||||||| |||||||  ||  |||||||||||| |||||
  1  MQKLQLCVYIYLFMLIVAGPVDLNENSEQKENVEKEGLCNACTWRQNTK    49

51  YSRIEAIKIQILSKLRLETAPNISKDAIRQLLPRAPPLRELIDQYDVQRD  100
     |||||||||||||||||||||||||| ||||| ||||||||||||||||
 50  SSRIEAIKIQILSKLRLETAPNISKDVIRQLLPKAPPLRELIDQYDVQRD   99

101  DSSDGSLEDDDYHATTETIITMPTESDFLMQADGKPKCCFFKFSSKIQYN  150
     |||||||||||||||||||||||||||||| ||||||||||||||||||
100  DSSDGSLEDDDYHATTETIITMPTESDFLMQVDGKPKCCFFKFSSKIQYN  149

151  KVVKAQLWIYLRPVKTPTTVFVQILRLIKPMKDGTRYTGIRSLKLDMSPG  200
     |||||||||||| |||||||||||||||||||||||||||||||||| |
150  KVVKAQLWIYLRPVETPTTVFVQILRLIKPMKDGTRYTGIRSLKLDMNPG  199

201  TGIWQSIDVKTVLQNWLKQPESNLGIEIKALDENGHDLAVTFPGPGEDGL  250
     |||||||||||||||||||||||||||||||||||||||||||||||||
200  TGIWQSIDVKTVLQNWLKQPESNLGIEIKALDENGHDLAVTFPGPGEDGL  249

251  NPFLEVKVTDTPKRSRRDFGLDCDEHSTESRCCRYPLTVDFEAFGWDWII  300
     |||||||||||||||||||||||||||||||||||||||||||||||||
250  NPFLEVKVTDTPKRSRRDFGLDCDEHSTESRCCRYPLTVDFEAFGWDWII  299

301  APKRYKANYCSGECEFVFLQKYPHTHLVHQANPRGSAGPCCTPTKMSPIN  350
     |||||||||||||||||||||||||||||||||||||||||||||||||
300  APKRYKANYCSGECEFVFLQKYPHTHLVHQANPRGSAGPCCTPTKMSPIN  349

351  MLYFNGKEQIIYGKIPAMVVDRCGCS  376
     |||||||||||||||||||||||||
350  MLYFNGKEQIIYGKIPAMVVDRCGCS  375
```

FIG. 7

1 2 3 4 5 6 7 8 9 10 11 12 13 14 15 16 17 18 19 20 21 22 X Y M $\overset{CHO}{|}$ H B1

Cod DNA
[Strand]

1   ACTCCCCGAGTCCGGTGCTGCGCTACCCCCTCACAGTGGACTTTGAAGACTTTGGCTGGGACTGGGTGATCGCGCCCAAGCG
    S   P   E   S   R   C   C   R   Y   P   L   T   V   D   F   E   D   F   G   W   D   W   V   I   A   P   K   R

86  ATACAAGGCCAACTATTGCTCCGGGGAGTGTGAGTACATGTACCTGCAGAAGTACCCCCACACCCACCTGGTGCACAAGGCCAGC
    Y   K   A   N   Y   C   S   G   E   C   E   Y   M   Y   L   Q   K   Y   P   H   T   H   L   V   H   K   A   S

171 CCCCGGGGCAACGCTGGGCCCTGCTGCACGCCCACCAAGATGTCCCCATCAACATGCTCTACTTCAACCGCAAGGAGCAGATCA
    P   R   G   N   A   G   P   C   C   T   P   T   K   M   S   P   I   N   M   L   Y   F   N   R   K   E   Q   I

256 TCTACGGCAAGCTGCCCTCTATGGTCGTA
    I   Y   G   K   L   P   S   M   V   V

FIG. 14

Sea Bass
[Strand]

```
1    TGCTGCCGCTACCCACTCACAGTGGACTTTGAAGACTTTGGTTGGGACTGGATTATTGCCCCAAAGGCGCTACAAGGCCAACTATT
     C  C  R  Y  P  L  T  V  D  F  E  D  F  G  W  D  W  I  I  A  P  K  R  Y  K  A  N  Y

86   GCTCCGGGGAGTGTGAGTACATGCACTTGCAGAAGTATCCGCACACCCACCTGGTGAACAAGCCAACCCAGAGGGACCGGCGGG
     C  S  G  E  C  E  Y  M  H  L  Q  K  Y  P  H  T  H  L  V  N  K  A  N  P  R  G  T  A  G

171  TCCCTGCTGCACCCCGACCAAGATGTCGCCATNAACATGCTCTACTTTAACCGAAAAGAGCAGATAATCTACGGCAAGATCCCT
     P  C  C  T  P  T  K  M  S  P  ?  N  M  L  Y  F  N  R  K  E  Q  I  I  Y  G  K  I  P

256  TCCATGGTGGTG
     S  M  V  V
```

FIG. 15

Sea Bream DNA
[Strand]

```
1    TCTCAGAGTCCCGGTCTGCCGCTACCCGCTCAGGTGGACTGGATTATTGCCCAAAGCGCTA
      S  E  S  R  C  C  R  Y  P  L  T  V  D  F  E  D  F  G  W  D  W  I  I  A  P  K  R  Y

86   CAAGGCCAACTATTGCTCCGGGGAGTGTGAGTACATGCACTTGCAGAAGTACCCGCACACCCACCTGGTGAACAAGCCAACCCC
      K  A  N  Y  C  S  G  E  C  E  Y  M  H  L  Q  K  Y  P  H  T  H  L  V  N  K  A  N  P

171  AGAGGGTCCGCGGGCCCCTGCTGTACCCCACCAAGATGTCGCCCATCAACATGCTCTACTTTAACCGAAAGGAGCAGATCATCT
      R  G  S  A  G  P  C  C  T  P  T  K  M  S  P  I  N  M  L  Y  F  N  R  K  E  Q  I  I

256  ACGGCAAGATCCCGTCCATGGTGGTA
      Y  G  K  I  P  S  M  V  V
```

FIG. 16

Tautog DNA
[Strand]

1   CTCAGAGTCCCGGTGCTGCCGCTACCCACTCACAGTGGACTTTGCTGGAGACTGGATTATTGCTCCAAAGCGCTAC
    S   E   S   R   C   C   R   Y   P   L   T   V   D   F   F   E   D   F   G   W   D   W   I   I   A   P   K   R   Y

86  AAGGCCAACTATTGCTCCGGGGAGTGTGAGTACATGCACCTGCAGAAGTACCCACACCCACCTGTGAACAAGCCAACCCA
    K   A   N   Y   C   S   G   E   C   E   Y   M   H   L   Q   K   Y   P   H   T   H   L   V   N   K   A   N   P

171 GAGGGACTGCAGGCCCCTGCCTGCACCCCCACCAAGATGTCGCCCATCAACATGCTCTACTTTAACCGAAAGGAGCAGATCATCTA
    R   G   T   A   G   P   C   C   T   P   T   K   M   S   P   I   N   M   L   Y   F   N   R   K   E   Q   I   I   Y

256 CGGCAAGATCCCCTCCATGGTGGTG
    G   K   I   P   S   M   V   V

FIG. 17

X. laevis T7
[Strand]

```
1    TCCAAAACGATATAAAGCCAACTATTGCTCTGAGAGTGCGGCATTGTCTTTTTGCAAAAGTACCCGCACACATCTTGTTCAA
      P  K  R  Y  K  A  N  Y  C  S  G  E  C  G  I  V  F  L  Q  K  Y  P  H  T  H  L  V  Q

86   CAAGCAAACCCCAGAGTTCTGCTGGCCCTTGCTGTACCCCAACCAAAATGTCCCAATTAATATGTTATTTCAATGAAATG
      Q  A  N  P  R  G  S  A  G  P  C  C  T  P  T  K  M  S  P  I  N  M  L  Y  F  N  E  N

171  AACAAATCATATATGGAAAAATTCCAGCTATGGTGGTA
      E  Q  I  I  Y  G  K  I  P  A  M  V  V
```

FIG. 18

| | | | | | Percent Similarity | | | | | | |
|---|---|---|---|---|---|---|---|---|---|---|---|
| | | 1 | 2 | 3 | 4 | 5 | 6 | 7 | 8 | | |
| | 1 | | 88.8 | 89.9 | 87.6 | 88.8 | 91.0 | 88.8 | 92.8 | 1 | humanMSTN |
| Percent Divergence | 2 | 11.2 | | 95.5 | 93.3 | 94.4 | 94.4 | 94.4 | 84.1 | 2 | Zebrafish |
| | 3 | 10.1 | 4.5 | | 93.3 | 98.9 | 98.9 | 98.9 | 85.5 | 3 | Salmon |
| | 4 | 12.4 | 6.7 | 6.7 | | 92.1 | 93.3 | 92.1 | 82.6 | 4 | Cod |
| | 5 | 10.2 | 4.5 | 0.0 | 6.8 | | 97.8 | 97.8 | 84.1 | 5 | Sea Bass |
| | 6 | 9.0 | 5.6 | 1.1 | 6.7 | 1.1 | | 97.8 | 87.0 | 6 | Sea Bream |
| | 7 | 11.2 | 5.6 | 1.1 | 7.9 | 1.1 | 2.2 | | 85.5 | 7 | Tautog |
| | 8 | 7.2 | 15.9 | 14.5 | 17.4 | 14.7 | 13.0 | 14.5 | | 8 | X. laevis |
| | | 1 | 2 | 3 | 4 | 5 | 6 | 7 | 8 | | |

FIG. 20

SEQUENCE LISTING

<160> NUMBER OF SEQ ID NOS: 53

<210> SEQ ID NO 1
<211> LENGTH: 36
<212> TYPE: DNA
<213> ORGANISM: Artificial Sequence
<220> FEATURE:
<223> OTHER INFORMATION: Oligonucleotide for PCR
<220> FEATURE:
<221> NAME/KEY: misc_feature
<222> LOCATION: (1)..(36)
<223> OTHER INFORMATION: n = A, T, G, or C

<400> SEQUENCE: 1
ccggaattcg gntggvanra ytggrtnrtn nkcncc                                36

<210> SEQ ID NO 2
<211> LENGTH: 33
<212> TYPE: DNA
<213> ORGANISM: Artificial Sequence
<220> FEATURE:
<223> OTHER INFORMATION: Oligonucleotide for PCR
<220> FEATURE:
<221> NAME/KEY: misc_feature
<222> LOCATION: (1)..(33)
<223> OTHER INFORMATION: n = A, T, G, or C

<400> SEQUENCE: 2
ccggaattcr canscrcarc tntcnacnry cat                                  33

<210> SEQ ID NO 3
<211> LENGTH: 32
<212> TYPE: DNA
<213> ORGANISM: Artificial Sequence
<220> FEATURE:
<223> OTHER INFORMATION: Oligonucleotide for PCR

<400> SEQUENCE: 3
cgcggatcca gaagtcaagg tgacagacac ac                                   32

<210> SEQ ID NO 4
<211> LENGTH: 33
<212> TYPE: DNA
<213> ORGANISM: Artificial Sequence
<220> FEATURE:
<223> OTHER INFORMATION: Oligonucleotide for PCR

<400> SEQUENCE: 4
cgcggatcct cctcatgagc acccacagcg gtc                                  33

<210> SEQ ID NO 5
<211> LENGTH: 550
<212> TYPE: DNA
<213> ORGANISM: Mus musculus
<220> FEATURE:
<221> NAME/KEY: CDS
<222> LOCATION: (59)..(436)
<223> OTHER INFORMATION:

<400> SEQUENCE: 5
ttaaggtagg aaggatttca ggctctattt acataattgt tctttccttt tcacacag       58 aat ccc ttt tta gaa gtc aag gtg aca gac aca ccc aag agg tcc cgg      106
Asn Pro Phe Leu Glu Val Lys Val Thr Asp Thr Pro Lys Arg Ser Arg
1               5                   10                  15 aga gac ttt ggg ctt gac tgc gat gag cac tcc acg gaa tcc cgg tgc      154

```
Arg Asp Phe Gly Leu Asp Cys Asp Glu His Ser Thr Glu Ser Arg Cys
         20                  25                  30 tgc cgc tac ccc ctc acg gtc gat ttt gaa gcc ttt gga tgg gac tgg        202
Cys Arg Tyr Pro Leu Thr Val Asp Phe Glu Ala Phe Gly Trp Asp Trp
         35                  40                  45 att atc gca ccc aaa aga tat aag gcc aat tac tgc tca gga gag tgt        250
Ile Ile Ala Pro Lys Arg Tyr Lys Ala Asn Tyr Cys Ser Gly Glu Cys
 50                  55                  60 gaa ttt gtg ttt tta caa aaa tat ccg cat act cat ctt gtg cac caa        298
Glu Phe Val Phe Leu Gln Lys Tyr Pro His Thr His Leu Val His Gln
 65                  70                  75                  80 gca aac ccc aga ggc tca gca ggc cct tgc tgc act ccg aca aaa atg        346
Ala Asn Pro Arg Gly Ser Ala Gly Pro Cys Cys Thr Pro Thr Lys Met
             85                  90                  95 tct ccc att aat atg cta tat ttt aat ggc aaa gaa caa ata ata tat        394
Ser Pro Ile Asn Met Leu Tyr Phe Asn Gly Lys Glu Gln Ile Ile Tyr
            100                 105                 110 ggg aaa att cca gcc atg gta gta gac cgc tgt ggg tgc tca                436
Gly Lys Ile Pro Ala Met Val Val Asp Arg Cys Gly Cys Ser
            115                 120                 125 tgagctttgc attaggttag aaacttccca agtcatggaa ggtcttcccc tcaatttcga      496
aactgtgaat tcctgcagcc cgggggatcc actagttcta gagcggccgc cacc            550

<210> SEQ ID NO 6
<211> LENGTH: 126
<212> TYPE: PRT
<213> ORGANISM: Mus musculus

<400> SEQUENCE: 6

Asn Pro Phe Leu Glu Val Lys Val Thr Asp Thr Pro Lys Arg Ser Arg
 1               5                  10                  15

Arg Asp Phe Gly Leu Asp Cys Asp Glu His Ser Thr Glu Ser Arg Cys
             20                  25                  30

Cys Arg Tyr Pro Leu Thr Val Asp Phe Glu Ala Phe Gly Trp Asp Trp
         35                  40                  45

Ile Ile Ala Pro Lys Arg Tyr Lys Ala Asn Tyr Cys Ser Gly Glu Cys
 50                  55                  60

Glu Phe Val Phe Leu Gln Lys Tyr Pro His Thr His Leu Val His Gln
 65                  70                  75                  80

Ala Asn Pro Arg Gly Ser Ala Gly Pro Cys Cys Thr Pro Thr Lys Met
             85                  90                  95

Ser Pro Ile Asn Met Leu Tyr Phe Asn Gly Lys Glu Gln Ile Ile Tyr
            100                 105                 110

Gly Lys Ile Pro Ala Met Val Val Asp Arg Cys Gly Cys Ser
            115                 120                 125

<210> SEQ ID NO 7
<211> LENGTH: 326
<212> TYPE: DNA
<213> ORGANISM: Homo sapiens
<220> FEATURE:
<221> NAME/KEY: CDS
<222> LOCATION: (3)..(326)
<223> OTHER INFORMATION:

<400> SEQUENCE: 7 ca aaa aga tcc aga agg gat ttt ggt ctt gac tgt gat gag cac tca         47
   Lys Arg Ser Arg Arg Asp Phe Gly Leu Asp Cys Asp Glu His Ser
```

```
                1               5                   10                  15
aca gaa tca cga tgc tgt cgt tac cct cta act gtg gat ttt gaa gct         95
Thr Glu Ser Arg Cys Cys Arg Tyr Pro Leu Thr Val Asp Phe Glu Ala
                20                  25                  30 ttt gga tgg gat tgg att atc gct cct aaa aga tat aag gcc aat tac        143
Phe Gly Trp Asp Trp Ile Ile Ala Pro Lys Arg Tyr Lys Ala Asn Tyr
                35                  40                  45 tgc tct gga gag tgt gaa ttt gta ttt tta caa aaa tat cct cat act        191
Cys Ser Gly Glu Cys Glu Phe Val Phe Leu Gln Lys Tyr Pro His Thr
        50                  55                  60 cat ctg gta cac caa gca aac ccc aga ggt tca gca ggc cct tgc tgt        239
His Leu Val His Gln Ala Asn Pro Arg Gly Ser Ala Gly Pro Cys Cys
        65                  70                  75 act ccc aca aag atg tct cca att aat atg cta tat ttt aat ggc aaa        287
Thr Pro Thr Lys Met Ser Pro Ile Asn Met Leu Tyr Phe Asn Gly Lys
80                  85                  90                  95 gaa caa ata ata tat ggg aaa att cca gcg atg gta gta                    326
Glu Gln Ile Ile Tyr Gly Lys Ile Pro Ala Met Val Val
                100                 105
```

<210> SEQ ID NO 8
<211> LENGTH: 108
<212> TYPE: PRT
<213> ORGANISM: Homo sapiens

<400> SEQUENCE: 8

```
Lys Arg Ser Arg Arg Asp Phe Gly Leu Asp Cys Asp Glu His Ser Thr
1               5                   10                  15

Glu Ser Arg Cys Cys Arg Tyr Pro Leu Thr Val Asp Phe Glu Ala Phe
                20                  25                  30

Gly Trp Asp Trp Ile Ile Ala Pro Lys Arg Tyr Lys Ala Asn Tyr Cys
            35                  40                  45

Ser Gly Glu Cys Glu Phe Val Phe Leu Gln Lys Tyr Pro His Thr His
        50                  55                  60

Leu Val His Gln Ala Asn Pro Arg Gly Ser Ala Gly Pro Cys Cys Thr
65                  70                  75                  80

Pro Thr Lys Met Ser Pro Ile Asn Met Leu Tyr Phe Asn Gly Lys Glu
                85                  90                  95

Gln Ile Ile Tyr Gly Lys Ile Pro Ala Met Val Val
                100                 105
```

<210> SEQ ID NO 9
<211> LENGTH: 9
<212> TYPE: PRT
<213> ORGANISM: Artificial Sequence
<220> FEATURE:
<223> OTHER INFORMATION: Predicted amino acid sequence for SEQ ID NO: 1
<220> FEATURE:
<221> NAME/KEY: MISC_FEATURE
<222> LOCATION: (3)..(3)
<223> OTHER INFORMATION: Xaa = His, Gln, Asn, Lys, Asp, or Glu
<220> FEATURE:
<221> NAME/KEY: MISC_FEATURE
<222> LOCATION: (4)..(4)
<223> OTHER INFORMATION: Xaa = Asp or Asn
<220> FEATURE:
<221> NAME/KEY: MISC_FEATURE
<222> LOCATION: (6)..(7)
<223> OTHER INFORMATION: Xaa = Val, Ile, or Met
<220> FEATURE:
<221> NAME/KEY: MISC_FEATURE
<222> LOCATION: (8)..(8)
<223> OTHER INFORMATION: Xaa = Ala or Ser -continued

```
<400> SEQUENCE: 9

Gly Trp Xaa Xaa Trp Xaa Xaa Xaa Pro
1               5

<210> SEQ ID NO 10
<211> LENGTH: 8
<212> TYPE: PRT
<213> ORGANISM: Artificial Sequence
<220> FEATURE:
<223> OTHER INFORMATION: Predicted amino acid sequence for SEQ ID NO: 2
<220> FEATURE:
<221> NAME/KEY: MISC_FEATURE
<222> LOCATION: (2)..(2)
<223> OTHER INFORMATION: Xaa = Val, Ile, Met, Thr, or Ala
<220> FEATURE:
<221> NAME/KEY: MISC_FEATURE
<222> LOCATION: (4)..(4)
<223> OTHER INFORMATION: Xaa = Asp or Glu
<220> FEATURE:
<221> NAME/KEY: MISC_FEATURE
<222> LOCATION: (7)..(7)
<223> OTHER INFORMATION: Xaa = Gly or Ala

<400> SEQUENCE: 10

Met Xaa Val Xaa Ser Cys Xaa Cys
1               5

<210> SEQ ID NO 11
<211> LENGTH: 2676
<212> TYPE: DNA
<213> ORGANISM: Mus musculus
<220> FEATURE:
<221> NAME/KEY: CDS
<222> LOCATION: (104)..(1231)
<223> OTHER INFORMATION:

<400> SEQUENCE: 11
gtctctcgga cggtacatgc actaatattt cacttggcat tactcaaaag caaaagaag         60 aaataagaac aagggaaaaa aaaagattgt gctgattttt aaa atg atg caa aaa        115
                                                 Met Met Gln Lys
                                                 1 ctg caa atg tat gtt tat att tac ctg ttc atg ctg att gct gct ggc        163
Leu Gln Met Tyr Val Tyr Ile Tyr Leu Phe Met Leu Ile Ala Ala Gly
5               10                  15                  20 cca gtg gat cta aat gag ggc agt gag aga gaa gaa aat gtg gaa aaa        211
Pro Val Asp Leu Asn Glu Gly Ser Glu Arg Glu Glu Asn Val Glu Lys
            25                  30                  35 gag ggg ctg tgt aat gca tgt gcg tgg aga caa aac acg agg tac tcc        259
Glu Gly Leu Cys Asn Ala Cys Ala Trp Arg Gln Asn Thr Arg Tyr Ser
        40                  45                  50 aga ata gaa gcc ata aaa att caa atc ctc agt aag ctg cgc ctg gaa        307
Arg Ile Glu Ala Ile Lys Ile Gln Ile Leu Ser Lys Leu Arg Leu Glu
    55                  60                  65 aca gct cct aac atc agc aaa gat gct ata aga caa ctt ctg cca aga        355
Thr Ala Pro Asn Ile Ser Lys Asp Ala Ile Arg Gln Leu Leu Pro Arg
70                  75                  80 gcg cct cca ctc cgg gaa ctg atc gat cag tac gac gtc cag agg gat        403
Ala Pro Pro Leu Arg Glu Leu Ile Asp Gln Tyr Asp Val Gln Arg Asp
    85                  90                  95                  100 gac agc agt gat ggc tct ttg gaa gat gac gat tat cac gct acc acg        451
Asp Ser Ser Asp Gly Ser Leu Glu Asp Asp Asp Tyr His Ala Thr Thr
                105                 110                 115 gaa aca atc att acc atg cct aca gag tct gac ttt cta atg caa gcg        499
Glu Thr Ile Ile Thr Met Pro Thr Glu Ser Asp Phe Leu Met Gln Ala
            120                 125                 130
```

| | | |
|---|---|---|
| gat ggc aag ccc aaa tgt tgc ttt ttt aaa ttt agc tct aaa ata cag<br>Asp Gly Lys Pro Lys Cys Cys Phe Phe Lys Phe Ser Ser Lys Ile Gln<br>           135                  140                  145 | | 547 |
| tac aac aaa gta gta aaa gcc caa ctg tgg ata tat ctc aga ccc gtc<br>Tyr Asn Lys Val Val Lys Ala Gln Leu Trp Ile Tyr Leu Arg Pro Val<br>150                  155                  160 | | 595 |
| aag act cct aca aca gtg ttt gtg caa atc ctg aga ctc atc aaa ccc<br>Lys Thr Pro Thr Thr Val Phe Val Gln Ile Leu Arg Leu Ile Lys Pro<br>165                  170                 175              180 | | 643 |
| atg aaa gac ggt aca agg tat act gga atc cga tct ctg aaa ctt gac<br>Met Lys Asp Gly Thr Arg Tyr Thr Gly Ile Arg Ser Leu Lys Leu Asp<br>           185                    190                 195 | | 691 |
| atg agc cca ggc act ggt att tgg cag agt att gat gtg aag aca gtg<br>Met Ser Pro Gly Thr Gly Ile Trp Gln Ser Ile Asp Val Lys Thr Val<br>           200                    205               210 | | 739 |
| ttg caa aat tgg ctc aaa cag cct gaa tcc aac tta ggc att gaa atc<br>Leu Gln Asn Trp Leu Lys Gln Pro Glu Ser Asn Leu Gly Ile Glu Ile<br>           215                    220               225 | | 787 |
| aaa gct ttg gat gag aat ggc cat gat ctt gct gta acc ttc cca gga<br>Lys Ala Leu Asp Glu Asn Gly His Asp Leu Ala Val Thr Phe Pro Gly<br>230                  235                  240 | | 835 |
| cca gga gaa gat ggg ctg aat ccc ttt tta gaa gtc aag gtg aca gac<br>Pro Gly Glu Asp Gly Leu Asn Pro Phe Leu Glu Val Lys Val Thr Asp<br>245                  250                  255              260 | | 883 |
| aca ccc aag agg tcc cgg aga gac ttt ggg ctt gac tgc gat gag cac<br>Thr Pro Lys Arg Ser Arg Arg Asp Phe Gly Leu Asp Cys Asp Glu His<br>                 265                    270               275 | | 931 |
| tcc acg gaa tcc cgg tgc tgc cgc tac ccc ctc acg gtc gat ttt gaa<br>Ser Thr Glu Ser Arg Cys Cys Arg Tyr Pro Leu Thr Val Asp Phe Glu<br>           280                    285               290 | | 979 |
| gcc ttt gga tgg gac tgg att atc gca ccc aaa aga tat aag gcc aat<br>Ala Phe Gly Trp Asp Trp Ile Ile Ala Pro Lys Arg Tyr Lys Ala Asn<br>           295                    300               305 | | 1027 |
| tac tgc tca gga gag tgt gaa ttt gtg ttt tta caa aaa tat ccg cat<br>Tyr Cys Ser Gly Glu Cys Glu Phe Val Phe Leu Gln Lys Tyr Pro His<br>           310                    315               320 | | 1075 |
| act cat ctt gtg cac caa gca aac ccc aga ggc tca gca ggc cct tgc<br>Thr His Leu Val His Gln Ala Asn Pro Arg Gly Ser Ala Gly Pro Cys<br>325                  330                  335              340 | | 1123 |
| tgc act ccg aca aaa atg tct ccc att aat atg cta tat ttt aat ggc<br>Cys Thr Pro Thr Lys Met Ser Pro Ile Asn Met Leu Tyr Phe Asn Gly<br>                 345                    350               355 | | 1171 |
| aaa gaa caa ata ata tat ggg aaa att cca gcc atg gta gta gac cgc<br>Lys Glu Gln Ile Ile Tyr Gly Lys Ile Pro Ala Met Val Val Asp Arg<br>           360                    365               370 | | 1219 |
| tgt ggg tgc tca tgagctttgc attaggttag aaacttccca agtcatggaa<br>Cys Gly Cys Ser<br>375 | | 1271 |
| ggtcttcccc tcaatttcga aactgtgaat tcaagcacca caggctgtag gccttgagta | | 1331 |
| tgctctagta acgtaagcac aagctacagt gtatgaacta aaagagagaa tagatgcaat | | 1391 |
| ggttggcatt caaccaccaa aataaaccat actataggat gttgtatgat ttccagagtt | | 1451 |
| tttgaaatag atggagatca aattacattt atgtccatat atgtatatta caactacaat | | 1511 |
| ctaggcaagg aagtgagagc acatcttgtg gtctgctgag ttaggagggt atgattaaaa | | 1571 |
| ggtaaagtct tatttcctaa cagtttcact taatatttac agaagaatct atatgtagcc | | 1631 |
| tttgtaaagt gtaggattgt tatcatttaa aaacatcatg tacacttata tttgtattgt | | 1691 |

-continued

```
atacttggta agataaaatt ccacaaagta ggaatggggc ctcacataca cattgccatt   1751
cctattataa ttggacaatc caccacggtg ctaatgcagt gctgaatggc tcctactgga   1811
cctctcgata gaacactcta caaagtacga gtctctctct cccttccagg tgcatctcca   1871
cacacacagc actaagtgtt caatgcattt tctttaagga agaagaatc ttttttttcta   1931
gaggtcaact ttcagtcaac tctagcacag cgggagtgac tgctgcatct taaaaggcag   1991
ccaaacagta ttcatttttt aatctaaatt tcaaaatcac tgtctgcctt tatcacatgg   2051
caattttgtg gtaaaataat ggaaatgact ggttctatca atattgtata aaagactctg   2111
aaacaattac atttatataa tatgtataca atattgtttt gtaaataagt gtctcctttt   2171
atatttactt tggtatattt ttacactaat gaaatttcaa atcattaaag tacaaagaca   2231
tgtcatgtat cacaaaaaag gtgactgctt ctatttcaga gtgaattagc agattcaata   2291
gtggtcttaa aactctgtat gttaagatta gaaggttata ttacaatcaa tttatgtatt   2351
ttttacatta tcaacttatg gtttcatggt ggctgtatct atgaatgtgg ctcccagtca   2411
aatttcaatg ccccaccatt ttaaaaatta caagcattac taaacatacc aacatgtatc   2471
taaagaaata caaatatggt atctcaataa cagctacttt tttatttat aatttgacaa   2531
tgaatacatt tcttttatt acttcagttt tataaattgg aactttgttt atcaaatgta   2591
ttgtactcat agctaaatga aattatttct tacataaaaa tgtgtagaaa ctataaatta   2651
aagtgttttc acattttga aaggc                                         2676

<210> SEQ ID NO 12
<211> LENGTH: 376
<212> TYPE: PRT
<213> ORGANISM: Mus musculus

<400> SEQUENCE: 12

Met Met Gln Lys Leu Gln Met Tyr Val Tyr Ile Tyr Leu Phe Met Leu
1               5                   10                  15

Ile Ala Ala Gly Pro Val Asp Leu Asn Glu Gly Ser Glu Arg Glu Glu
            20                  25                  30

Asn Val Glu Lys Glu Gly Leu Cys Asn Ala Cys Ala Trp Arg Gln Asn
        35                  40                  45

Thr Arg Tyr Ser Arg Ile Glu Ala Ile Lys Ile Gln Ile Leu Ser Lys
    50                  55                  60

Leu Arg Leu Glu Thr Ala Pro Asn Ile Ser Lys Asp Ala Ile Arg Gln
65                  70                  75                  80

Leu Leu Pro Arg Ala Pro Pro Leu Arg Glu Leu Ile Asp Gln Tyr Asp
                85                  90                  95

Val Gln Arg Asp Asp Ser Ser Asp Gly Ser Leu Glu Asp Asp Asp Tyr
            100                 105                 110

His Ala Thr Thr Glu Thr Ile Ile Thr Met Pro Thr Glu Ser Asp Phe
        115                 120                 125

Leu Met Gln Ala Asp Gly Lys Pro Lys Cys Cys Phe Phe Lys Phe Ser
    130                 135                 140

Ser Lys Ile Gln Tyr Asn Lys Val Val Lys Ala Gln Leu Trp Ile Tyr
145                 150                 155                 160

Leu Arg Pro Val Lys Thr Pro Thr Thr Val Phe Val Gln Ile Leu Arg
                165                 170                 175

Leu Ile Lys Pro Met Lys Asp Gly Thr Arg Tyr Thr Gly Ile Arg Ser
            180                 185                 190

Leu Lys Leu Asp Met Ser Pro Gly Thr Gly Ile Trp Gln Ser Ile Asp
```

-continued

```
                195                 200                 205
Val Lys Thr Val Leu Gln Asn Trp Leu Lys Gln Pro Glu Ser Asn Leu
    210                 215                 220

Gly Ile Glu Ile Lys Ala Leu Asp Glu Asn Gly His Asp Leu Ala Val
225                 230                 235                 240

Thr Phe Pro Gly Pro Gly Glu Asp Gly Leu Asn Pro Phe Leu Glu Val
            245                 250                 255

Lys Val Thr Asp Thr Pro Lys Arg Ser Arg Arg Asp Phe Gly Leu Asp
                260                 265                 270

Cys Asp Glu His Ser Thr Glu Ser Arg Cys Cys Arg Tyr Pro Leu Thr
            275                 280                 285

Val Asp Phe Glu Ala Phe Gly Trp Asp Trp Ile Ile Ala Pro Lys Arg
    290                 295                 300

Tyr Lys Ala Asn Tyr Cys Ser Gly Glu Cys Glu Phe Val Phe Leu Gln
305                 310                 315                 320

Lys Tyr Pro His Thr His Leu Val His Gln Ala Asn Pro Arg Gly Ser
                325                 330                 335

Ala Gly Pro Cys Cys Thr Pro Thr Lys Met Ser Pro Ile Asn Met Leu
            340                 345                 350

Tyr Phe Asn Gly Lys Glu Gln Ile Ile Tyr Gly Lys Ile Pro Ala Met
                355                 360                 365

Val Val Asp Arg Cys Gly Cys Ser
    370                 375

<210> SEQ ID NO 13
<211> LENGTH: 2743
<212> TYPE: DNA
<213> ORGANISM: Homo sapiens
<220> FEATURE:
<221> NAME/KEY: CDS
<222> LOCATION: (59)..(1183)
<223> OTHER INFORMATION:

<400> SEQUENCE: 13
aagaaaagta aaggaagaa acaagaacaa gaaaaaagat tatattgatt ttaaaatc          58 atg caa aaa ctg caa ctc tgt gtt tat att tac ctg ttt atg ctg att      106
Met Gln Lys Leu Gln Leu Cys Val Tyr Ile Tyr Leu Phe Met Leu Ile
1               5                   10                  15 gtt gct ggt cca gtg gat cta aat gag aac agt gag caa aaa gaa aat      154
Val Ala Gly Pro Val Asp Leu Asn Glu Asn Ser Glu Gln Lys Glu Asn
                20                  25                  30 gtg gaa aaa gag ggg ctg tgt aat gca tgt act tgg aga caa aac act      202
Val Glu Lys Glu Gly Leu Cys Asn Ala Cys Thr Trp Arg Gln Asn Thr
            35                  40                  45 aaa tct tca aga ata gaa gcc att aag ata caa atc ctc agt aaa ctt      250
Lys Ser Ser Arg Ile Glu Ala Ile Lys Ile Gln Ile Leu Ser Lys Leu
    50                  55                  60 cgt ctg gaa aca gct cct aac atc agc aaa gat gtt ata aga caa ctt      298
Arg Leu Glu Thr Ala Pro Asn Ile Ser Lys Asp Val Ile Arg Gln Leu
65                  70                  75                  80 tta ccc aaa gct cct cca ctc cgg gaa ctg att gat cag tat gat gtc      346
Leu Pro Lys Ala Pro Pro Leu Arg Glu Leu Ile Asp Gln Tyr Asp Val
                85                  90                  95 cag agg gat gac agc agc gat ggc tct ttg gaa gat gac gat tat cac      394
Gln Arg Asp Asp Ser Ser Asp Gly Ser Leu Glu Asp Asp Tyr His
                100                 105                 110 gct aca acg gaa aca atc att acc atg cct aca gag tct gat ttt cta      442
Ala Thr Thr Glu Thr Ile Ile Thr Met Pro Thr Glu Ser Asp Phe Leu
```

```
                    115                 120                 125
atg caa gtg gat gga aaa ccc aaa tgt tgc ttc ttt aaa ttt agc tct      490
Met Gln Val Asp Gly Lys Pro Lys Cys Cys Phe Phe Lys Phe Ser Ser
        130                 135                 140 aaa ata caa tac aat aaa gta gta aag gcc caa cta tgg ata tat ttg      538
Lys Ile Gln Tyr Asn Lys Val Val Lys Ala Gln Leu Trp Ile Tyr Leu
145                 150                 155                 160 aga ccc gtc gag act cct aca aca gtg ttt gtg caa atc ctg aga ctc      586
Arg Pro Val Glu Thr Pro Thr Thr Val Phe Val Gln Ile Leu Arg Leu
                165                 170                 175 atc aaa cct atg aaa gac ggt aca agg tat act gga atc cga tct ctg      634
Ile Lys Pro Met Lys Asp Gly Thr Arg Tyr Thr Gly Ile Arg Ser Leu
            180                 185                 190 aaa ctt gac atg aac cca ggc act ggt att tgg cag agc att gat gtg      682
Lys Leu Asp Met Asn Pro Gly Thr Gly Ile Trp Gln Ser Ile Asp Val
                195                 200                 205 aag aca gtg ttg caa aat tgg ctc aaa caa cct gaa tcc aac tta ggc      730
Lys Thr Val Leu Gln Asn Trp Leu Lys Gln Pro Glu Ser Asn Leu Gly
210                 215                 220 att gaa ata aaa gct tta gat gag aat ggt cat gat ctt gct gta acc      778
Ile Glu Ile Lys Ala Leu Asp Glu Asn Gly His Asp Leu Ala Val Thr
225                 230                 235                 240 ttc cca gga cca gga gaa gat ggg ctg aat ccg ttt tta gag gtc aag      826
Phe Pro Gly Pro Gly Glu Asp Gly Leu Asn Pro Phe Leu Glu Val Lys
                245                 250                 255 gta aca gac aca cca aaa aga tcc aga agg gat ttt ggt ctt gac tgt      874
Val Thr Asp Thr Pro Lys Arg Ser Arg Arg Asp Phe Gly Leu Asp Cys
            260                 265                 270 gat gag cac tca aca gaa tca cga tgc tgt cgt tac cct cta act gtg      922
Asp Glu His Ser Thr Glu Ser Arg Cys Cys Arg Tyr Pro Leu Thr Val
        275                 280                 285 gat ttt gaa gct ttt gga tgg gat tgg att atc gct cct aaa aga tat      970
Asp Phe Glu Ala Phe Gly Trp Asp Trp Ile Ile Ala Pro Lys Arg Tyr
    290                 295                 300 aag gcc aat tac tgc tct gga gag tgt gaa ttt gta ttt tta caa aaa      1018
Lys Ala Asn Tyr Cys Ser Gly Glu Cys Glu Phe Val Phe Leu Gln Lys
305                 310                 315                 320 tat cct cat act cat ctg gta cac caa gca aac ccc aga ggt tca gca      1066
Tyr Pro His Thr His Leu Val His Gln Ala Asn Pro Arg Gly Ser Ala
                325                 330                 335 ggc cct tgc tgt act ccc aca aag atg tct cca att aat atg cta tat      1114
Gly Pro Cys Cys Thr Pro Thr Lys Met Ser Pro Ile Asn Met Leu Tyr
            340                 345                 350 ttt aat ggc aaa gaa caa ata ata tat ggg aaa att cca gcg atg gta      1162
Phe Asn Gly Lys Glu Gln Ile Ile Tyr Gly Lys Ile Pro Ala Met Val
        355                 360                 365 gta gac cgc tgt ggg tgc tca tgagatttat attaagcgtt cataacttcc        1213
Val Asp Arg Cys Gly Cys Ser
    370                 375 taaaacatgg aaggttttcc cctcaacaat tttgaagctg tgaaattaag taccacaggc   1273
tataggccta gagtatgcta cagtcactta agcataagct acagtatgta aactaaaagg   1333
gggaatatat gcaatggttg gcatttaacc atccaaacaa atcatacaag aaagttttat   1393
gatttccaga gttttgagc tagaaggaga tcaaattaca tttatgttcc tatatattac    1453
aacatcggcg aggaaatgaa agcgattctc cttgagttct gatgaattaa aggagtatgc   1513
tttaaagtct atttctttaa agttttgttt aatatttaca gaaaaatcca catacagtat   1573
tggtaaaatg caggattgtt ataaccatc attcgaatca tccttaaaca cttgaattta   1633
```

```
tattgtatgg tagtatactt ggtaagataa aattccacaa aaatagggat ggtgcagcat   1693
atgcaatttc cattcctatt ataattgaca cagtacatta acaatccatg ccaacggtgc   1753
taatacgata ggctgaatgt ctgaggctac caggtttatc acataaaaaa cattcagtaa   1813
aatagtaagt ttctcttttc ttcaggtgca ttttcctaca cctccaaatg aggaatggat   1873
tttctttaat gtaagaagaa tcattttcct agaggttggc tttcaattct gtagcatact   1933
tggagaaact gcattatctt aaaaggcagt caaatggtgt ttgtttttat caaaatgtca   1993
aaataacata cttggagaag tatgtaattt tgtctttgga aaattacaac actgcctttg   2053
caacactgca gttttatgg taaaataata gaaatgatcg actctatcaa tattgtataa    2113
aaagactgaa acaatgcatt tatataatat gtatacaata ttgttttgta ataagtgtc    2173
tccttttta tttactttgg tatattttta cactaaggac atttcaaatt aagtactaag    2233
gcacaaagac atgtcatgca tcacagaaaa gcaactactt atatttcaga gcaaattagc   2293
agattaaata gtggtcttaa aactccatat gttaatgatt agatggttat attacaatca   2353
ttttatattt tttacatga ttaacattca cttatggatt catgatggct gtataaagtg    2413
aatttgaaat ttcaatggtt tactgtcatt gtgtttaaat ctcaacgttc cattatttta   2473
atacttgcaa aaacattact aagtatacca aaataattga ctctattatc tgaaatgaag   2533
aataaactga tgctatctca acaataactg ttacttttat tttataattt gataatgaat   2593
atatttctgc atttatttac ttctgttttg taaattggga ttttgttaat caaatttatt   2653
gtactatgac taaatgaaat tatttcttac atctaatttg tagaaacagt ataagttata   2713
ttaaagtgtt ttcacatttt tttgaaagac                                    2743
```

<210> SEQ ID NO 14
<211> LENGTH: 375
<212> TYPE: PRT
<213> ORGANISM: Homo sapiens

<400> SEQUENCE: 14

```
Met Gln Lys Leu Gln Leu Cys Val Tyr Ile Tyr Leu Phe Met Leu Ile
1               5                   10                  15

Val Ala Gly Pro Val Asp Leu Asn Glu Asn Ser Glu Gln Lys Glu Asn
            20                  25                  30

Val Glu Lys Glu Gly Leu Cys Asn Ala Cys Thr Trp Arg Gln Asn Thr
        35                  40                  45

Lys Ser Ser Arg Ile Glu Ala Ile Lys Ile Gln Ile Leu Ser Lys Leu
    50                  55                  60

Arg Leu Glu Thr Ala Pro Asn Ile Ser Lys Asp Val Ile Arg Gln Leu
65                  70                  75                  80

Leu Pro Lys Ala Pro Pro Leu Arg Glu Leu Ile Asp Gln Tyr Asp Val
                85                  90                  95

Gln Arg Asp Asp Ser Ser Asp Gly Ser Leu Glu Asp Asp Tyr His
            100                 105                 110

Ala Thr Thr Glu Thr Ile Ile Thr Met Pro Thr Glu Ser Asp Phe Leu
        115                 120                 125

Met Gln Val Asp Gly Lys Pro Lys Cys Cys Phe Phe Lys Phe Ser Ser
    130                 135                 140

Lys Ile Gln Tyr Asn Lys Val Val Lys Ala Gln Leu Trp Ile Tyr Leu
145                 150                 155                 160

Arg Pro Val Glu Thr Pro Thr Thr Val Phe Val Gln Ile Leu Arg Leu
                165                 170                 175
```

```
Ile Lys Pro Met Lys Asp Gly Thr Arg Tyr Thr Gly Ile Arg Ser Leu
            180                 185                 190

Lys Leu Asp Met Asn Pro Gly Thr Gly Ile Trp Gln Ser Ile Asp Val
        195                 200                 205

Lys Thr Val Leu Gln Asn Trp Leu Lys Gln Pro Glu Ser Asn Leu Gly
    210                 215                 220

Ile Glu Ile Lys Ala Leu Asp Glu Asn Gly His Asp Leu Ala Val Thr
225                 230                 235                 240

Phe Pro Gly Pro Gly Glu Asp Gly Leu Asn Pro Phe Leu Glu Val Lys
                245                 250                 255

Val Thr Asp Thr Pro Lys Arg Ser Arg Arg Asp Phe Gly Leu Asp Cys
            260                 265                 270

Asp Glu His Ser Thr Glu Ser Arg Cys Cys Arg Tyr Pro Leu Thr Val
        275                 280                 285

Asp Phe Glu Ala Phe Gly Trp Asp Trp Ile Ile Ala Pro Lys Arg Tyr
    290                 295                 300

Lys Ala Asn Tyr Cys Ser Gly Glu Cys Glu Phe Val Phe Leu Gln Lys
305                 310                 315                 320

Tyr Pro His Thr His Leu Val His Gln Ala Asn Pro Arg Gly Ser Ala
                325                 330                 335

Gly Pro Cys Cys Thr Pro Thr Lys Met Ser Pro Ile Asn Met Leu Tyr
            340                 345                 350

Phe Asn Gly Lys Glu Gln Ile Ile Tyr Gly Lys Ile Pro Ala Met Val
        355                 360                 365

Val Asp Arg Cys Gly Cys Ser
    370                 375

<210> SEQ ID NO 15
<211> LENGTH: 34
<212> TYPE: DNA
<213> ORGANISM: Artificial Sequence
<220> FEATURE:
<223> OTHER INFORMATION: Oligonucleotides for PCR

<400> SEQUENCE: 15
cgcggatccg tggatctaaa tgagaacagt gagc                          34

<210> SEQ ID NO 16
<211> LENGTH: 37
<212> TYPE: DNA
<213> ORGANISM: Artificial Sequence
<220> FEATURE:
<223> OTHER INFORMATION: Oligonucleotide for PCR

<400> SEQUENCE: 16
cgcgaattct caggtaatga ttgtttccgt tgtagcg                       37

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide for PCR

<400> SEQUENCE: 17
acactaaatc ttcaagaata                                          20

<210> SEQ ID NO 18
<211> LENGTH: 790
```

<212> TYPE: DNA
<213> ORGANISM: Gallus gallus
<220> FEATURE:
<221> NAME/KEY: CDS
<222> LOCATION: (1)..(678)
<223> OTHER INFORMATION:

<400> SEQUENCE: 18

| | | | | | | | | | | | | | | | | |
|---|---|---|---|---|---|---|---|---|---|---|---|---|---|---|---|---|
| tta | gta | gta | aag | gca | caa | tta | tgg | ata | tac | ttg | agg | caa | gtc | caa | aaa | 48 |
| Leu | Val | Val | Lys | Ala | Gln | Leu | Trp | Ile | Tyr | Leu | Arg | Gln | Val | Gln | Lys | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cct | aca | acg | gtg | ttt | gtg | cag | atc | ctg | aga | ctc | att | aag | ccc | atg | aaa | 96 |
| Pro | Thr | Thr | Val | Phe | Val | Gln | Ile | Leu | Arg | Leu | Ile | Lys | Pro | Met | Lys | |
| | | | 20 | | | | | 25 | | | | | 30 | | | |

| | | | | | | | | | | | | | | | | |
|---|---|---|---|---|---|---|---|---|---|---|---|---|---|---|---|---|
| gac | ggt | aca | aga | tat | act | gga | att | cga | tct | ttg | aaa | ctt | gac | atg | aac | 144 |
| Asp | Gly | Thr | Arg | Tyr | Thr | Gly | Ile | Arg | Ser | Leu | Lys | Leu | Asp | Met | Asn | |
| | | 35 | | | | | 40 | | | | | 45 | | | | |

| | | | | | | | | | | | | | | | | |
|---|---|---|---|---|---|---|---|---|---|---|---|---|---|---|---|---|
| cca | ggc | act | ggt | atc | tgg | cag | agt | att | gat | gtg | aag | aca | gtg | ctg | caa | 192 |
| Pro | Gly | Thr | Gly | Ile | Trp | Gln | Ser | Ile | Asp | Val | Lys | Thr | Val | Leu | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| aat | tgg | ctc | aaa | cag | cct | gaa | tcc | aat | tta | ggc | atc | gaa | ata | aaa | gct | 240 |
| Asn | Trp | Leu | Lys | Gln | Pro | Glu | Ser | Asn | Leu | Gly | Ile | Glu | Ile | Lys | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttt | gat | gag | act | gga | cga | gat | ctt | gct | gtc | aca | ttc | cca | gga | cca | gga | 288 |
| Phe | Asp | Glu | Thr | Gly | Arg | Asp | Leu | Ala | Val | Thr | Phe | Pro | Gly | Pro | Gly | |
| | | | | 85 | | | | | 90 | | | | | 95 | | |

| | | | | | | | | | | | | | | | | |
|---|---|---|---|---|---|---|---|---|---|---|---|---|---|---|---|---|
| gaa | gat | gga | ttg | aac | cca | ttt | tta | gag | gtc | aga | gtt | aca | gac | aca | ccg | 336 |
| Glu | Asp | Gly | Leu | Asn | Pro | Phe | Leu | Glu | Val | Arg | Val | Thr | Asp | Thr | Pro | |
| | | | 100 | | | | | 105 | | | | | 110 | | | |

| | | | | | | | | | | | | | | | | |
|---|---|---|---|---|---|---|---|---|---|---|---|---|---|---|---|---|
| aaa | cgg | tcc | cgc | aga | gat | ttt | ggc | ctt | gac | tgt | gat | gag | cac | tca | acg | 384 |
| Lys | Arg | Ser | Arg | Arg | Asp | Phe | Gly | Leu | Asp | Cys | Asp | Glu | His | Ser | Thr | |
| | | 115 | | | | | 120 | | | | | 125 | | | | |

| | | | | | | | | | | | | | | | | |
|---|---|---|---|---|---|---|---|---|---|---|---|---|---|---|---|---|
| gaa | tcc | cga | tgt | tgt | cgc | tac | ccg | ctg | aca | gtg | gat | ttc | gaa | gct | ttt | 432 |
| Glu | Ser | Arg | Cys | Cys | Arg | Tyr | Pro | Leu | Thr | Val | Asp | Phe | Glu | Ala | Phe | |
| | 130 | | | | | 135 | | | | | 140 | | | | | |

| | | | | | | | | | | | | | | | | |
|---|---|---|---|---|---|---|---|---|---|---|---|---|---|---|---|---|
| gga | tgg | gac | tgg | att | ata | gca | cct | aaa | aga | tac | aaa | gcc | aat | tac | tgc | 480 |
| Gly | Trp | Asp | Trp | Ile | Ile | Ala | Pro | Lys | Arg | Tyr | Lys | Ala | Asn | Tyr | Cys | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tcc | gga | gaa | tgc | gaa | ttt | gtg | ttt | cta | cag | aaa | tac | ccg | cac | act | cac | 528 |
| Ser | Gly | Glu | Cys | Glu | Phe | Val | Phe | Leu | Gln | Lys | Tyr | Pro | His | Thr | His | |
| | | | | 165 | | | | | 170 | | | | | 175 | | |

| | | | | | | | | | | | | | | | | |
|---|---|---|---|---|---|---|---|---|---|---|---|---|---|---|---|---|
| ctg | gta | cac | caa | gca | aat | ccc | aga | ggc | tca | gca | ggc | cct | tgc | tgc | aca | 576 |
| Leu | Val | His | Gln | Ala | Asn | Pro | Arg | Gly | Ser | Ala | Gly | Pro | Cys | Cys | Thr | |
| | | | 180 | | | | | 185 | | | | | 190 | | | |

| | | | | | | | | | | | | | | | | |
|---|---|---|---|---|---|---|---|---|---|---|---|---|---|---|---|---|
| ccc | acc | aag | atg | tcc | cct | ata | aac | atg | ctg | tat | ttc | aat | gga | aaa | gaa | 624 |
| Pro | Thr | Lys | Met | Ser | Pro | Ile | Asn | Met | Leu | Tyr | Phe | Asn | Gly | Lys | Glu | |
| | | 195 | | | | | 200 | | | | | 205 | | | | |

| | | | | | | | | | | | | | | | | |
|---|---|---|---|---|---|---|---|---|---|---|---|---|---|---|---|---|
| caa | ata | ata | tat | gga | aag | ata | cca | gcc | atg | gtt | gta | gat | cgt | tgc | ggg | 672 |
| Gln | Ile | Ile | Tyr | Gly | Lys | Ile | Pro | Ala | Met | Val | Val | Asp | Arg | Cys | Gly | |
| | 210 | | | | | 215 | | | | | 220 | | | | | |

| | | | | | |
|---|---|---|---|---|---|
| tgc | tca | tgaggctgtc gtgagatcca ccattcgata aattgtggaa gccaccaaaa | | | 728 |
| Cys | Ser | | | | |
| 225 | | | | | | aaaaaagcta tatcccctca tccatctttg aaactgtgaa attacgtacg ctaggcattg   788 cc   790

<210> SEQ ID NO 19
<211> LENGTH: 226
<212> TYPE: PRT
<213> ORGANISM: Gallus gallus

<400> SEQUENCE: 19

```
Leu Val Val Lys Ala Gln Leu Trp Ile Tyr Leu Arg Gln Val Gln Lys
1               5                   10                  15
Pro Thr Thr Val Phe Val Gln Ile Leu Arg Leu Ile Lys Pro Met Lys
                20                  25                  30
Asp Gly Thr Arg Tyr Thr Gly Ile Arg Ser Leu Lys Leu Asp Met Asn
            35                  40                  45
Pro Gly Thr Gly Ile Trp Gln Ser Ile Asp Val Lys Thr Val Leu Gln
        50                  55                  60
Asn Trp Leu Lys Gln Pro Glu Ser Asn Leu Gly Ile Glu Ile Lys Ala
65                  70                  75                  80
Phe Asp Glu Thr Gly Arg Asp Leu Ala Val Thr Phe Pro Gly Pro Gly
                85                  90                  95
Glu Asp Gly Leu Asn Pro Phe Leu Glu Val Arg Val Thr Asp Thr Pro
            100                 105                 110
Lys Arg Ser Arg Arg Asp Phe Gly Leu Asp Cys Asp Glu His Ser Thr
        115                 120                 125
Glu Ser Arg Cys Cys Arg Tyr Pro Leu Thr Val Asp Phe Glu Ala Phe
130                 135                 140
Gly Trp Asp Trp Ile Ile Ala Pro Lys Arg Tyr Lys Ala Asn Tyr Cys
145                 150                 155                 160
Ser Gly Glu Cys Glu Phe Val Phe Leu Gln Lys Tyr Pro His Thr His
                165                 170                 175
Leu Val His Gln Ala Asn Pro Arg Gly Ser Ala Gly Pro Cys Cys Thr
            180                 185                 190
Pro Thr Lys Met Ser Pro Ile Asn Met Leu Tyr Phe Asn Gly Lys Glu
        195                 200                 205
Gln Ile Ile Tyr Gly Lys Ile Pro Ala Met Val Val Asp Arg Cys Gly
        210                 215                 220
Cys Ser
225
```

```
<210> SEQ ID NO 20
<211> LENGTH: 480
<212> TYPE: DNA
<213> ORGANISM: Rattus norvegicus
<220> FEATURE:
<221> NAME/KEY: CDS
<222> LOCATION: (1)..(390)
<223> OTHER INFORMATION:
```

<400> SEQUENCE: 20

```
gaa gat ggg ctg aat ccc ttt tta gaa gtc aaa gta aca gac aca ccc      48
Glu Asp Gly Leu Asn Pro Phe Leu Glu Val Lys Val Thr Asp Thr Pro
1               5                   10                  15 aag agg tcc cgg aga gac ttt ggg ctt gac tgc gat gaa cac tcc acg      96
Lys Arg Ser Arg Arg Asp Phe Gly Leu Asp Cys Asp Glu His Ser Thr
                20                  25                  30 gaa tcg cgg tgc tgt cgc tac ccc ctc acg gtc gat ttc gaa gcc ttt     144
Glu Ser Arg Cys Cys Arg Tyr Pro Leu Thr Val Asp Phe Glu Ala Phe
            35                  40                  45 gga tgg gac tgg att att gca ccc aaa aga tat aag gct aat tac tgc     192
Gly Trp Asp Trp Ile Ile Ala Pro Lys Arg Tyr Lys Ala Asn Tyr Cys
        50                  55                  60 tct gga gag tgt gaa ttt gtg ttc tta caa aaa tat ccg cat act cat     240
Ser Gly Glu Cys Glu Phe Val Phe Leu Gln Lys Tyr Pro His Thr His
65                  70                  75                  80
```

```
ctt gtg cac caa gca aac ccc aga ggc tcg gca ggc cct tgc tgc acg       288
Leu Val His Gln Ala Asn Pro Arg Gly Ser Ala Gly Pro Cys Cys Thr
             85                  90                  95 cca aca aaa atg tct ccc att aat atg cta tat ttt aat ggc aaa gaa       336
Pro Thr Lys Met Ser Pro Ile Asn Met Leu Tyr Phe Asn Gly Lys Glu
            100                 105                 110 caa ata ata tat ggg aaa att cca gcc atg gta gta gac cgg tgt ggg       384
Gln Ile Ile Tyr Gly Lys Ile Pro Ala Met Val Val Asp Arg Cys Gly
            115                 120                 125 tgc tcg tgagctttgc attagcttta aaatttccca atcgtggaa ggtcttcccc         440
Cys Ser
    130 tcgatttcga aactgtgaat ttatgtacca caggctgtag                           480
```

<210> SEQ ID NO 21
<211> LENGTH: 130
<212> TYPE: PRT
<213> ORGANISM: Rattus norvegicus

<400> SEQUENCE: 21

```
Glu Asp Gly Leu Asn Pro Phe Leu Glu Val Lys Val Thr Asp Thr Pro
1               5                   10                  15

Lys Arg Ser Arg Arg Asp Phe Gly Leu Asp Cys Asp Glu His Ser Thr
            20                  25                  30

Glu Ser Arg Cys Cys Arg Tyr Pro Leu Thr Val Asp Phe Glu Ala Phe
        35                  40                  45

Gly Trp Asp Trp Ile Ile Ala Pro Lys Arg Tyr Lys Ala Asn Tyr Cys
    50                  55                  60

Ser Gly Glu Cys Glu Phe Val Phe Leu Gln Lys Tyr Pro His Thr His
65                  70                  75                  80

Leu Val His Gln Ala Asn Pro Arg Gly Ser Ala Gly Pro Cys Cys Thr
                85                  90                  95

Pro Thr Lys Met Ser Pro Ile Asn Met Leu Tyr Phe Asn Gly Lys Glu
            100                 105                 110

Gln Ile Ile Tyr Gly Lys Ile Pro Ala Met Val Val Asp Arg Cys Gly
            115                 120                 125

Cys Ser
    130
```

<210> SEQ ID NO 22
<211> LENGTH: 123
<212> TYPE: PRT
<213> ORGANISM: Homo sapiens

<400> SEQUENCE: 22

```
Arg Pro Arg Arg Asp Ala Glu Pro Val Leu Gly Gly Pro Gly Gly Gly
1               5                   10                  15

Ala Cys Arg Ala Arg Arg Leu Tyr Val Ser Phe Arg Glu Val Gly Trp
            20                  25                  30

His Arg Trp Val Ile Ala Pro Arg Gly Phe Leu Ala Asn Tyr Cys Gln
        35                  40                  45

Gly Gln Cys Ala Leu Pro Val Ala Leu Ser Gly Ser Gly Gly Pro Pro
    50                  55                  60

Ala Leu Asn His Ala Val Leu Arg Ala Leu Met His Ala Ala Ala Pro
65                  70                  75                  80

Gly Ala Ala Asp Leu Pro Cys Cys Val Pro Ala Arg Leu Ser Pro Ile
                85                  90                  95
```

```
Ser Val Leu Phe Phe Asp Asn Ser Asp Asn Val Val Leu Arg Gln Tyr
            100                 105                 110

Glu Asp Met Val Val Asp Glu Cys Gly Cys Arg
        115                 120

<210> SEQ ID NO 23
<211> LENGTH: 118
<212> TYPE: PRT
<213> ORGANISM: Homo sapiens

<400> SEQUENCE: 23

Arg Glu Lys Arg Gln Ala Lys His Lys Gln Arg Lys Arg Leu Lys Ser
1               5                   10                  15

Ser Cys Lys Arg His Pro Leu Tyr Val Asp Phe Ser Asp Val Gly Trp
            20                  25                  30

Asn Asp Trp Ile Val Ala Pro Pro Gly Tyr His Ala Phe Tyr Cys His
        35                  40                  45

Gly Glu Cys Pro Phe Pro Leu Ala Asp His Leu Asn Ser Thr Asn His
    50                  55                  60

Ala Ile Val Gln Thr Leu Val Asn Ser Val Asn Ser Lys Ile Pro Lys
65                  70                  75                  80

Ala Cys Cys Val Pro Thr Glu Leu Ser Ala Ile Ser Met Leu Tyr Leu
                85                  90                  95

Asp Glu Asn Glu Lys Val Val Leu Lys Asn Tyr Gln Asp Met Val Val
            100                 105                 110

Glu Gly Cys Gly Cys Arg
        115

<210> SEQ ID NO 24
<211> LENGTH: 118
<212> TYPE: PRT
<213> ORGANISM: Homo sapiens

<400> SEQUENCE: 24

Lys Arg Ser Pro Lys His His Ser Gln Arg Ala Arg Lys Lys Asn Lys
1               5                   10                  15

Asn Cys Arg Arg His Ser Leu Tyr Val Asp Phe Ser Asp Val Gly Trp
            20                  25                  30

Asn Asp Trp Ile Val Ala Pro Pro Gly Tyr Gln Ala Phe Tyr Cys His
        35                  40                  45

Gly Asp Cys Pro Phe Pro Leu Ala Asp His Leu Asn Ser Thr Asn His
    50                  55                  60

Ala Ile Val Gln Thr Leu Val Asn Ser Val Asn Ser Ser Ile Pro Lys
65                  70                  75                  80

Ala Cys Cys Val Pro Thr Glu Leu Ser Ala Ile Ser Met Leu Tyr Leu
                85                  90                  95

Asp Glu Tyr Asp Lys Val Val Leu Lys Asn Tyr Gln Glu Met Val Val
            100                 105                 110

Glu Gly Cys Gly Cys Arg
        115

<210> SEQ ID NO 25
<211> LENGTH: 119
<212> TYPE: PRT
<213> ORGANISM: Homo sapiens

<400> SEQUENCE: 25

Ser Arg Gly Ser Gly Ser Ser Asp Tyr Asn Gly Ser Glu Leu Lys Thr
```

-continued

```
                1               5                   10                  15
Ala Cys Lys Lys His Glu Leu Tyr Val Ser Phe Gln Asp Leu Gly Trp
                20                  25                  30

Gln Asp Trp Ile Ile Ala Pro Lys Gly Tyr Ala Ala Asn Tyr Cys Asp
            35                  40                  45

Gly Glu Cys Ser Phe Pro Leu Asn Ala His Met Asn Ala Thr Asn His
        50                  55                  60

Ala Ile Val Gln Thr Leu Val His Leu Met Asn Pro Glu Tyr Val Pro
65                  70                  75                  80

Lys Pro Cys Cys Ala Pro Thr Lys Leu Asn Ala Ile Ser Val Leu Tyr
                85                  90                  95

Phe Asp Asp Asn Ser Asn Val Ile Leu Lys Lys Tyr Arg Asn Met Val
                100                 105                 110

Val Arg Ala Cys Gly Cys His
                115

<210> SEQ ID NO 26
<211> LENGTH: 119
<212> TYPE: PRT
<213> ORGANISM: Homo sapiens

<400> SEQUENCE: 26

Leu Arg Met Ala Asn Val Ala Glu Asn Ser Ser Asp Gln Arg Gln
1               5                   10                  15

Ala Cys Lys Lys His Glu Leu Tyr Val Ser Phe Arg Asp Leu Gly Trp
                20                  25                  30

Gln Asp Trp Ile Ile Ala Pro Glu Gly Tyr Ala Ala Tyr Tyr Cys Glu
            35                  40                  45

Gly Glu Cys Ala Phe Pro Leu Asn Ser Tyr Met Asn Ala Thr Asn His
        50                  55                  60

Ala Ile Val Gln Thr Leu Val His Phe Ile Asn Pro Glu Thr Val Pro
65                  70                  75                  80

Lys Pro Cys Cys Ala Pro Thr Gln Leu Asn Ala Ile Ser Val Leu Tyr
                85                  90                  95

Phe Asp Asp Ser Ser Asn Val Ile Leu Lys Lys Tyr Arg Asn Met Val
                100                 105                 110

Val Arg Ala Cys Gly Cys His
                115

<210> SEQ ID NO 27
<211> LENGTH: 119
<212> TYPE: PRT
<213> ORGANISM: Homo sapiens

<400> SEQUENCE: 27

Ser Arg Met Ser Ser Val Gly Asp Tyr Asn Thr Ser Glu Gln Lys Gln
1               5                   10                  15

Ala Cys Lys Lys His Glu Leu Tyr Val Ser Phe Arg Asp Leu Gly Trp
                20                  25                  30

Gln Asp Trp Ile Ile Ala Pro Glu Gly Tyr Ala Ala Phe Tyr Cys Asp
            35                  40                  45

Gly Glu Cys Ser Phe Pro Leu Asn Ala His Met Asn Ala Thr Asn His
        50                  55                  60

Ala Ile Val Gln Thr Leu Val His Leu Met Phe Pro Asp His Val Pro
65                  70                  75                  80

Lys Pro Cys Cys Ala Pro Thr Lys Leu Asn Ala Ile Ser Val Leu Tyr
```

```
                  85                  90                  95
Phe Asp Asp Ser Ser Asn Val Ile Leu Lys Lys Tyr Arg Asn Met Val
            100                 105                 110

Val Arg Ser Cys Gly Cys His
        115

<210> SEQ ID NO 28
<211> LENGTH: 1125
<212> TYPE: DNA
<213> ORGANISM: Danio Rerio
<220> FEATURE:
<221> NAME/KEY: CDS
<222> LOCATION: (1)..(1122)
<223> OTHER INFORMATION:

<400> SEQUENCE: 28 atg cat ttt aca cag gtt tta att tct cta agt gta tta att gca tgt        48
Met His Phe Thr Gln Val Leu Ile Ser Leu Ser Val Leu Ile Ala Cys
1               5                  10                  15 ggt cca gtg ggt tat gga gat ata acg gcg cac cag cag cct tcc aca        96
Gly Pro Val Gly Tyr Gly Asp Ile Thr Ala His Gln Gln Pro Ser Thr
            20                  25                  30 gcc acg gag gaa agc gag ctg tgt tcc aca tgt gag ttc aga caa cac       144
Ala Thr Glu Glu Ser Glu Leu Cys Ser Thr Cys Glu Phe Arg Gln His
        35                  40                  45 agc aag ctg atg aga ctg cat gcc atc aag tcc caa att ctt agc aaa       192
Ser Lys Leu Met Arg Leu His Ala Ile Lys Ser Gln Ile Leu Ser Lys
    50                  55                  60 ctc cga ctc aag cag gct cca aac atc agc cgg gac gtg gtc aag cag       240
Leu Arg Leu Lys Gln Ala Pro Asn Ile Ser Arg Asp Val Val Lys Gln
65                  70                  75                  80 ctg tta ccc aaa gca ccg cct ttg caa caa ctt ctg gat cag tac gat       288
Leu Leu Pro Lys Ala Pro Pro Leu Gln Gln Leu Leu Asp Gln Tyr Asp
                85                  90                  95 gtt tta gga gat gac agt aag gat gga gct gtg gaa gag gac gat gaa       336
Val Leu Gly Asp Asp Ser Lys Asp Gly Ala Val Glu Glu Asp Asp Glu
            100                 105                 110 cat gcc acc aca gag acc atc atg acc atg gcc aca gaa cct gac ccc       384
His Ala Thr Thr Glu Thr Ile Met Thr Met Ala Thr Glu Pro Asp Pro
        115                 120                 125 att gtt caa gta gat cgg aaa ccg aag tgt tgc ttt ttc tcc ttc agt       432
Ile Val Gln Val Asp Arg Lys Pro Lys Cys Cys Phe Phe Ser Phe Ser
    130                 135                 140 ccg aag atc caa gcg aac cgg atc gta aga gcg cag ctc tgg gtt cat       480
Pro Lys Ile Gln Ala Asn Arg Ile Val Arg Ala Gln Leu Trp Val His
145                 150                 155                 160 ctg aga ccg gcg gag gag gcg acc acc gtc ttc tta cag ata tct cgg       528
Leu Arg Pro Ala Glu Glu Ala Thr Thr Val Phe Leu Gln Ile Ser Arg
                165                 170                 175 ctg atg ccc gtt aag gac gga gga aga cac cga ata cga tcc ctg aaa       576
Leu Met Pro Val Lys Asp Gly Gly Arg His Arg Ile Arg Ser Leu Lys
            180                 185                 190 atc gac gtg aac gca gga gtc acg tct tgg cag agt ata gac gta aag       624
Ile Asp Val Asn Ala Gly Val Thr Ser Trp Gln Ser Ile Asp Val Lys
        195                 200                 205 cag gtg ctc acg gtg tgg tta aaa caa ccg gag acc aac cga ggc atc       672
Gln Val Leu Thr Val Trp Leu Lys Gln Pro Glu Thr Asn Arg Gly Ile
    210                 215                 220 gag att aac gca tat gac gcg aag gga aac gac ttg gcc gtc act tca       720
Glu Ile Asn Ala Tyr Asp Ala Lys Gly Asn Asp Leu Ala Val Thr Ser
225                 230                 235                 240
```

```
acc gag act ggg gag gat gga ctg ctc ccc ttt atg gag gtg aaa ata      768
Thr Glu Thr Gly Glu Asp Gly Leu Leu Pro Phe Met Glu Val Lys Ile
                245                 250                 255 tca gag ggc cca aaa cga atc cgg agg gac tcc gga ctg gac tgc gat      816
Ser Glu Gly Pro Lys Arg Ile Arg Arg Asp Ser Gly Leu Asp Cys Asp
            260                 265                 270 gag aat tcc tca gag tct cgc tgc tgc agg tac cct ctc act gtg gac      864
Glu Asn Ser Ser Glu Ser Arg Cys Cys Arg Tyr Pro Leu Thr Val Asp
        275                 280                 285 ttc gag gac ttt ggc tgg gac tgg att att gct cca aaa cgc tat aag      912
Phe Glu Asp Phe Gly Trp Asp Trp Ile Ile Ala Pro Lys Arg Tyr Lys
    290                 295                 300 gcg aat tac tgt tca gga gaa tgc gac tac atg tac ctg cag aag tat      960
Ala Asn Tyr Cys Ser Gly Glu Cys Asp Tyr Met Tyr Leu Gln Lys Tyr
305                 310                 315                 320 ccc cac acc cat ctg gtg aac aag gcc agt ccg aga gga acg gct ggg     1008
Pro His Thr His Leu Val Asn Lys Ala Ser Pro Arg Gly Thr Ala Gly
                325                 330                 335 ccc tgc tgc act ccc acc aag atg tct ccc atc aac atg ctt tac ttt     1056
Pro Cys Cys Thr Pro Thr Lys Met Ser Pro Ile Asn Met Leu Tyr Phe
            340                 345                 350 aac ggc aaa gag cag atc atc tac ggc aag atc cct tcg atg gta gta     1104
Asn Gly Lys Glu Gln Ile Ile Tyr Gly Lys Ile Pro Ser Met Val Val
        355                 360                 365 gac cgc tgt ggc tgc tca tga                                         1125
Asp Arg Cys Gly Cys Ser
        370

<210> SEQ ID NO 29
<211> LENGTH: 374
<212> TYPE: PRT
<213> ORGANISM: Danio Rerio

<400> SEQUENCE: 29

Met His Phe Thr Gln Val Leu Ile Ser Leu Ser Val Leu Ile Ala Cys
1               5                   10                  15

Gly Pro Val Gly Tyr Gly Asp Ile Thr Ala His Gln Gln Pro Ser Thr
            20                  25                  30

Ala Thr Glu Glu Ser Glu Leu Cys Ser Thr Cys Glu Phe Arg Gln His
        35                  40                  45

Ser Lys Leu Met Arg Leu His Ala Ile Lys Ser Gln Ile Leu Ser Lys
    50                  55                  60

Leu Arg Leu Lys Gln Ala Pro Asn Ile Ser Arg Asp Val Val Lys Gln
65                  70                  75                  80

Leu Leu Pro Lys Ala Pro Pro Leu Gln Gln Leu Leu Asp Gln Tyr Asp
                85                  90                  95

Val Leu Gly Asp Asp Ser Lys Asp Gly Ala Val Glu Glu Asp Asp Glu
            100                 105                 110

His Ala Thr Thr Glu Thr Ile Met Thr Met Ala Thr Glu Pro Asp Pro
        115                 120                 125

Ile Val Gln Val Asp Arg Lys Pro Lys Cys Cys Phe Phe Ser Phe Ser
    130                 135                 140

Pro Lys Ile Gln Ala Asn Arg Ile Val Arg Ala Gln Leu Trp Val His
145                 150                 155                 160

Leu Arg Pro Ala Glu Glu Ala Thr Thr Val Phe Leu Gln Ile Ser Arg
                165                 170                 175

Leu Met Pro Val Lys Asp Gly Gly Arg His Arg Ile Arg Ser Leu Lys
```

-continued

```
                        180                 185                 190
Ile Asp Val Asn Ala Gly Val Thr Ser Trp Gln Ser Ile Asp Val Lys
            195                 200                 205
Gln Val Leu Thr Val Trp Leu Lys Gln Pro Glu Thr Asn Arg Gly Ile
        210                 215                 220
Glu Ile Asn Ala Tyr Asp Ala Lys Gly Asn Asp Leu Ala Val Thr Ser
225                 230                 235                 240
Thr Glu Thr Gly Glu Asp Gly Leu Leu Pro Phe Met Glu Val Lys Ile
                245                 250                 255
Ser Glu Gly Pro Lys Arg Ile Arg Arg Asp Ser Gly Leu Asp Cys Asp
            260                 265                 270
Glu Asn Ser Ser Glu Ser Arg Cys Cys Arg Tyr Pro Leu Thr Val Asp
        275                 280                 285
Phe Glu Asp Phe Gly Trp Asp Trp Ile Ile Ala Pro Lys Arg Tyr Lys
    290                 295                 300
Ala Asn Tyr Cys Ser Gly Glu Cys Asp Tyr Met Tyr Leu Gln Lys Tyr
305                 310                 315                 320
Pro His Thr His Leu Val Asn Lys Ala Ser Pro Arg Gly Thr Ala Gly
                325                 330                 335
Pro Cys Cys Thr Pro Thr Lys Met Ser Pro Ile Asn Met Leu Tyr Phe
            340                 345                 350
Asn Gly Lys Glu Gln Ile Ile Tyr Gly Lys Ile Pro Ser Met Val Val
        355                 360                 365
Asp Arg Cys Gly Cys Ser
    370

<210> SEQ ID NO 30
<211> LENGTH: 476
<212> TYPE: DNA
<213> ORGANISM: Piscine
<220> FEATURE:
<221> NAME/KEY: CDS
<222> LOCATION: (3)..(473)
<223> OTHER INFORMATION:

<400> SEQUENCE: 30 gg cag ccg gag acg aat tgg ggg atc gag att aat gcg ttc gac tcg        47
   Gln Pro Glu Thr Asn Trp Gly Ile Glu Ile Asn Ala Phe Asp Ser
    1               5                  10                  15 aag gga aat gat ctg gcc gtt acc tca gca gaa gcg gga gaa gga ctg       95
Lys Gly Asn Asp Leu Ala Val Thr Ser Ala Glu Ala Gly Glu Gly Leu
                20                  25                  30 caa ccc ttc atg gag gtg acg att tca gag ggc ccg aag cgc tcc agg      143
Gln Pro Phe Met Glu Val Thr Ile Ser Glu Gly Pro Lys Arg Ser Arg
            35                  40                  45 aga gac tcg ggc ctg gac tgt gac gag aac tcc ccc gag tcc cgc tgt      191
Arg Asp Ser Gly Leu Asp Cys Asp Glu Asn Ser Pro Glu Ser Arg Cys
        50                  55                  60 tgc cgc tac ccc ctc acg gta gac ttt gaa gac ttt ggc tgg gac tgg      239
Cys Arg Tyr Pro Leu Thr Val Asp Phe Glu Asp Phe Gly Trp Asp Trp
65                  70                  75 att att gcc ccc aag cgc tac aag gcc aac tac tgc tct ggt gag tgt      287
Ile Ile Ala Pro Lys Arg Tyr Lys Ala Asn Tyr Cys Ser Gly Glu Cys
80                  85                  90                  95 gag tac atg cac ctg cag aag tac ccc cac acc cac ctg gtg aac aag      335
Glu Tyr Met His Leu Gln Lys Tyr Pro His Thr His Leu Val Asn Lys
                100                 105                 110 gct aac cct cgc ggc acc gca ggg ccc tgc tgc acc ccc acc aag atg      383
Ala Asn Pro Arg Gly Thr Ala Gly Pro Cys Cys Thr Pro Thr Lys Met
```

```
Ala Asn Pro Arg Gly Thr Ala Gly Pro Cys Cys Thr Pro Thr Lys Met
            115                 120                 125 tcc ccc atc aac atg ctc tac ttc aac cgc aaa gag cag atc atc tac      431
Ser Pro Ile Asn Met Leu Tyr Phe Asn Arg Lys Glu Gln Ile Ile Tyr
        130                 135                 140 ggc aag atc ccc tcc atg gtg gtg gac cgt tgc gga tgc tcg tga          476
Gly Lys Ile Pro Ser Met Val Val Asp Arg Cys Gly Cys Ser
145                 150                 155

<210> SEQ ID NO 31
<211> LENGTH: 157
<212> TYPE: PRT
<213> ORGANISM: Piscine

<400> SEQUENCE: 31

Gln Pro Glu Thr Asn Trp Gly Ile Glu Ile Asn Ala Phe Asp Ser Lys
1               5                   10                  15

Gly Asn Asp Leu Ala Val Thr Ser Ala Glu Ala Gly Glu Gly Leu Gln
            20                  25                  30

Pro Phe Met Glu Val Thr Ile Ser Glu Gly Pro Lys Arg Ser Arg Arg
        35                  40                  45

Asp Ser Gly Leu Asp Cys Asp Glu Asn Ser Pro Glu Ser Arg Cys Cys
    50                  55                  60

Arg Tyr Pro Leu Thr Val Asp Phe Glu Asp Phe Gly Trp Asp Trp Ile
65                  70                  75                  80

Ile Ala Pro Lys Arg Tyr Lys Ala Asn Tyr Cys Ser Gly Glu Cys Glu
                85                  90                  95

Tyr Met His Leu Gln Lys Tyr Pro His Thr His Leu Val Asn Lys Ala
            100                 105                 110

Asn Pro Arg Gly Thr Ala Gly Pro Cys Cys Thr Pro Thr Lys Met Ser
        115                 120                 125

Pro Ile Asn Met Leu Tyr Phe Asn Arg Lys Glu Gln Ile Ile Tyr Gly
    130                 135                 140

Lys Ile Pro Ser Met Val Val Asp Arg Cys Gly Cys Ser
145                 150                 155

<210> SEQ ID NO 32
<211> LENGTH: 412
<212> TYPE: DNA
<213> ORGANISM: Piscine
<220> FEATURE:
<221> NAME/KEY: CDS
<222> LOCATION: (2)..(409)
<223> OTHER INFORMATION:

<400> SEQUENCE: 32 g gtt acc tca act gaa gcc gga gaa gga ctg caa ccc ttc atg gag gtg    49
  Val Thr Ser Thr Glu Ala Gly Glu Gly Leu Gln Pro Phe Met Glu Val
  1               5                   10                  15 aag att tcg gag ggc ccg aag cgc tcc agg aga gat tcg ggc ctg gac      97
Lys Ile Ser Glu Gly Pro Lys Arg Ser Arg Arg Asp Ser Gly Leu Asp
            20                  25                  30 tgt gat gag aac tcc ccc gag tcc cgc tgc tgc cgg tac ccc ctc acg      145
Cys Asp Glu Asn Ser Pro Glu Ser Arg Cys Cys Arg Tyr Pro Leu Thr
        35                  40                  45 gtg gac ttt gaa gac ttt ggc tgg gac tgg att att gcc ccc aag cgc      193
Val Asp Phe Glu Asp Phe Gly Trp Asp Trp Ile Ile Ala Pro Lys Arg
    50                  55                  60 tac aag gcc aac tac tgc tct ggt gag tgc gag tac atg cac ctg cag      241
Tyr Lys Ala Asn Tyr Cys Ser Gly Glu Cys Glu Tyr Met His Leu Gln
```

```
                    65                  70                  75                  80
aag tac ccc cac acc cac ctg gtg aac aag gct aac cct cgc ggc acc              289
Lys Tyr Pro His Thr His Leu Val Asn Lys Ala Asn Pro Arg Gly Thr
                85                  90                  95 gcg ggg ccc tgc tgc acc ccc acc aag atg tcc ccc atc aac atg ctc              337
Ala Gly Pro Cys Cys Thr Pro Thr Lys Met Ser Pro Ile Asn Met Leu
            100                 105                 110 tac ttc aac cgc aaa gag cag atc atc tac ggc aag atc ccc tcc atg              385
Tyr Phe Asn Arg Lys Glu Gln Ile Ile Tyr Gly Lys Ile Pro Ser Met
        115                 120                 125 gtg gtg gac cgc tgc ggc tgc tcg tga                                          412
Val Val Asp Arg Cys Gly Cys Ser
    130                 135

<210> SEQ ID NO 33
<211> LENGTH: 136
<212> TYPE: PRT
<213> ORGANISM: Piscine

<400> SEQUENCE: 33

Val Thr Ser Thr Glu Ala Gly Glu Gly Leu Gln Pro Phe Met Glu Val
1               5                   10                  15

Lys Ile Ser Glu Gly Pro Lys Arg Ser Arg Arg Asp Ser Gly Leu Asp
            20                  25                  30

Cys Asp Glu Asn Ser Pro Glu Ser Arg Cys Cys Arg Tyr Pro Leu Thr
        35                  40                  45

Val Asp Phe Glu Asp Phe Gly Trp Asp Trp Ile Ile Ala Pro Lys Arg
    50                  55                  60

Tyr Lys Ala Asn Tyr Cys Ser Gly Glu Cys Glu Tyr Met His Leu Gln
65                  70                  75                  80

Lys Tyr Pro His Thr His Leu Val Asn Lys Ala Asn Pro Arg Gly Thr
                85                  90                  95

Ala Gly Pro Cys Cys Thr Pro Thr Lys Met Ser Pro Ile Asn Met Leu
            100                 105                 110

Tyr Phe Asn Arg Lys Glu Gln Ile Ile Tyr Gly Lys Ile Pro Ser Met
        115                 120                 125

Val Val Asp Arg Cys Gly Cys Ser
    130                 135

<210> SEQ ID NO 34
<211> LENGTH: 120
<212> TYPE: PRT
<213> ORGANISM: Homo sapiens

<400> SEQUENCE: 34

Glu Gln Thr Leu Lys Lys Ala Arg Arg Lys Gln Trp Ile Glu Pro Arg
1               5                   10                  15

Asn Cys Ala Arg Arg Tyr Leu Lys Val Asp Phe Ala Asp Ile Gly Trp
            20                  25                  30

Ser Glu Trp Ile Ile Ser Pro Lys Ser Phe Asp Ala Tyr Tyr Cys Ser
        35                  40                  45

Gly Ala Cys Gln Phe Pro Met Pro Lys Ser Leu Lys Pro Ser Asn His
    50                  55                  60

Ala Thr Ile Gln Ser Ile Val Arg Ala Val Gly Val Val Pro Gly Ile
65                  70                  75                  80

Pro Glu Pro Cys Cys Val Pro Glu Lys Met Ser Ser Leu Ser Ile Leu
                85                  90                  95
```

Phe Phe Asp Glu Asn Lys Asn Val Val Leu Lys Val Tyr Pro Asn Met
            100                 105                 110

Thr Val Glu Ser Cys Ala Cys Arg
        115                 120

<210> SEQ ID NO 35
<211> LENGTH: 116
<212> TYPE: PRT
<213> ORGANISM: Homo sapiens

<400> SEQUENCE: 35

Gly Pro Gly Arg Ala Gln Arg Ser Ala Gly Thr Ala Ala Asp Gly
1               5                   10                  15

Pro Cys Ala Leu Arg Glu Leu Ser Val Asp Leu Arg Ala Glu Arg Ser
                20                  25                  30

Val Leu Ile Pro Glu Thr Tyr Gln Ala Asn Asn Cys Gln Gly Val Cys
            35                  40                  45

Gly Trp Pro Gln Ser Asp Arg Asn Pro Arg Tyr Gly Asn His Val Val
        50                  55                  60

Leu Leu Leu Lys Met Gln Ala Arg Gly Ala Ala Leu Ala Arg Pro Pro
65                  70                  75                  80

Cys Cys Val Pro Thr Ala Tyr Ala Gly Lys Leu Leu Ile Ser Leu Ser
                85                  90                  95

Glu Glu Arg Ile Ser Ala His His Val Pro Asn Met Val Ala Thr Glu
                100                 105                 110

Cys Gly Cys Arg
        115

<210> SEQ ID NO 36
<211> LENGTH: 122
<212> TYPE: PRT
<213> ORGANISM: Homo sapiens

<400> SEQUENCE: 36

Ala Leu Arg Leu Leu Gln Arg Pro Pro Glu Glu Pro Ala Ala His Ala
1               5                   10                  15

Asn Cys His Arg Val Ala Leu Asn Ile Ser Phe Gln Glu Leu Gly Trp
                20                  25                  30

Glu Arg Trp Ile Val Tyr Pro Pro Ser Phe Ile Phe His Tyr Cys His
            35                  40                  45

Gly Gly Cys Gly Leu His Ile Pro Pro Asn Leu Ser Leu Pro Val Pro
        50                  55                  60

Gly Ala Pro Pro Thr Pro Ala Gln Pro Tyr Ser Leu Leu Pro Gly Ala
65                  70                  75                  80

Gln Pro Cys Cys Ala Ala Leu Pro Gly Thr Met Arg Pro Leu His Val
                85                  90                  95

Arg Thr Thr Ser Asp Gly Gly Tyr Ser Phe Lys Tyr Gly Thr Val Pro
                100                 105                 110

Asn Leu Leu Thr Gln His Cys Ala Cys Ile
            115                 120

<210> SEQ ID NO 37
<211> LENGTH: 122
<212> TYPE: PRT
<213> ORGANISM: Homo sapiens

<400> SEQUENCE: 37

His Arg Arg Arg Arg Arg Gly Leu Glu Cys Asp Gly Lys Val Asn Ile

```
              1               5              10              15

Cys Cys Lys Lys Gln Phe Phe Val Ser Phe Lys Asp Ile Gly Trp Asn
                    20                  25                  30

Asp Trp Ile Ile Ala Pro Ser Gly Tyr His Ala Asn Tyr Cys Glu Gly
                    35                  40                  45

Glu Cys Pro Ser His Ile Ala Gly Thr Ser Gly Ser Ser Leu Ser Phe
                50                  55                  60

His Ser Thr Val Ile Asn His Tyr Arg Met Arg Gly His Ser Pro Phe
65                  70                  75                  80

Ala Asn Leu Lys Ser Cys Cys Val Pro Thr Lys Leu Arg Pro Met Ser
                    85                  90                  95

Met Leu Tyr Tyr Asp Asp Gly Gln Asn Ile Ile Lys Lys Asp Ile Gln
                    100                 105                 110

Asn Met Ile Val Glu Glu Cys Gly Cys Ser
                    115                 120

<210> SEQ ID NO 38
<211> LENGTH: 121
<212> TYPE: PRT
<213> ORGANISM: Homo sapiens

<400> SEQUENCE: 38

His Arg Ile Arg Lys Arg Gly Leu Glu Cys Asp Gly Arg Thr Asn Leu
1               5                   10                  15

Cys Cys Arg Gln Gln Phe Phe Ile Asp Phe Arg Leu Ile Gly Trp Asn
                    20                  25                  30

Asp Trp Ile Ile Ala Pro Thr Gly Tyr Tyr Gly Asn Tyr Cys Glu Gly
                    35                  40                  45

Ser Cys Pro Ala Tyr Leu Ala Gly Val Pro Gly Ser Ala Ser Ser Phe
                50                  55                  60

His Thr Ala Val Val Asn Gln Tyr Arg Met Arg Gly Leu Asn Pro Gly
65                  70                  75                  80

Thr Val Asn Ser Cys Cys Ile Pro Thr Lys Leu Ser Thr Met Ser Met
                    85                  90                  95

Leu Tyr Phe Asp Asp Glu Tyr Asn Ile Val Lys Arg Asp Val Pro Asn
                    100                 105                 110

Met Ile Val Glu Glu Cys Gly Cys Ala
                    115                 120

<210> SEQ ID NO 39
<211> LENGTH: 115
<212> TYPE: PRT
<213> ORGANISM: Homo sapiens

<400> SEQUENCE: 39

His Arg Arg Ala Leu Asp Thr Asn Tyr Cys Phe Ser Ser Thr Glu Lys
1               5                   10                  15

Asn Cys Cys Val Arg Gln Leu Tyr Ile Asp Phe Arg Lys Asp Leu Gly
                    20                  25                  30

Trp Lys Trp Ile His Glu Pro Lys Gly Tyr His Ala Asn Phe Cys Leu
                    35                  40                  45

Gly Pro Cys Pro Tyr Ile Trp Ser Leu Asp Thr Gln Tyr Ser Lys Val
                50                  55                  60

Leu Ala Leu Tyr Asn Gln His Asn Pro Gly Ala Ser Ala Ala Pro Cys
65                  70                  75                  80

Cys Val Pro Gln Ala Leu Glu Pro Leu Pro Ile Val Tyr Tyr Val Gly
```

```
                    85                   90                   95
Arg Lys Pro Lys Val Glu Gln Leu Ser Asn Met Ile Val Arg Ser Cys
                100                 105                  110

Lys Cys Ser
        115

<210> SEQ ID NO 40
<211> LENGTH: 115
<212> TYPE: PRT
<213> ORGANISM: Homo sapiens

<400> SEQUENCE: 40

Lys Lys Arg Ala Leu Asp Ala Ala Tyr Cys Phe Arg Asn Val Gln Asp
1                5                  10                  15

Asn Cys Cys Leu Arg Pro Leu Tyr Ile Asp Phe Lys Arg Asp Leu Gly
                 20                  25                  30

Trp Lys Trp Ile His Glu Pro Lys Gly Tyr Asn Ala Asn Phe Cys Ala
             35                  40                  45

Gly Ala Cys Pro Tyr Leu Trp Ser Ser Asp Thr Gln His Ser Arg Val
    50                  55                  60

Leu Ser Leu Tyr Asn Thr Ile Asn Pro Glu Ala Ser Ala Ser Pro Cys
65                  70                  75                  80

Cys Val Ser Gln Asp Leu Glu Pro Leu Thr Ile Leu Tyr Tyr Ile Gly
                 85                  90                  95

Lys Thr Pro Lys Ile Glu Gln Leu Ser Asn Met Ile Val Lys Ser Cys
                100                 105                 110

Lys Cys Ser
        115

<210> SEQ ID NO 41
<211> LENGTH: 115
<212> TYPE: PRT
<213> ORGANISM: Homo sapiens

<400> SEQUENCE: 41

Lys Lys Arg Ala Leu Asp Thr Asn Tyr Cys Phe Arg Asn Leu Glu Glu
1                5                  10                  15

Asn Cys Cys Val Arg Pro Leu Tyr Ile Asp Phe Arg Gln Asp Leu Gly
                 20                  25                  30

Trp Lys Trp Val His Glu Pro Lys Gly Tyr Tyr Ala Asn Phe Cys Ser
             35                  40                  45

Gly Pro Cys Pro Tyr Leu Arg Ser Ala Asp Thr Thr His Ser Thr Val
    50                  55                  60

Leu Gly Leu Tyr Asn Thr Leu Asn Pro Glu Ala Ser Ala Ser Pro Cys
65                  70                  75                  80

Cys Val Pro Gln Asp Leu Glu Pro Leu Thr Ile Leu Tyr Tyr Val Gly
                 85                  90                  95

Arg Thr Pro Lys Val Glu Gln Leu Ser Asn Met Val Val Lys Ser Cys
                100                 105                 110

Leu Cys Ser
        115

<210> SEQ ID NO 42
<211> LENGTH: 284
<212> TYPE: DNA
<213> ORGANISM: Cod
<220> FEATURE:
<221> NAME/KEY: CDS
```

<222> LOCATION: (3)..(284)
<223> OTHER INFORMATION:

<400> SEQUENCE: 42

```
ac tcc ccc gag tcc cgg tgc tgc cgc tac ccc ctc aca gtg gac ttt        47
   Ser Pro Glu Ser Arg Cys Cys Arg Tyr Pro Leu Thr Val Asp Phe
   1               5                   10                  15 gaa gac ttt ggc tgg gac tgg gtg atc gcg ccc aag cga tac aag gcc       95
Glu Asp Phe Gly Trp Asp Trp Val Ile Ala Pro Lys Arg Tyr Lys Ala
                20                  25                  30 aac tat tgc tcc ggg gag tgt gag tac atg tac ctg cag aag tac ccc      143
Asn Tyr Cys Ser Gly Glu Cys Glu Tyr Met Tyr Leu Gln Lys Tyr Pro
            35                  40                  45 cac acc cac ctg gtg cac aag gcc agc ccc cgg ggc aac gct ggg ccc      191
His Thr His Leu Val His Lys Ala Ser Pro Arg Gly Asn Ala Gly Pro
        50                  55                  60 tgc tgc acg ccc acc aag atg tcc ccc atc aac atg ctc tac ttc aac      239
Cys Cys Thr Pro Thr Lys Met Ser Pro Ile Asn Met Leu Tyr Phe Asn
65                  70                  75 cgc aag gag cag atc atc tac ggc aag ctg ccc tct atg gtc gta          284
Arg Lys Glu Gln Ile Ile Tyr Gly Lys Leu Pro Ser Met Val Val
80                  85                  90
```

<210> SEQ ID NO 43
<211> LENGTH: 94
<212> TYPE: PRT
<213> ORGANISM: Cod

<400> SEQUENCE: 43

```
Ser Pro Glu Ser Arg Cys Cys Arg Tyr Pro Leu Thr Val Asp Phe Glu
1               5                   10                  15

Asp Phe Gly Trp Asp Trp Val Ile Ala Pro Lys Arg Tyr Lys Ala Asn
            20                  25                  30

Tyr Cys Ser Gly Glu Cys Glu Tyr Met Tyr Leu Gln Lys Tyr Pro His
        35                  40                  45

Thr His Leu Val His Lys Ala Ser Pro Arg Gly Asn Ala Gly Pro Cys
    50                  55                  60

Cys Thr Pro Thr Lys Met Ser Pro Ile Asn Met Leu Tyr Phe Asn Arg
65                  70                  75                  80

Lys Glu Gln Ile Ile Tyr Gly Lys Leu Pro Ser Met Val Val
                85                  90
```

<210> SEQ ID NO 44
<211> LENGTH: 267
<212> TYPE: DNA
<213> ORGANISM: Sea Bass
<220> FEATURE:
<221> NAME/KEY: CDS
<222> LOCATION: (1)..(267)
<223> OTHER INFORMATION:
<220> FEATURE:
<221> NAME/KEY: misc_feature
<222> LOCATION: (204)..(204)
<223> OTHER INFORMATION: n = unknown
<220> FEATURE:
<221> NAME/KEY: VARIANT
<222> LOCATION: (68)..(68)
<223> OTHER INFORMATION: Xaa = unknown

<400> SEQUENCE: 44

```
tgc tgc cgc tac cca ctc aca gtg gac ttt gaa gac ttt ggt tgg gac       48
Cys Cys Arg Tyr Pro Leu Thr Val Asp Phe Glu Asp Phe Gly Trp Asp
1               5                   10                  15
```

```
tgg att att gcc cca aag cgc tac aag gcc aac tat tgc tcc ggg gag      96
Trp Ile Ile Ala Pro Lys Arg Tyr Lys Ala Asn Tyr Cys Ser Gly Glu
             20                  25                  30 tgt gag tac atg cac ttg cag aag tat ccg cac acc cac ctg gtg aac     144
Cys Glu Tyr Met His Leu Gln Lys Tyr Pro His Thr His Leu Val Asn
 35                  40                  45 aaa gcc aac ccc aga ggg acc gcg ggt ccc tgc tgc acc ccg acc aag     192
Lys Ala Asn Pro Arg Gly Thr Ala Gly Pro Cys Cys Thr Pro Thr Lys
 50                  55                  60 atg tcg ccc atn aac atg ctc tac ttt aac cga aaa gag cag ata atc     240
Met Ser Pro Xaa Asn Met Leu Tyr Phe Asn Arg Lys Glu Gln Ile Ile
 65                  70                  75                  80 tac ggc aag atc cct tcc atg gtg gtg                                  267
Tyr Gly Lys Ile Pro Ser Met Val Val
             85

<210> SEQ ID NO 45
<211> LENGTH: 89
<212> TYPE: PRT
<213> ORGANISM: Sea Bass
<220> FEATURE:
<221> NAME/KEY: misc_feature
<222> LOCATION: (68)..(68)
<223> OTHER INFORMATION: The 'Xaa' at location 68 stands for Ile, or Met

<400> SEQUENCE: 45

Cys Cys Arg Tyr Pro Leu Thr Val Asp Phe Glu Asp Phe Gly Trp Asp
 1               5                  10                  15

Trp Ile Ile Ala Pro Lys Arg Tyr Lys Ala Asn Tyr Cys Ser Gly Glu
             20                  25                  30

Cys Glu Tyr Met His Leu Gln Lys Tyr Pro His Thr His Leu Val Asn
 35                  40                  45

Lys Ala Asn Pro Arg Gly Thr Ala Gly Pro Cys Cys Thr Pro Thr Lys
 50                  55                  60

Met Ser Pro Xaa Asn Met Leu Tyr Phe Asn Arg Lys Glu Gln Ile Ile
 65                  70                  75                  80

Tyr Gly Lys Ile Pro Ser Met Val Val
             85

<210> SEQ ID NO 46
<211> LENGTH: 281
<212> TYPE: DNA
<213> ORGANISM: Sea Bream
<220> FEATURE:
<221> NAME/KEY: CDS
<222> LOCATION: (3)..(281)
<223> OTHER INFORMATION:

<400> SEQUENCE: 46 tc tca gac tcc cgg tgc tgc cgc tac ccg ctc acg gtg gac ttc gaa      47
   Ser Asp Ser Arg Cys Cys Arg Tyr Pro Leu Thr Val Asp Phe Glu
    1               5                  10                  15 gac ttt ggc tgg gac tgg att att gcc cca aag cgc tac aag gcc aac     95
Asp Phe Gly Trp Asp Trp Ile Ile Ala Pro Lys Arg Tyr Lys Ala Asn
             20                  25                  30 tat tgc tcc ggg gag tgt gag tac atg cac ttg cag aag tac ccg cac    143
Tyr Cys Ser Gly Glu Cys Glu Tyr Met His Leu Gln Lys Tyr Pro His
 35                  40                  45 acc cac ctg gtg aac aaa gcc aac ccc aga ggg tcc gcg ggc ccc tgc    191
Thr His Leu Val Asn Lys Ala Asn Pro Arg Gly Ser Ala Gly Pro Cys
 50                  55                  60 tgt acc ccc acc aag atg tcg ccc atc aac atg ctc tac ttt aac cga    239
```

```
Cys Thr Pro Thr Lys Met Ser Pro Ile Asn Met Leu Tyr Phe Asn Arg
 65                  70                  75 aag gag cag atc atc tac ggc aag atc ccg tcc atg gtg gtc            281
Lys Glu Gln Ile Ile Tyr Gly Lys Ile Pro Ser Met Val Val
 80                  85                  90

<210> SEQ ID NO 47
<211> LENGTH: 93
<212> TYPE: PRT
<213> ORGANISM: Sea Bream

<400> SEQUENCE: 47

Ser Asp Ser Arg Cys Cys Arg Tyr Pro Leu Thr Val Asp Phe Glu Asp
 1               5                  10                  15

Phe Gly Trp Asp Trp Ile Ile Ala Pro Lys Arg Tyr Lys Ala Asn Tyr
                 20                  25                  30

Cys Ser Gly Glu Cys Glu Tyr Met His Leu Gln Lys Tyr Pro His Thr
             35                  40                  45

His Leu Val Asn Lys Ala Asn Pro Arg Gly Ser Ala Gly Pro Cys Cys
         50                  55                  60

Thr Pro Thr Lys Met Ser Pro Ile Asn Met Leu Tyr Phe Asn Arg Lys
 65                  70                  75                  80

Glu Gln Ile Ile Tyr Gly Lys Ile Pro Ser Met Val Val
                 85                  90

<210> SEQ ID NO 48
<211> LENGTH: 280
<212> TYPE: DNA
<213> ORGANISM: Tautog
<220> FEATURE:
<221> NAME/KEY: CDS
<222> LOCATION: (2)..(280)
<223> OTHER INFORMATION:

<400> SEQUENCE: 48 c tca gag tcc cgg tgc tgc cgc tac cca ctc aca gtg gac ttt gaa gac    49
  Ser Glu Ser Arg Cys Cys Arg Tyr Pro Leu Thr Val Asp Phe Glu Asp
   1               5                  10                  15 ttt ggc tgg gac tgg att att gct cca aag cgc tac aag gcc aac tat    97
Phe Gly Trp Asp Trp Ile Ile Ala Pro Lys Arg Tyr Lys Ala Asn Tyr
                 20                  25                  30 tgc tcc ggg gag tgt gag tac atg cac ctg cag aag tac ccg cac acc   145
Cys Ser Gly Glu Cys Glu Tyr Met His Leu Gln Lys Tyr Pro His Thr
             35                  40                  45 cac ctc gtg aac aaa gcc aac ccc aga ggg act gca ggc ccc tgc tgc   193
His Leu Val Asn Lys Ala Asn Pro Arg Gly Thr Ala Gly Pro Cys Cys
         50                  55                  60 acc ccc acc aag atg tcg ccc atc aac atg ctc tac ttt aac cga aag   241
Thr Pro Thr Lys Met Ser Pro Ile Asn Met Leu Tyr Phe Asn Arg Lys
 65                  70                  75                  80 gag cag atc atc tac ggc aag atc ccc tcc atg gtg gtg               280
Glu Gln Ile Ile Tyr Gly Lys Ile Pro Ser Met Val Val
                 85                  90

<210> SEQ ID NO 49
<211> LENGTH: 93
<212> TYPE: PRT
<213> ORGANISM: Tautog

<400> SEQUENCE: 49

Ser Glu Ser Arg Cys Cys Arg Tyr Pro Leu Thr Val Asp Phe Glu Asp
 1               5                  10                  15
```

```
Phe Gly Trp Asp Trp Ile Ile Ala Pro Lys Arg Tyr Lys Ala Asn Tyr
            20                  25                  30

Cys Ser Gly Glu Cys Glu Tyr Met His Leu Gln Lys Tyr Pro His Thr
        35                  40                  45

His Leu Val Asn Lys Ala Asn Pro Arg Gly Thr Ala Gly Pro Cys Cys
    50                  55                  60

Thr Pro Thr Lys Met Ser Pro Ile Asn Met Leu Tyr Phe Asn Arg Lys
65                  70                  75                  80

Glu Gln Ile Ile Tyr Gly Lys Ile Pro Ser Met Val Val
                85                  90

<210> SEQ ID NO 50
<211> LENGTH: 208
<212> TYPE: DNA
<213> ORGANISM: X. laevis T7
<220> FEATURE:
<221> NAME/KEY: CDS
<222> LOCATION: (2)..(208)
<223> OTHER INFORMATION:

<400> SEQUENCE: 50 t cca aaa cga tat aaa gcc aac tat tgc tct gga gag tgc ggc att gtc     49
  Pro Lys Arg Tyr Lys Ala Asn Tyr Cys Ser Gly Glu Cys Gly Ile Val
  1               5                   10                  15 ttt ttg caa aag tac ccg cac aca cat ctt gtt caa caa gca aac ccc      97
Phe Leu Gln Lys Tyr Pro His Thr His Leu Val Gln Gln Ala Asn Pro
            20                  25                  30 aga ggt tct gct ggc cct tgc tgt acc cca acc aaa atg tcc cca att     145
Arg Gly Ser Ala Gly Pro Cys Cys Thr Pro Thr Lys Met Ser Pro Ile
        35                  40                  45 aat atg ttg tat ttc aat gaa aat gaa caa atc ata tat gga aaa att    193
Asn Met Leu Tyr Phe Asn Glu Asn Glu Gln Ile Ile Tyr Gly Lys Ile
    50                  55                  60 cca gct atg gtg gta                                                 208
Pro Ala Met Val Val
65

<210> SEQ ID NO 51
<211> LENGTH: 69
<212> TYPE: PRT
<213> ORGANISM: X. laevis T7

<400> SEQUENCE: 51

Pro Lys Arg Tyr Lys Ala Asn Tyr Cys Ser Gly Glu Cys Gly Ile Val
1               5                   10                  15

Phe Leu Gln Lys Tyr Pro His Thr His Leu Val Gln Gln Ala Asn Pro
            20                  25                  30

Arg Gly Ser Ala Gly Pro Cys Cys Thr Pro Thr Lys Met Ser Pro Ile
        35                  40                  45

Asn Met Leu Tyr Phe Asn Glu Asn Glu Gln Ile Ile Tyr Gly Lys Ile
    50                  55                  60

Pro Ala Met Val Val
65

<210> SEQ ID NO 52
<211> LENGTH: 4
<212> TYPE: PRT
<213> ORGANISM: Artificial Sequence
<220> FEATURE:
<223> OTHER INFORMATION: peptide portion of rat, chicken, murine and
      human GDF-8
```

```
<400> SEQUENCE: 52

Arg Ser Arg Arg
1

<210> SEQ ID NO 53
<211> LENGTH: 4
<212> TYPE: PRT
<213> ORGANISM: Artificial Sequence
<220> FEATURE:
<223> OTHER INFORMATION: Consensus peptide sequence of GDF-8 in aquatic
      species
<220> FEATURE:
<221> NAME/KEY: MISC_FEATURE
<222> LOCATION: (2)..(3)
<223> OTHER INFORMATION: Xaa =unknown

<400> SEQUENCE: 53

Arg Xaa Xaa Arg
1
```

GROWTH DIFFERENTIATION FACTOR-8 NUCLEIC ACID AND POLYPEPTIDE FROM AQUATIC SPECIES, AND TRANSGENIC AQUATIC SPECIES

This application is a continuation of U.S. Ser. No. 09/640,887, filed Aug. 17, 2000, now abandoned, which is a continuation-in-part application (CIP) of U.S. Ser. No. 09/378,238, filed Aug. 19, 1999 (now U.S. Pat. No. 6,465,239), which is a CIP of U.S. Ser. No. 08/795,071, filed Feb. 5, 1997 (now U.S. Pat. No. 5,994,618), which is a CIP of U.S. Ser. No. 08/525,596, filed Oct. 26, 1995 (now U.S. Pat. No. 5,827,733), which is a 371 application of PCT/US94/03019 filed on Mar. 18, 1994, which claims priority to U.S. Ser. No. 08/033,923 filed on Mar. 19, 1993, now abandoned, the entire contents of each of which is incorporated herein by reference.

BACKGROUND OF THE INVENTION

FIELD OF THE INVENTION

The invention relates generally to growth differentiation factor-8 (GDF-8; GDF-8) and specifically to nucleic acid sequences encoding GDF-8 polypeptide from a variety of aquatic organisms, as well as transgenic aquatic organisms having a disrupted GDF-8 gene and methods of making the same.

BACKGROUND INFORMATION

The transforming growth factor (TGF-β) superfamily encompasses a group of structurally-related proteins which affect a wide range of differentiation processes during embryonic development. The family includes, Mullerian inhibiting substance (MIS), which is required for normal male sex development (Behringer, et al., Nature, 345:167, 1990), *Drosophila* decapentaplegic (DPP) gene product, which is required for dorsal-ventral axis formation and morphogenesis of the imaginal disks (Padgett, et al., Nature, 325:81-84, 1987), the *Xenopus* Vg-1 gene product, which localizes to the vegetal pole of eggs ((Weeks, et al., Cell, 51:861-867, 1987), the activins (Mason, et al., Biochem, Biophys. Res. Commun., 135:957-964, 1986), which can induce the formation of mesoderm and anterior structures in *Xenopus* embryos (Thomsen, et al., Cell, 63:485, 1990), and the bone morphogenetic proteins (BMPs, osteogenin, OP-1) which can induce de novo cartilage and bone formation (Sampath, et al., J. Biol. Chem., 265:13198, 1990). The TGF-β can influence a variety of differentiation processes, including adipogenesis, myogenesis, chondrogenesis, hematopoiesis, and epithelial cell differentiation (for review, see Massague, Cell 49:437, 1987).

The proteins of the TGF-β family are initially synthesized as a large precursor protein which subsequently undergoes proteolytic cleavage at a cluster of basic residues approximately 110-140 amino acids from the C-terminus. The C-terminal regions, or mature regions, of the proteins are all structurally related and the different family members can be classified into distinct subgroups based on the extent of their homology. Although the homologies within particular subgroups range from 70% to 90% amino acid sequence identity, the homologies between subgroups are significantly lower, generally ranging from only 20% to 50%. In each case, the active species appears to be a disulfide-linked dimer of C-terminal fragments. Studies have shown that when the pro-region of a member of the TGF-β family is coexpressed with a mature region of another member of the TGF-β family, intracellular dimerization and secretion of biologically active homodimers occur (Gray et al., Science, 247:1328, 1990). Additional studies by Hammonds et al., (Molec. Endocrinol. 5:149, 1991) showed that the use of the BMP-2 pro-region combined with the BMP-4 mature region led to dramatically improved expression of mature BMP-4. For most of the family members that have been studied, the homodimeric species has been found to be biologically active, but for other family members, like the inhibins (Ling et al., Nature, 321:779, 1986) and the TGF-βs (Cheifetz et al., Cell, 48:409, 1987), heterodimers have also been detected, and these appear to have different biological properties than the respective homodimers.

In addition it is desirable to produce livestock and game animals, such as cows, sheep, pigs, chicken and turkey, fish which are relatively high in musculature and protein, and low in fat content. Many drug and diet regimens exist which may help increase muscle and protein content and lower undesirably high fat and/or cholesterol levels, but such treatment is generally administered after the fact, and is begun only after significant damage has occurred to the vasculature. Accordingly, it would be desirable to produce animals which are genetically predisposed to having higher muscle content, without any ancillary increase in fat levels.

The food industry has put much effort into increasing the amount of muscle and protein in foodstuffs. This quest is relatively simple in the manufacture of synthetic foodstuffs, but has been met with limited success in the preparation of animal foodstuffs. Attempts have been made, for example, to lower cholesterol levels in beef and poultry products by including cholesterol-lowering drugs in animal feed (see, e.g., Elkin and Rogler, Agric. Food Chem. 38:1635-1641, 1990). However, there remains a need for more effective methods of increasing muscle and reducing fat and cholesterol levels in animal food products.

The U.S. market for seafood is large and growing with per capita seafood consumption rising 23% in the last decade. During this period, the consumer price index for seafood jumped 244%, while red meat prices rose only half that amount. Despite efforts to manage wild finfish and shellfish populations at a sustained yield level, the U.S. consumes increasingly greater amounts than it produces from its fishers, thus depleting the resource. Ocean harvests worldwide are expected to meet only 90 million metric tons of the projected demand of 114 million metric tons in the year 2000 (Harvey, 1990).

Gene transfer technique has become a new and powerful approach to manipulate the genetic and phenotypic characteristic of both animals and plants. Various reports have been made in the production of transgenic fish and other aquatic organisms. The first transgenic study on fish was reported by Vielkind et al. (1982). These investigators injected swordtail tumor genes into the Platyfish, and found that the injected swordtail Tu genes could induce T-melanophore induction in Tu-free Platyfish. In 1985 and 1986, Zhu et al. reported the production of transgenic fish by growth hormone gene transfer. Using a aquatic organism metallothionein promoter ligated to a human GH structural gene, they successfully produced transgenic loach, goldfish and silver carp. On average, the transgenic fish were 1 to 3 times larger than control. Since then, several reports using similar gene constructs have been published (Rokkones et al. 1989, Guyomarde et al. 1989, Chen et al. 1990).

SUMMARY OF THE INVENTION

The present invention provides aquatic organism cell growth and differentiation factor, GDF-8, polypeptides and functional peptide portions thereof, polynucleotide sequences encoding such GDF-8 polypeptides, and antibodies that are specifically immunoreactive with a GDF-8 polypeptide or epitope thereof. GDF-8 expression can be involved in various cell proliferative disorders, particularly those disorders involving muscle, nerve, or adipose tissue.

In another embodiment, the subject invention provides non-human transgenic animals, particularly aquatic organisms, which are useful as a source of food products with high muscle and protein content, reduced fat and cholesterol content, or both. Such transgenic animals have been altered chromosomally in their germ cells and somatic cells so that the production of GDF-8 is reduced, or is completely disrupted. Such animals can exhibit decreased levels of GDF-8 in their system and higher than normal levels of muscle tissue, preferably without increased fat and/or cholesterol levels. Accordingly, the present invention also provides food products provided by such genetically modified aquatic organisms. Such food products have increased nutritional value because of the relative increase in muscle tissue. The transgenic animals of the invention include, for example, bovine, porcine, ovine and avian animals, and particularly transgenic aquatic organisms including, for example, finfish, frogs, shrimp, lobster, crab, squid, oysters and abalone.

In another embodiment, introduction of a polynucleotide encoding a GDF-8 sense or antisense sequence, or both, is accomplished by electroporation of the nucleic acid sequence encoding the transgene of interest into a fertilized aquatic organism egg, for example, a fertilized abalone or finfish egg. Typically, the nucleic acid sequence is flanked by regulatory sequences, which allow expression of the DNA sequence in the transgenic organism.

The present invention also provides a method of producing animal food products having increased muscle content. The method includes modifying the genetic makeup of the germ cells of a pronuclear embryo of the animal, particularly an aquatic organism, implanting the embryo into the oviduct of a pseudopregnant female thereby allowing the embryo to mature to full term progeny, testing the progeny for presence of the transgene to identify transgene-positive progeny, cross-breeding transgene-positive progeny to obtain further transgene-positive progeny and processing the progeny to obtain foodstuff. The modification of the germ cell comprises altering the genetic composition so as to disrupt or reduce the expression of the naturally occurring gene encoding for production of GDF-8 protein. In one embodiment, the transgene comprises antisense nucleotide sequences to a polynucleotide encoding a GDF-8 protein. In another embodiment, the transgene comprises a non-functional sequence that replaces or intervenes in the native GDF-8 gene, or encodes a dominant negative GDF-8 protein.

The subject invention also provides a method of producing aquatic organism food products having improved muscle content. The method includes modifying the genetic makeup of the germ cells of a pronuclear embryo of the aquatic animal, implanting the embryo into the oviduct of an appropriate pseudopregnant female, culturing the embryo under conditions whereby progeny are born, testing the progeny for presence of the genetic alteration to identify transgene-positive progeny, cross-breeding transgene-positive progeny and processing the progeny to obtain food products.

The invention also provides isolated polynucleotides encoding GDF-8 or a peptide portion thereof from aquatic organisms, and polypeptides encoded by such sequences. Also included are vectors and host cells containing such polynucleotides. By way of example, polynucleotides encoding finfish GDF-8, including zebrafish, salmon, cod, sea bass, sea bream, and tautog (SEQ ID NOS:28, 30, 32, 42, 44, 46 and 48, respectively), and frog GDF-8 (SEQ ID NO:50) are provided.

These and other objects and features of the invention will be more fully appreciated when the following detailed description of the invention is read in conjunction with the accompanying drawings.

BRIEF DESCRIPTION OF THE DRAWINGS

FIG. 1a is a northern blot showing expression of GDF-8 mRNA in adult tissues. The probe was a partial murine GDF-8 clone.

FIGS. 2a to 2g show nucleotide and predicted amino acid sequences of murine GDF-8 (FIG. 2a; SEQ ID NOS:5 and 6), human GDF-8 (FIG. 2b; SEQ ID NOS:7 and 8), rat GDF-8 (FIG. 2c; SEQ ID NOS:20 and 21), chicken GDF-8 (FIG. 2d; SEQ ID NOS:18 and 19), zebrafish (FIG. 2e; SEQ ID NOS:28 and 29), salmon 1 (FIG. 2f; SEQ ID NOS:30 and 31) and salmon 2 (FIG. 2g; SEQ ID NOS:32 and 33). The putative dibasic processing sites in the murine sequence are boxed.

FIG. 3a shows the alignment of the C-terminal sequences of murine GDF-8 (amino acid residues 265 to 276 of SEQ ID NO:12) with other members of the TGF-β superfamily (SEQ ID NOS: 22, 23, 24, 25, 26, 27 and 34 to 41, respectively). The conserved cysteine residues are boxed. Dashes denote gaps introduced in order to maximize alignment.

FIG. 3b shows the alignment of the C-terminal sequences of GDF-8 from human (SEQ ID NO:14), murine (SEQ ID NO:12), rat (SEQ ID NO:21) and chicken (SEQ ID NO:19) sequences.

FIGS. 3c to 3e show the alignment of the zebrafish amino acid sequence (SEQ ID NO:29) for GDF-8 with murine GDF-8 (SEQ ID NO:12) and C-terminal sequences of salmon allele 1 (salmon 1; SEQ ID NO: 31) and salmon allele 2 (salmon2; SEQ ID NO:33).

FIG. 4 shows amino acid homologies among different members of the TGF superfamily. Numbers represent percent amino acid identities between each pair calculated from the first conserved cysteine to the C-terminus. Boxes represent homologies among highly related members within particular subgroups.

FIGS. 5a to 5d show GDF-8 sequences. Nucleotide and amino acid sequences of murine (FIGS. 5a and 5b; SEQ ID NOS:11 and 12; GenBank accession number U84005) and human (FIGS. 5c and 5d; SEQ ID NOS:13 and 14) GDF-8 cDNA clones are shown. Numbers indicate nucleotide position relative to the 5' end. Consensus N-linked glycosylation signals are shaded. The putative RXXR proteolytic cleavage sites are boxed.

FIG. 7 shows a comparison of murine (SEQ ID NO:12) and human (SEQ ID NO:14) GDF-8 amino acid sequences. The predicted murine sequence is shown in the top lines and the predicted human sequence is shown in the bottom lines. Numbers indicate amino acid position relative to the N-terminus. Identities between the two sequences are denoted by a vertical line.

FIG. 11 shows chromosomal mapping of human GDF-8. DNA samples prepared from human/rodent somatic cell hybrid lines were subjected to PCR, electrophoresed on agarose gels, blotted, and probed. The human chromosome contained in each of the hybrid cell lines is identified at the top of each of the first 24 lanes (1-22, X, and Y). In the lanes designated M, CHO, and H, the starting DNA template was total genomic DNA from mouse, hamster, and human sources, respectively. In the lane marked B1, no template DNA was used. Numbers at left indicate the mobility of DNA standards.

FIG. 14 shows the partial nucleotide (SEQ ID NO:42) and amino acid (SEQ ID NO:43) sequences of cod GDF-8.

FIG. 15 shows the partial nucleotide (SEQ ID NO:44) and amino acid (SEQ ID NO:45) sequences of sea bass GDF-8.

FIG. 16 shows the partial nucleotide (SEQ ID NO:46) and amino acid (SEQ ID NO:47) sequences of sea bream GDF-8.

FIG. 17 shows the partial nucleotide (SEQ ID NO:48) and amino acid (SEQ ID NO:49) sequences of tautog GDF-8.

FIG. 18 shows the partial nucleotide (SEQ ID NO:50) and amino acid (SEQ ID NO:51) sequences of *Xenopus laevis* T7 GDF-8.

FIG. 20 shows the sequence pair distances of human (1), zebrafish (2), salmon (3), cod (4), sea bass (5), sea bream (6), tautog (7) and *X. laevis* (8) GDF-8 amino acid sequences, as determined using the Clustal method with PAM250 reisdue weight table. Percent similarity is shown above and to right of diagonal solid blocks, and percent divergence is shown below and to the left.

DETAILED DESCRIPTION OF THE INVENTION

Figure 1B:
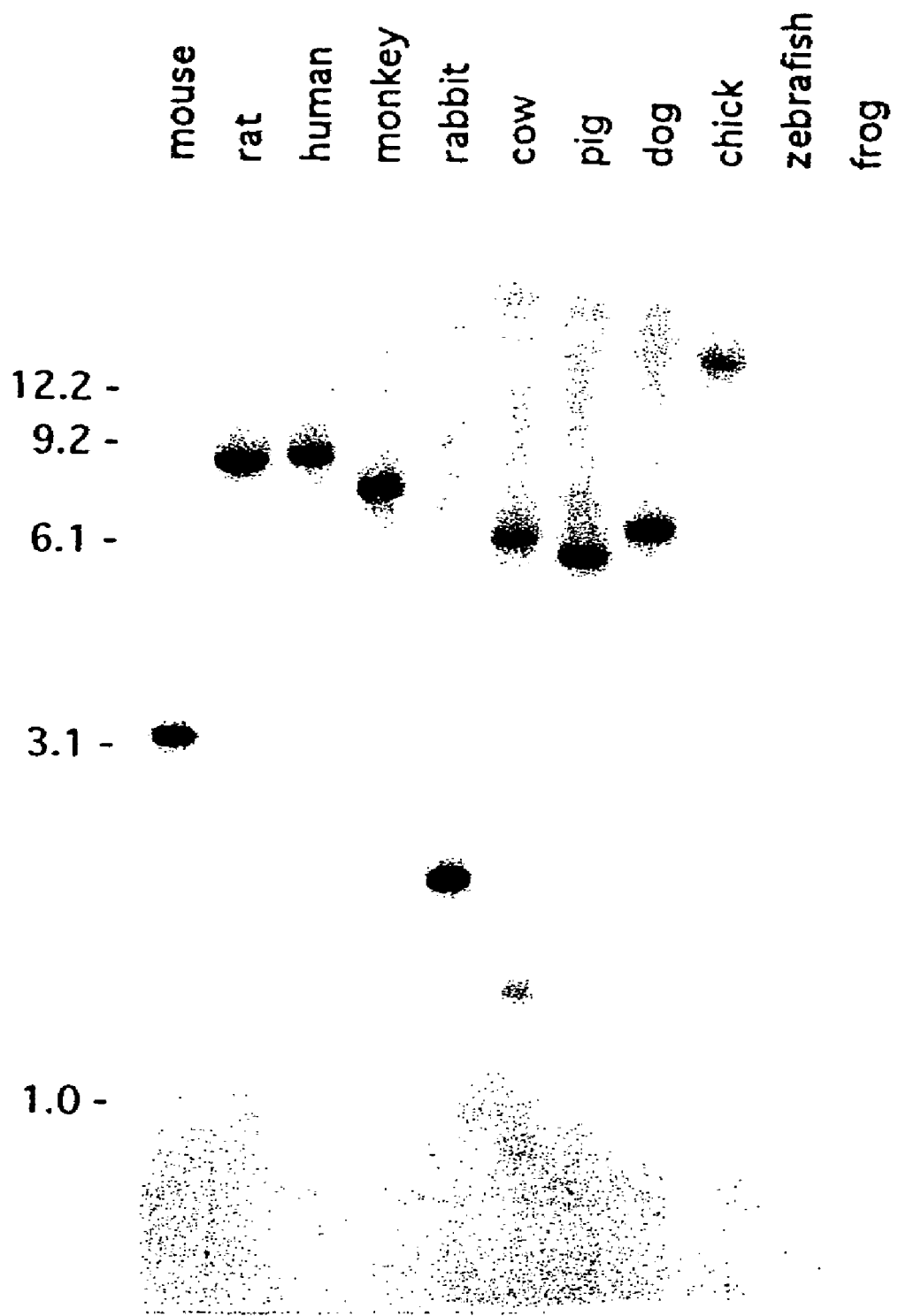
FIG. 1b is a Southern blot showing GDF-8 genomic sequences identified in mouse, rat, human, monkey, rabbit, cow, pig, dog and chicken.

The present invention provides aquatic organism derived growth and differentiation factor-8 (GDF-8, myostatin) polypeptides, peptide portions thereof, and polynucleotides encoding such GDF-8 polypeptides. GDF-8 is expressed at highest levels in muscle and at lower levels in adipose tissue.

As disclosed herein, the identification and isolation of GDF-8 polypeptides and the encoding polynucleotides provide a means to modulate the growth characteristics of non-human animals, particularly by increasing the muscle mass, decreasing the fat content, or both. The animals contemplated for use in the practice of the subject invention are those animals generally regarded as useful for the processing of foodstuffs, including, for example, avian such as meat-bred and egg-laying chicken and turkey, ovine such as lamb, bovine such as beef cattle and milk cows, and porcine. In particular, aquatic organisms (e.g., piscine) are contemplated for use in the present methods. For purposes of the present invention, these animals are referred to as "transgenic" when such an animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene fortuitously integrated into the chromosomes of somatic cells.

The TGF-β superfamily consists of multifunctional polypeptides that control proliferation, differentiation, and other functions in many cell types. Many of the peptides have regulatory effects, either positive or negative, on other peptide growth factors. The structural homology shared between the GDF-8 polypeptides of the invention and the members of the TGF-β family indicates that GDF-8 is a member of the TGF-β family of growth and differentiation factors. Based on the known activities of many of the other members, it can be expected that GDF-8 will possess biological activities that will make it useful as a diagnostic and therapeutic reagent.

In particular, certain members of the TGF-β superfamily have expression patterns or possess activities that relate to the function of the nervous system. For example, the inhibins and activins are expressed in the brain (Meunier et al., Proc. Natl. Acad. Sci., USA, 85:247, 1988; Sawchenko et al., Nature, 334:615, 1988), and activin can function as a nerve cell survival molecule (Schubert et al., Nature, 344: 868, 1990). Another family member, GDF-1, is nervous system-specific in its expression pattern (Lee, Proc. Natl. Acad. Sci., USA, 88:4250, 1991), and certain other family members, such as Vgr-1 (Lyons et al., Proc. Natl. Acad. Sci., USA, 86:4554, 1989; Jones et al., Development, 111:531, 1991), OP-1 (Ozkaynak et al., J. Biol. Chem., 267:25220, 1992), and BMP-4 (Jones et al., Development, 111:531, 1991), are also expressed in the nervous system. Because it is known that skeletal muscle produces a factor or factors that promote the survival of motor neurons (Brown, Trends Neurosci., 7:10, 1984), the expression of GDF-8 in muscle indicates that GDF-8 can act as a trophic factor for neurons. As such, GDF-8 can be useful for treating neurodegenerative diseases, such as amyotrophic lateral sclerosis or muscular dystrophy, and for maintaining cells or tissues in culture prior to transplantation.

GDF-8 can also be useful for treating disease processes involving muscle, such as in musculodegenerative diseases or in tissue repair due to trauma. In this regard, many other members of the TGF-β family are also important mediators of tissue repair. TGF-β has marked effects on the formation of collagen and causes a striking angiogenic response in the newborn mouse (Roberts et al., Proc. Natl. Acad. Sci., USA 83:4167, 1986). TGF-β also can inhibit the differentiation of myoblasts in culture (Massague et al., Proc. Natl. Acad. Sci., USA 83:8206, 1986). Moreover, because myoblast cells can be used as a vehicle for delivering genes to muscle for gene therapy, the properties of GDF-8 can be exploited for maintaining cells prior to transplantation or for enhancing the efficiency of the fusion.

The expression of GDF-8 in adipose tissue indicates that it further can be useful in the treatment of obesity or of disorders related to abnormal proliferation of adipocytes. In this regard, TGF-β has been shown to be a potent inhibitor of adipocyte differentiation in vitro (Ignotz and Massague, Proc. Natl. Acad. Sci., USA 82:8530, 1985).

The present invention provides substantially pure GDF-8 polypeptides and functional peptide portions thereof, as well as substantially pure polynucleotides encoding GDF-8. The term "substantially pure" or "isolated" is used herein to refer to a polypeptide, particularly GDF-8, or to an encoding polynucleotide that is relatively free of other proteins, lipids, carbohydrates or other materials with which it is naturally associated. One skilled in the art can substantially purify a GDF-8 polypeptide using standard techniques for protein purification. The substantially pure polypeptide can be identified as a single major band on a non-reducing polyacrylamide gel. The purity of the GDF-8 polypeptide can also be determined by amino-terminal (N-terminal) amino acid sequence analysis. Similarly, the artisan will know that an isolated polynucleotide encoding a GDF-8 can be obtained, for example, by cloning the polynucleotide using methods as disclosed herein.

A full length GDF-8 polypeptide comprises an amino terminal prodomain, which is involved in regulating GDF-8 activity, and a C-terminal domain, which, when free of the prodomain, exhibits GDF-8 activity (see U.S. Ser. No. 09/628,112, filed Jul. 27, 2000, which is incorporated herein by reference). The present invention provides substantially purified aquatic GDF-8 polypeptides and peptide portions thereof. As used herein, the term "pro-GDF-8" is used to refer to a full length polypeptide, including the amino terminal (pre)prodomain and the carboxy terminal (C-terminal) biologically active GDF-8 domain. The (pre)prodomain, hereinafter "prodomain," includes a signal peptide (leader sequence), which comprises about the first 15 to 30 amino acids at the amino terminus of the prodomain. The signal peptide can be cleaved from the full length pro-GDF polypeptide, which can be further cleaved at an Arg-Xaa-Xaa-Arg proteolytic cleavage site to produce the C-terminal GDF-8. The term "GDF-8" is used generally synonomously with the term "pro-GDF-8" unless otherwise indicated, for example, by referring to the C-terminal GDF-8 polypeptide.

Unless otherwise indicated, reference herein to amino acid residues is made with respect to a full length pro-GDF-8 polypeptide as shown, for example, for murine pro-GDF-8 (FIGS. 5a and 5b; SEQ ID NO:12) and human pro-GDF-8 (FIGS. 5c and 5d; SEQ ID NO:14). It should also be recognized that reference is made herein to particular polypeptides beginning or ending at "about" a particular amino acid residue. The term "about" is used in this context because it is recognized that a particular protease can cleave a pro-GDF-8 polypeptide at or immediately adjacent to a proteolytic cleavage recognition site, or one or a few amino acids from the recognition site. Similarly, the signal peptide can be cleaved at any position from about amino acid residue 15 to 30 of a pro-GDF-8 polypeptide, for example, at residue 15, 20, 25 or 30, without affecting the function, for example, of a remaining prodomain.

The term "peptide" or "peptide portion" is used broadly herein to mean two or more amino acids linked by a peptide bond. Generally, a peptide of the invention contains at least about six amino acids, usually contains about ten amino acids, and can contain fifteen or more amino acids, particularly twenty or more amino acids. It should be recognized that the term "peptide" is not used herein to suggest a particular size or number of amino acids comprising the molecule, and that a peptide of the invention can contain up to several amino acid residues or more.

A functional peptide portion of a pro-GDF-8 polypeptide is characterized, in part, in that it has an activity of GDF-8. Thus, peptides exhibiting a biological activity of GDF-8 are included in the invention, as are epitopic peptide, which provide an epitope substantially unique to GDF-8. As used herein, the term "functional peptide portion," when used in reference to a pro-GDF-8 polypeptide, means a contiguous amino acid sequence of a C-terminal GDF-8 polypeptide that can affect muscle growth or fat content of an organism, or that can specifically interact with a reagent that is known to specifically interact with GDF-8; or of a GDF-8 prodomain, which can inhibit the activity of a C-terminal GDF-8 polypeptide. An activin type II receptor (Act RII) such as Act RIIA or Act RIIB (see, for example, U.S. Pat. No. 5,885,794, which is incorporated herein by reference), or an anti-GDF-8 antibody, which specifically binds GDF-8, but not other members of the TGF-β family, are examples of reagents that specifically interact with a GDF-8 peptide.

A functional peptide portion of a GDF polypeptide can be identified using any of various assays known to be useful for identifying specific protein-protein interactions, including, for example, methods of gel electrophoresis, affinity chromatography, the two hybrid system of Fields and Song (*Nature* 340:245-246, 1989; see, also, U.S. Pat. No. 5,283,173; Fearon et al., *Proc. Natl. Acad. Sci. USA* 89:7958-7962, 1992; Chien et al., *Proc. Natl. Acad. Sci. USA* 88:9578-9582, 1991; Young, *Biol. Reprod.* 58:302-311 (1998), each of which is incorporated herein by reference), the reverse two hybrid assay (Leanna and Hannink, *Nucl. Acids Res.* 24:3341-3347, 1996, which is incorporated herein by reference), the repressed transactivator system (U.S. Pat. No. 5,885,779, which is incorporated herein by reference), the phage display system (Lowman, *Ann. Rev. Biophys. Biomol. Struct.* 26:401-424, 1997, which is incorporated herein by reference), GST/HIS pull down assays, mutant operators (WO 98/01879, which is incorporated herein by reference), the protein recruitment system (U.S. Pat. No. 5,776,689, which is incorporated herein by reference), and the like (see, for example, Mathis, *Clin. Chem.* 41:139-147, 1995 Lam, *Anticancer Drug Res.* 12:145-167, 1997; Phizicky et al., *Microbiol. Rev.* 59:94-123, 1995; each of which is incorporated herein by reference).

A functional peptide portion of a GDF polypeptide also can be identified using methods of molecular modeling. For example, an amino acid sequence of a mature GDF-8 peptide or peptide portion thereof can be entered into a computer system having appropriate modeling software, and a three dimensional representation of the GDF-8 ("virtual GDF-8") can be produced. A GDF-8 amino acid sequence also can be entered into the computer system, such that the modeling software can simulate portions of the GDF-8 sequence, for example, portions of the mature C-terminal domain, and can identify those peptide portions that can interact specifically with a virtual Act RII or a selected anti-GDF-8 antibody. A base line for a specific interaction can be predefined by modeling the virtual GDF-8 and the receptor or antibody, and identifying the amino acid residues in the virtual GDF-8 that are "contacted" by the reagent.

It should be recognized that such methods, including two hybrid assays and molecular modeling methods, also can be used to identify other molecules that specifically interact with a GDF-8. Thus, methods such as the two hybrid assay can be used to identify novel GDF-8 receptors using, for example, a GDF-8 polypeptide or a peptide portion thereof that specifically interacts with an Act RIIA or Act RIIB receptor as one binding component of the assay, and identifying a GDF receptor, which specifically interacts with the GDF-8 peptide. Similarly, methods of molecular modeling can be used to identify an agent that interacts specifically with a mature GDF polypeptide, or with a GDF receptor and, therefore, can be useful as an agonist or an antagonist of GDF signal transduction. Such an agent can be, for example, a functional peptide portion of GDF-8, GDF-11, or the like, or a chemical agent that mimics the action of GDF or a functional peptide portion thereof.

Modeling systems useful for the purposes disclosed herein can be based on structural information obtained, for example, by crystallographic analysis or nuclear magnetic resonance analysis, or on primary sequence information (see, for example, Dunbrack et al., "Meeting review: the Second meeting on the Critical Assessment of Techniques for Protein Structure Prediction (CASP2) (Asilomar, Calif., Dec. 13-16, 1996). *Fold Des*. 2(2): R27-42, (1997); Fischer and Eisenberg, *Protein Sci.* 5:947-55, 1996; (see, also, U.S. Pat. No. 5,436,850); Havel, *Prog. Biophys. Mol. Biol.* 56:43-78, 1991; Lichtarge et al., *J. Mol. Biol.* 274:325-37, 1997; Matsumoto et al., *J. Biol. Chem.* 270:19524-31, 1995; Sali et al., *J. Biol. Chem.* 268:9023-34, 1993; Sali, *Molec. Med. Today* 1:270-7, 1995a; Sali, *Curr. Opin. Biotechnol.* 6:437-51, 1995b; Sali et al., *Proteins* 23: 318-26, 1995c; Sali, *Nature Struct. Biol.* 5:1029-1032, 1998; U.S. Pat. No. 5,933,819; U.S. Pat. No. 5,265,030, each of which is incorporated herein by reference).

The crystal structure coordinates of a GDF-8 polypeptide or a GDF receptor can be used to design compounds that bind to the protein and alter its physical or physiological properties in a variety of ways. The structure coordinates of the protein can also be used to computationally screen small molecule data bases for agents that bind to the polypeptide to develop modulating or binding agents, which can act as agonists or antagonists of GDF-8 activity. Such agents can be identified by computer fitting kinetic data using standard equations (see, for example, Segel, "Enzyme Kinetics" (J. Wiley & Sons 1975), which is incorporated herein by reference).

Methods of using crystal structure data to design inhibitors or binding agents are known in the art. For example, GDF-8 polypeptide coordinates can be superimposed onto other available coordinates of similar polypeptides such as TGF-β family members, including a polypeptide having a bound inhibitor, to provide an approximation of the way the inhibitor interacts with the polypeptide. Computer programs employed in the practice of rational drug design also can be used to identify compounds that reproduce interaction characteristics similar to those found, for example, between a GDF-8 polypeptide and a reagent that specifically binds thereto. Detailed knowledge of the nature of the specific interactions allows for the modification of compounds to alter or improve solubility, pharmacokinetics, and the like, without affecting binding activity.

Computer programs for carrying out the activities necessary to design agents using crystal structure information are well known. Examples of such programs include, Catalyst Databases™—an information retrieval program accessing chemical databases such as BioByte Master File, Derwent WDI and ACD; Catalyst/HYPO™—generates models of compounds and hypotheses to explain variations of activity with the structure of drug candidates; Ludi™—fits molecules into the active site of a protein by identifying and matching complementary polar and hydrophobic groups; and Leapfrog™—"grows" new ligands using a genetic algorithm with parameters under the control of the user.

Various general purpose machines can be used with such programs, or it may be more convenient to construct more specialized apparatus to perform the operations. Generally, the embodiment is implemented in one or more computer programs executing on programmable systems each comprising at least one processor, at least one data storage system (including volatile and non-volatile memory and/or storage elements), at least one input device, and at least one output device. The program is executed on the processor to perform the functions described herein.

Each such program can be implemented in any desired computer language, including, for example, machine, assembly, high level procedural, or object oriented programming languages, to communicate with a computer system. In any case, the language may be a compiled or interpreted language. The computer program will typically be stored on a storage media or device, for example, a ROM, CD-ROM, magnetic or optical media, or the like, that is readable by a general or special purpose programmable computer, for configuring and operating the computer when the storage media or device is read by the computer to perform the procedures described herein. The system may also be considered to be implemented as a computer-readable storage medium, configured with a computer program, where the storage medium so configured causes a computer to operate in a specific and predefined manner to perform the functions described herein.

Embodiments of the invention include systems, for example, internet based systems, particularly computer systems which store and manipulate coordinate information obtained by crystallographic or NMR analysis, or amino acid or nucleotide sequence information, as disclosed herein. As used herein, the term "computer system" refers to the hardware components, software components, and data storage components used to analyze coordinates or sequences as set forth herein. The computer system typically includes a processor for processing, accessing and manipulating the sequence data. The processor can be any well known type of central processing unit, for example, a Pentium II or Pentium III processor from Intel Corporation, or a similar processor from Sun, Motorola, Compaq, Advanced MicroDevices or International Business Machines.

Typically the computer system is a general purpose system that comprises the processor and one or more internal data storage components for storing data, and one or more data retrieving devices for retrieving the data stored on the data storage components. A skilled artisan can readily appreciate that any one of the currently available computer systems are suitable.

In one embodiment, the computer system includes a processor connected to a bus, which is connected to a main memory, preferably implemented as RAM, and one or more internal data storage devices such as a hard drive or other computer readable media having data recorded thereon. In some embodiments, the computer system further includes one or more data retrieving devices for reading the data stored on the internal data storage devices.

The data retrieving device may represent, for example, a floppy disk drive, a compact disk drive, a magnetic tape drive, or a modem capable of connection to a remote data storage system (e.g., via the internet). In some embodiments, the internal data storage device is a removable computer readable medium such as a floppy disk, a compact disk, a magnetic tape, etc. containing control logic and/or data recorded thereon. The computer system may advantageously include or be programmed by appropriate software for reading the control logic and/or the data from the data storage component once inserted in the data retrieving device.

The computer system generally include a display, which is used to display output to a computer user. It should also be noted that the computer system can be linked to other computer systems in a network or wide area network to provide centralized access to the computer system.

Where it is desired to identify a chemical entity that interacts specifically with GDF-8 or with a GDF receptor, any of several methods to screen chemical entities or fragments for their ability to interact specifically with the molecule can be used. This process may begin by visual inspection, for example, of GDF-8 and the receptor on the computer screen. Selected peptide portions of the GDF-8 polypeptide, or chemical entities that can act as mimics, then can be positioned in a variety of orientations, or docked, within an individual binding site of the receptor. Docking can be accomplished using software such as Quanta and Sybyl, followed by energy minimization and molecular dynamics with standard molecular mechanics force fields, such as CHARMM and AMBER.

Specialized computer programs can be particularly useful for selecting peptide portions of GDF-8, or chemical entities, useful, for example, as a GDF receptor agonist or antagonist. Such programs include, for example, GRID (Goodford, *J. Med. Chem.*, 28:849-857, 1985; available from Oxford University, Oxford, UK); MCSS (Miranker and Karplus, *Proteins: Structure. Function and Genetics* 11:29-34, 1991, available from Molecular Simulations, Burlington Mass.); AUTODOCK (Goodsell and Olsen, *Proteins: Structure, Function, and Genetics* 8:195-202, 1990, available from Scripps Research Institute, La Jolla Calif.); DOCK (Kuntz, et al., *J. Mol. Biol.* 161:269-288, 1982, available from University of California, San Francisco Calif.), each of which is incorporated herein by reference.

Suitable peptides or agents that have been selected can be assembled into a single compound or binding agent. Assembly can be performed by visual inspection of the relationship of the fragments to each other on the three-dimensional image displayed on a computer screen, followed by manual model building using software such as Quanta or Sybyl. Useful programs to aid one of skill in the art in connecting the individual chemical entities or fragments include, for example, CAVEAT (Bartlett et al, *Special Pub., Royal Chem. Soc.* 78:182-196, 1989, available from the University of California, Berkeley Calif.); 3D Database systems such as MACCS-3D (MDL Information Systems, San Leandro Calif.; for review, see Martin, *J. Med. Chem.* 35:2145-2154, 1992); HOOK (available from Molecular Simulations, Burlington, Mass.), each of which is incorporated herein by reference.

In addition to the method of building or identifying such specifically interacting agents in a step-wise fashion, one fragment or chemical entity at a time as described above, the agents can be designed as a whole or de novo using either an empty active site or, optionally, including some portions of a known agent that specifically interacts with a GDF-8 polypeptide, for example, an anti-GDF-8 antibody. Such methods include, for example, LUDI (Bohm, *J. Comp. Aid. Molec. Design* 6:61-78, 1992, available from Biosym Technologies, San Diego Calif.); LEGEND (Nishibata and Itai, *Tetrahedron* 47:8985, 1991, available from Molecular Simulations, Burlington Mass.); LeapFrog (available from Tripos Associates, St. Louis Mo.), and those described by Cohen et al. (*J. Med. Chem.* 33:883-894, 1990) and by Navia and Murcko, *Curr. Opin. Struct. Biol*2:202-210, 1992, each of which is incorporated herein by reference).

Specific computer software is available in the art to evaluate compound deformation energy and electrostatic interaction. Examples of programs designed for such uses include Gaussian 92, revision C (Frisch, Gaussian, Inc., Pittsburgh Pa., 1992); AMBER, version 4.0 (Kollman, University of California at San Francisco, 1994); QUANTA/CHARMM (Molecular Simulations, Inc., Burlington Mass., 1994); and Insight II/Discover (Biosysm Technologies Inc., San Diego Calif., 1994). These programs may be implemented using, for example, a Silicon Graphics workstation, IRIS 4D/35 or IBM RISC/6000 workstation model 550. Other hardware systems and software packages will be known to those skilled in the art of which the speed and capacity are continually modified.

A molecular modeling process for identifying an agent that interacts specifically with a molecule of interest, for example, with a mature GDF-8 polypeptide can be performed as disclosed herein. In a first step, a virtual representation of a target molecule, for example, GDF-8, is performed. Thus, in one embodiment, the present invention provides a virtual representation of a target molecule, wherein the target molecule is GDF-8 polypeptide or a functional peptide portion thereof. The virtual representation of the target molecule can be displayed or can be maintained in a computer system memory. The process begins at a start state, comprising the virtual target molecule, then moves to a state wherein a database containing one or more virtual test molecules stored to a memory in the computer system. As discussed above, the memory can be any type of memory, including RAM or an internal storage device.

The process then moves to a state wherein the ability of a virtual first test molecule, for example, a receptor or a chemical reagent, to specifically interact with the virtual target molecule, for example, GDF-8, is determined, wherein the database containing the virtual test molecule, which can be one of a population of test molecules, is opened for analysis of the an interaction of the virtual target molecule and virtual test molecule, and the analysis is made. A determination of a specific interaction can be made based on calculations performed by software maintained in the computer system, or by comparison to a predetermined specific interaction, which can be stored in a memory in the computer system and accessed as appropriate.

The process then moves to a state wherein, where a specific interaction is detected, the virtual test molecule is displayed, or is stored in a second database on the computer. If appropriate, the process is repeated for the virtual target molecule and a second virtual test molecule, a third virtual test molecule, and so on, as desired.

If a determination is made that a virtual test molecule specifically interacts with the virtual target molecule, the identified virtual test molecule is moved from the database and can be displayed to the user. This state notifies the user that the molecule with the displayed name or structure interacts specifically with the target molecule within the constraints that were entered. Once the name of the identified test molecule is displayed to the user, the process moves to a decision state, wherein a determination is made whether more virtual test molecules exist in the database or are to be examined. If no more molecules exist in the database, then the process terminates at an end state. However, if more test molecules exist in the database, then the process moves to a state, wherein a pointer is moved to the next test molecule in the database so that it can be examined for specific binding activity. In this manner, the new molecule is examined for the ability to interact specifically with the virtual target molecule.

The present invention further provides polynucleotides encoding a GDF-8 polypeptide of an aquatic organism. Such polynucleotides can be DNA, cDNA or RNA sequences that encode some or all of a pro-GDF-8 polypeptide. Thus, polynucleotides encoding all or a portion of pro-GDF-8 are also included within the present invention, particularly polynucleotides encoding a polypeptide having a GDF-8 activity. Such polynucleotides include substantially purified naturally occurring polynucleotides, as well as synthetic and intentionally manipulated polynucleotides. For example, a GDF-8 polynucleotide as disclosed herein can be subjected to site-directed mutagenesis. The polynucleotides of the invention include sequences that are degenerate as a result of the genetic code. There are 20 natural amino acids, most of which are specified by more than one codon. Therefore, all degenerate nucleotide sequences encoding a polypeptide as disclosed herein are included in the invention, provided the amino acid sequence of GDF-8 polypeptide encoded by the nucleotide sequence is functionally unchanged. Particularly useful polynucleotides of the invention include antisense GDF-8 polynucleotides sequences.

The term "polynucleotide" is used broadly herein to mean a sequence of two or more deoxyribonucleotides or ribonucleotides that are linked together by a phosphodiester bond. As such, the term "polynucleotide" includes RNA and DNA, which can be a gene or a portion thereof, a cDNA, a synthetic polydeoxyribonucleic acid sequence, or the like, and can be single stranded or double stranded, as well as a DNA/RNA hybrid. Furthermore, the term "polynucleotide" as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR). In various embodiments, a polynucleotide of the invention can contain nucleoside or nucleotide analogs, or a backbone bond other than a phosphodiester bond (see above).

In general, the nucleotides comprising a polynucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucl. Acids Res.* 22:5220-5234 (1994); Jellinek et al., *Biochemistry* 34:11363-11372 (1995); Pagratis et al., *Nature Biotechnol.* 15:68-73 (1997), each of which is incorporated herein by reference).

The covalent bond linking the nucleotides of a polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* 22:977-986 (1994); Ecker and Crooke, *BioTechnology* 13:351360 (1995), each of which is incorporated herein by reference). The incorporation of non-naturally occurring nucleotide analogs or bonds linking the nucleotides or analogs can be particularly useful where the polynucleotide is to be exposed to an environment that can contain a nucleolytic activity, including, for example, a tissue culture medium or upon administration to a living subject, since the modified polynucleotides can be less susceptible to degradation.

A polynucleotide comprising naturally occurring nucleotides and phosphodiester bonds can be chemically synthesized or can be produced using recombinant DNA methods, using an appropriate polynucleotide as a template. In comparison, a polynucleotide comprising nucleotide analogs or covalent bonds other than phosphodiester bonds generally will be chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995).

Where a polynucleotide encodes a peptide, for example, a peptide portion of GDF-8 or a peptide agent, the coding sequence generally is contained in a vector and is operatively linked to appropriate regulatory elements, including, if desired, a tissue specific promoter or enhancer. The encoded peptide can be further operatively linked, for example, to peptide tag such as a His-6 tag or the like, which can facilitate identification of expression of the agent in the target cell. A polyhistidine tag peptide such as His-6 can be detected using a divalent cation such as nickel ion, cobalt ion, or the like. Additional peptide tags include, for example, a FLAG epitope, which can be detected using an anti-FLAG antibody (see, for example, Hopp et al., *BioTechnology* 6:1204 (1988); U.S. Pat. No. 5,011,912, each of which is incorporated herein by reference); a c-myc epitope, which can be detected using an antibody specific for the epitope; biotin, which can be detected using streptavidin or avidin; and glutathione S-transferase, which can be detected using glutathione. Such tags can provide the additional advantage that they can facilitate isolation of the operatively linked peptide or peptide agent, for example, where it is desired to obtain a substantially purified peptide.

As used herein, the term "operatively linked" or "operatively associated" means that two or more molecules are positioned with respect to each other such that they act as a single unit and effect a function attributable to one or both molecules or a combination thereof. For example, a polynucleotide sequence encoding a GDF-8 or functional peptide portion thereof can be operatively linked to a regulatory element, in which case the regulatory element confers its regulatory effect on the polynucleotide similarly to the way in which the regulatory element would effect a polynucleotide sequence with which it normally is associated with in a cell. A first polynucleotide coding sequence also can be operatively linked to a second (or more) coding sequence such that a chimeric polypeptide can be expressed from the operatively linked coding sequences. The chimeric polypeptide can be a fusion polypeptide, in which the two (or more) encoded peptides are translated into a single polypeptide, i.e., are covalently bound through a peptide bond; or can be translated as two discrete peptides that, upon translation, can operatively associate with each other to form a stable complex.

Polynucleotides, including genomic DNA sequences, encoding pro-GDF-8 and peptide portions of GDF-8 are disclosed herein. The encoded polypeptide is predicted to contain two potential proteolytic processing sites (KR and RR). Cleavage of the precursor at the downstream site would generate a mature biologically active C-terminal fragment of 109 and 103 amino acids for murine and human species, respectively, with a predicted molecular weight of approximately 12,400 Daltons. Also disclosed are full length murine and human GDF-8 cDNA sequences. The murine pre-pro-GDF-8 protein is 376 amino acids in length, which is encoded by a 2676 base pair nucleotide sequence, beginning at nucleotide 104 and extending to a TGA stop codon at nucleotide 1232. The human pro-GDF-8 protein is 375 amino acids and is encoded by a 2743 base pair sequence, with the open reading frame beginning at nucleotide 59 and extending to nucleotide 1184. GDF-8 is capable of forming dimers, or heterodimers, with an expected molecular weight of approximately 23 to 30 kiloDaltons (kDa; see Example 4). For example, GDF-8 can form heterodimers with other family members, such as GDF-11.

Alignment of the amino acid sequences of human, murine, rat and chicken pro-GDF-8 (FIG. 3b) indicates that the sequences are 100% identical in the C-terminal biologically active fragment. Furthermore, alignment of murine, zebrafish and two salmon allele GDF-8 sequences (FIGS. 3c and 3d) demonstrates that GDF-8 amino acid sequences are highly conserved among quite diverse species; and FIG. 19 demonstrates that the C-terminal GDF-8 polypeptide is highly conserved among aquatic organisms. In view of this disclosure, it will be a routine matter to obtain polynucleotides encoding GDF-8 polypeptides from any species, particularly aquatic organisms such as piscine species.

Figure 3D:
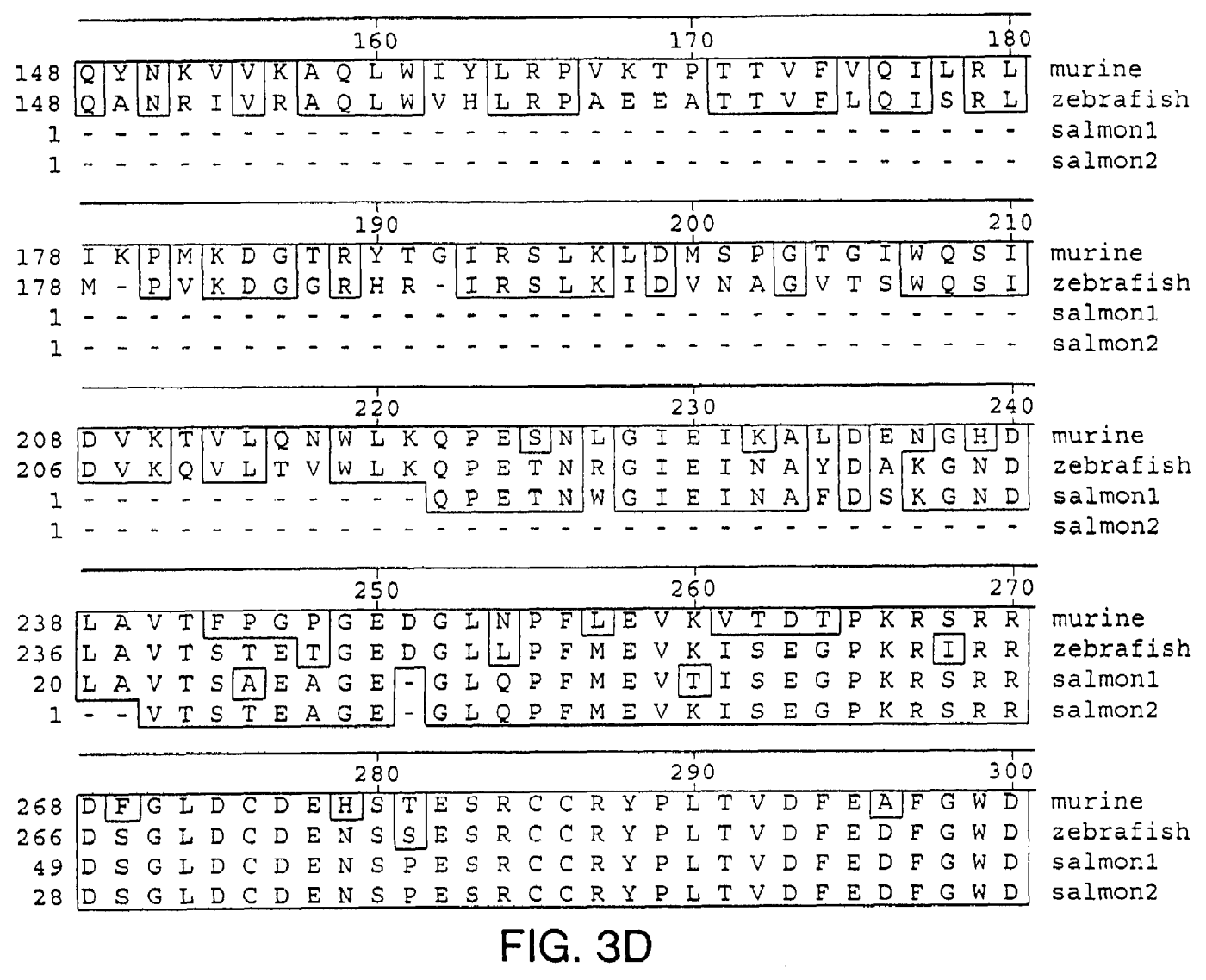
Figure 19:
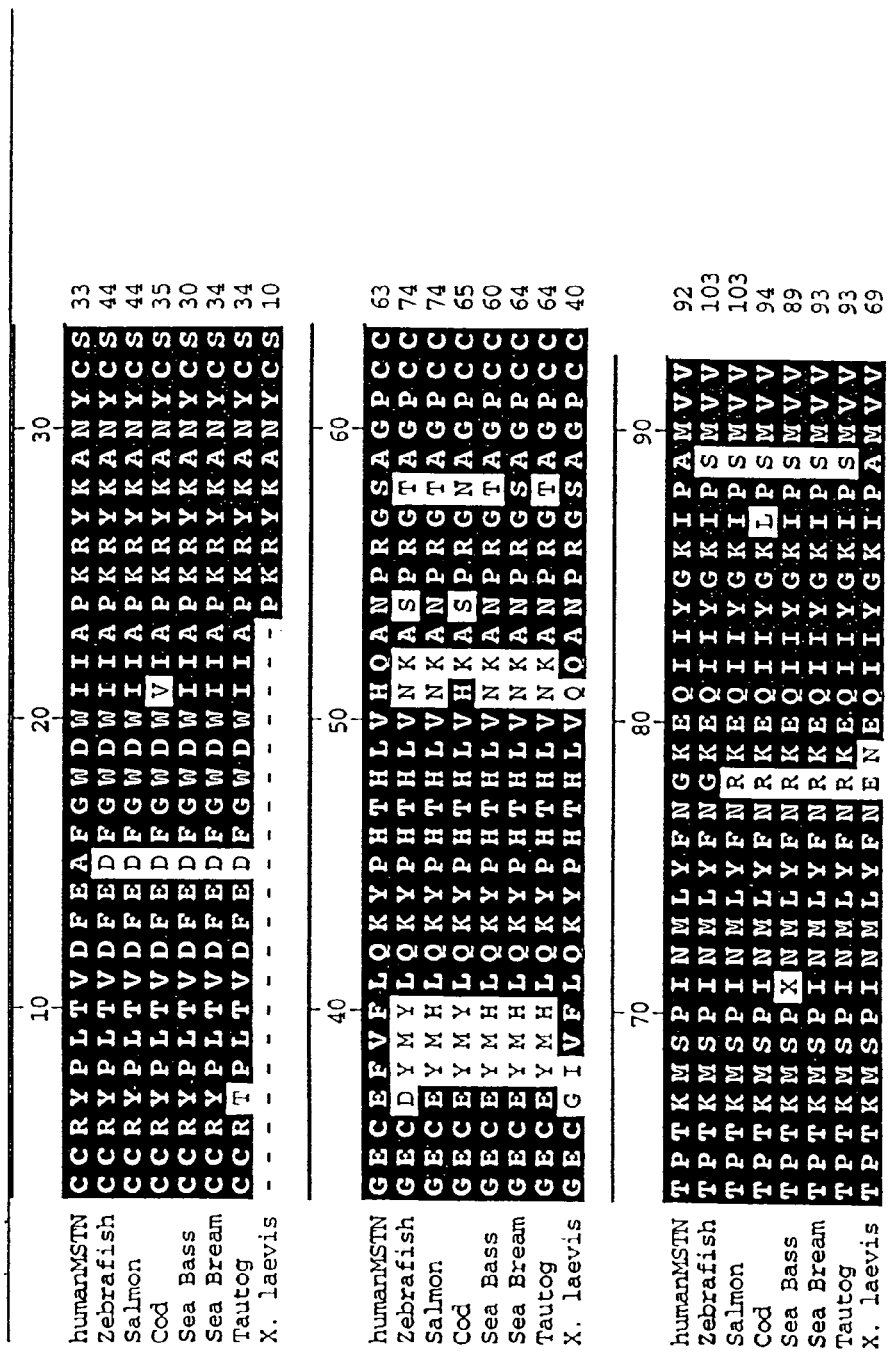
FIG. 19 provides an alignment of amino acid residues 281 to 370 of human GDF-8 (SEQ ID NO:14) and the corresponding amino acids of zebrafish (SEQ ID NO:28). salmon (SEQ ID NO:31/33), cod (SEQ ID NO:43), sea bass (SEQ ID NO:45), sea bream (SEQ ID NO:47) tautog (SEQ ID NO: 49) and *X. laevis* (SEQ ID NO: 51) GDF-8.
Figure 21:
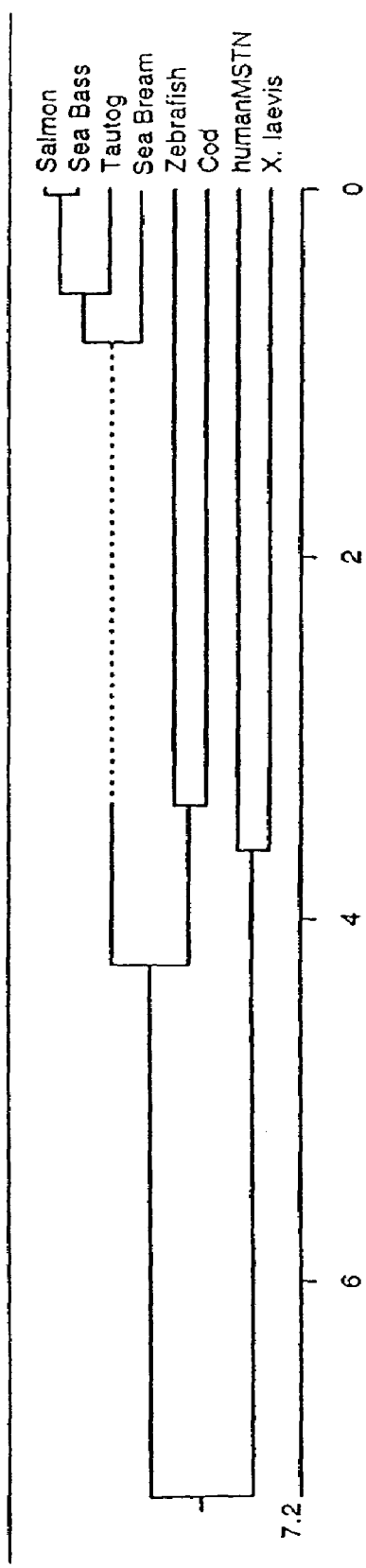
FIG. 21 shows a phylogenetic tree of GDF-8 from the indicated organisms.

Polynucleotides encoding pro-GDF-8 polypeptides or peptide portions thereof for various piscine species, including zebrafish (FIG. 2e; SEQ ID NOS: 28 and 29), salmon allele 1 ("salmon-1"; FIG. 2f; SEQ ID NOS:30 and 31), salmon allele 2 ("salmon-2"; FIG. 2g; SEQ ID NOS: 32 and 33), cod (FIG. 14; SEQ ID NOS:42 and 43), sea bass (FIG. 15; SEQ ID NOS:44 and 45); sea bream (FIG. 16; SEQ ID NOS:46 and 47), tautog (FIG. 17; SEQ ID NOS:48 and 49), and an amphibian, *X. laevis* (frog; FIG. 18; SEQ ID NOS:50 and 51) are disclosed herein (see, also, FIGS. 3c and 3d, and FIG. 19). FIGS. 3c and 3d show an amino acid sequence alignment between murine, zebrafish, salmon-1 and salmon-2 GDF-8. The C-terminal sequences are highly conserved. Cleavage of the precursor at the downstream RXXR site generates a mature biologically active C-terminal fragment of about 109 amino acids for murine GDF-8. A comparison of the fish sequences in FIGS. 3c and 3d with murine in the C-terminal fragment reveals only 14 amino acid differences (approximately 88% identity). Similarly high sequence identity is shared among GDF-8 polypeptides of human and various aquatic organisms (FIG. 19). Accordingly, the invention provides GDF-8 polynucleotide sequences encoding a GDF-8 polypeptide of an aquatic organism, wherein the GDF-8 polypeptide has a biologically active C-terminal fragment that is at least about 60%, 65%, 70%, 75%, 80%, 85%, 90% or 95% identical to murine GDF-8 polypeptide. The polynucleotides of the invention are exemplified by finfish and amphibian GDF-8 polynucleotides that encode a GDF-8 polypeptide having the amino acid sequences as set forth above.

In one embodiment, the invention provides an isolated polynucleotide encoding a GDF-8 polypeptide comprising an amino acid sequence as set forth in SEQ ID NO:29 (FIG. 2e), SEQ ID NO:31 (FIG. 2f), SEQ ID NO:33 (FIG. 2g), SEQ ID NO:43 (FIG. 14), SEQ ID NO:45 (FIG. 15), SEQ ID NO:47 (FIG. 16), SEQ ID NO:49 (FIG. 17) or SEQ ID NO:51 (FIG. 18). In another embodiment, an isolated polynucleotide of the invention is set forth as SEQ ID NO:28, SEQ ID NO:30, SEQ ID NO:32, SEQ ID NO:42, SEQ ID NO:44, SEQ ID NO:46, SEQ ID NO:48 or SEQ ID NO:50, wherein T can also be U. A polynucleotide of the invention can be as set forth above, or can be a polynucleotide complementary thereto, and can be a nucleotide sequence of at least 15 nucleotides, wherein the sequence specifically hybridizes a polynucleotide as set forth above, but not to a polynucleotide encoding a non-aquatic pro-GDF-8 polypeptide such as SEQ ID NO:12, SEQ ID NO:14, SEQ ID NO:19 or SEQ ID NO:21, or to a polynucleotide set forth as SEQ ID NO:11, SEQ ID NO:13, SEQ ID NO:18 or SEQ ID NO:20.

The C-terminal GDF-8 polypeptide, which includes the sequence following the putative proteolytic processing site of pro-GDF-8, shows substantial homology to the known members of the TGF-β superfamily. The GDF-8 sequence contains most of the residues that are highly conserved in other family members and in other species (see FIGS. 3a and 3b). Like the TGF-β and inhibin-β polypeptides, GDF-8 contains an extra pair of cysteine residues in addition to the 7 cysteines found in virtually all other family members. Among the known family members, GDF-8 is most homologous to Vgr-1 (45% sequence identity; see FIG. 4).

Minor modifications of the recombinant GDF-8 primary amino acid sequence can result in proteins which have substantially equivalent activity as compared to the exemplified GDF-8 polypeptides. Such modifications can be deliberate, such as modification introduced by a method such as site-directed mutagenesis, or can be spontaneous. All of the polypeptides produced by these modifications are encompassed within the present invention, provided polypeptide maintains a function of GDF-8, as disclosed herein. Deletion of one or more amino acids can also result in a modification of the structure of the resultant molecule without significantly altering its biological activity. This can lead to the development of a smaller active molecule which would have broader utility. For example, one can remove amino or carboxy terminal amino acids which are not required for the biological activity or other function of GDF-8.

The polynucleotide sequence encoding a GDF-8 polypeptide of the invention includes the exemplified sequences, as well as conservative variations of the exemplified polypeptide sequences. The term "conservative variation" as used herein refers to a replacement of an amino acid residue by another, biologically similar amino acid residue. Examples of conservative variations include the substitution of a hydrophobic residue such as isoleucine, valine, leucine or methionine for another, or the substitution of a polar residue for another, such as the substitution of arginine for lysine, glutamic for aspartic acid, or glutamine for asparagine, and the like. The term "conservative variation" also includes the use of a substituted amino acid in place of an unsubstituted parent amino acid, provided that an antibody that specifically interacts with the substituted polypeptide also is specifically immunoreactive with the unsubstituted polypeptide.

A polynucleotide of the invention can be obtained by several methods. For example, the polynucleotide can be isolated using hybridization or computer-based techniques which are well known in the art. These include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

In view of the disclosed extensive sequence conservation shared among GDF-8 polypeptides, particularly among species as diverse as humans and fish, it is a routine matter to obtain polynucleotides encoding GDF-8 from any species, particularly aquatic organisms, including the remainders of the partial GDF-8 sequences disclosed herein, and to identify GDF-8 expression in any species. In particular, the mature GDF-8 C-terminal sequence shares significant homology to other members of the TGF-β superfamily, and GDF-8 contains most of the residues that are highly conserved among the other family members and in other species. Furthermore, GDF-8, like the TGF-βs and inhibin βs, contains an extra pair of cysteine residues in addition to the seven cysteine residues present in virtually all other family members. GDF-8 is most homologous to Vgr-1 (45% sequence identity). Like other members of the TGF-β superfamily, GDF-8 is synthesized as a larger precursor pre-pro-GDF-8 polypeptide that is proteolytic cleaved into an active GDF-8 peptide. However, based on the present disclosure, nucleotide and amino acid sequences that are unique to aquatic species, and, therefore, not found in non-aquatic GDF-8 polynucleotides or polypeptides, readily can be identified. The identification of such aquatic organism conserved sequences allows the preparation of reagents such as oligonucleotide probes and antibodies that, in turn, provide a means to distinguish the aquatic organism GDF-8 polypeptides and polynucleotides of the invention from non-aquatic organism GDF-8 polypeptides and polynucleotides.

Polynucleotides encoding GDF-8 polypeptides of various organisms can be identified using well known procedures and algorithms based on identity or homology to the disclosed sequences. Homology or identity is often measured using sequence analysis software such as the Sequence Analysis Software Package of the Genetics Computer Group (University of Wisconsin Biotechnology Center, 1710 University Avenue, Madison, Wis. 53705). Such software matches similar sequences by assigning degrees of homology to various deletions, substitutions and other modifications. The terms "homology" and "identity," when used herein in the context of two or more nucleic acids or polypeptide sequences, refer to two or more sequences or subsequences that are the same or have a specified percentage of amino acid residues or of nucleotides that are the same when compared and aligned for maximum correspondence over a comparison window or designated region as measured using any number of sequence comparison algorithms or by manual alignment and visual inspection.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "comparison window" is used broadly herein to include reference to a segment of any one of the number of contiguous positions, for example, about 20 to 600 positions, for example, amino acid or nucleotide position, usually about 50 to about 200 positions, more usually about 100 to about 150 positions, in which a sequence may be compared to a reference sequence of the same number of contiguous positions after the two sequences are optimally aligned. Methods of alignment of sequence for comparison are well-known in the art. Optimal alignment of sequences for comparison can be conducted, for example, by the local homology algorithm of Smith and Waterman (*Adv. Appl. Math.* 2:482, 1981), by the homology alignment algorithm of Needleman and Wunsch (*J. Mol. Biol.* 48:443, 1970), by the search for similarity method of Person and Lipman (*Proc. Natl. Acad. Sci., USA* 85:2444, 1988), each of which is incorporated herein by reference; by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection. Other algorithms for determining homology or identity include, for example, the BLAST program (Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W, CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences.

A number of genome databases are available for comparison, including, for example, a substantial portion of the human genome is available as part of the Human Genome Sequencing Project (J. Roach, and is found on the world wide web weber.u.Washington.edu/~roach/human_genome_progress 2.html). In addition, at least twenty-one genomes have been sequenced in their entirety, including, for example, M. genitalium, M. jannaschii, H. influenzae, E. coli, yeast (S. cerevisiae), and D. melanogaster. Significant progress has also been made in sequencing the genomes of model organism such as mouse, C. elegans, and Arabadopsis sp. Several databases containing genomic information annotated with some functional information are maintained by different organizations, and are accessible via the internet, for example, is found on the world wide web:wwwtigr.org/tdb; www.genetics.wisc.edu; genome-www.stanford.edu/~ball; hiv-web.lanl.gov; www.ncbi.nlm.nih.gov; www.ebi.ac.uk; Pasteur.fr/other/biology; and genome.wi.mit.edu.

One example of a useful algorithm is BLAST and BLAST 2.0 algorithms, which are described by Altschul et al. (Nucleic Acids Res. 25:3389-3402, 1977; J. Mol. Biol. 215:403-410, 1990, each of which is incorporated herein by reference). Software for performing BLAST analyses is publicly available through the National Center for Biotechnology Information (http://www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra, 1977, 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectations (E) of 10, and the BLOSUM62 scoring matrix (see Henikoff and Henikoff, Proc. Natl. Acad. Sci., USA 89:10915, 1989) alignments (B) of 50, expectation (E) of 10, M=5, N=−4, and a comparison of both strands.

The BLAST algorithm also performs a statistical analysis of the similarity between two sequences (see, for example, Karlin and Altschul, Proc. Natl. Acad. Sci., USA 90:5873, 1993, which is incorporated herein by reference). One measure of similarity provided by BLAST algorithm is the smallest sum probability (P(N)), which provides an indication of the probability by which a match between two nucleotide or amino acid sequences would occur by chance. For example, a nucleic acid is considered similar to a references sequence if the smallest sum probability in a comparison of the test nucleic acid to the reference nucleic acid is less than about 0.2, more preferably less than about 0.01, and most preferably less than about 0.001.

In one embodiment, protein and nucleic acid sequence homologies are evaluated using the Basic Local Alignment Search Tool ("BLAST"). In particular, five specific BLAST programs are used to perform the following task:

(1) BLASTP and BLAST3 compare an amino acid query sequence against a protein sequence database;

(2) BLASTN compares a nucleotide query sequence against a nucleotide sequence database;

(3) BLASTX compares the six-frame conceptual translation products of a query nucleotide sequence (both strands) against a protein sequence database;

(4) TBLASTN compares a query protein sequence against a nucleotide sequence database translated in all six reading frames (both strands); and (5) TBLASTX compares the six-frame translations of a nucleotide query sequence against the six-frame translations of a nucleotide sequence database.

The BLAST programs identify homologous sequences by identifying similar segments, which are referred to herein as "high-scoring segment pairs," between a query amino or nucleic acid sequence and a test sequence which is preferably obtained from a protein or nucleic acid sequence database. High-scoring segment pairs are preferably identified (aligned) by means of a scoring matrix, many of which are known in the art. Preferably, the scoring matrix used is the BLOSUM62 matrix (Gonnet et al., Science 256:1443-1445, 1992; Henikoff and Henikoff, Proteins 17:49-61, 1993, each of which is incorporated herein by reference). Less preferably, the PAM or PAM250 matrices may also be used (Schwartz and Dayhoff, eds., "Matrices for Detecting Distance Relationships: Atlas of Protein Sequence and Structure" (Washington, National Biomedical Research Foundation 1978)). BLAST programs are accessible through the U.S. National Library of Medicine, for example, at www.ncbi.nlm.nih.gov.

The parameters used with the above algorithms may be adapted depending on the sequence length and degree of homology studied. In some embodiments, the parameters may be the default parameters used by the algorithms in the absence of instructions from the user.

A GDF-8 polynucleotide can be obtained from any organism, including mouse, rat, cow, pig, human, chicken, turkey, finfish and other aquatic organisms and other species. For purposes of the present invention, the term "aquatic organism" is used to refer to a non-human vertebrate or invertebrate animal that spends all or a significant part of its life in water. The term "significant part," when used in reference to the life of an aquatic organism, refers to a period of time such that the animal would not be expected to propagate, develop or thrive absent this period of time. Such a significant part of an aquatic organism's life can be, for example, the time required for an organism such as an amphibian to enter water in order to maintain homeostasis, or the time required for an organism such as an alligator to feed.

Examples of aquatic organisms include those belonging to the superclass *Pisces* (piscine), including the class *Chondriethyes* such as sharks, skates and rays, and the class *Osteichthyes* such as salmon, trout, char, ayu, carp, crucian carp, goldfish, roach, whitebait, eel, conger eel, sardine, zebrafish, flying fish, sea bass, sea bream, parrot bass, snapper, mackerel, horse mackerel, tuna, bonito, yellowtail, rockfish, fluke, sole, flounder, blowfish, filefish. Additional examples of aquatic organisms include those belonging to the class *Cephalopoda* such as squid, cuttlefish, octopus; the class *Pelecypoda* such as clam (e.g., hardshell, Manila, Quahog, Surf, Soft-shell); cockles, mussels, periwinkles; scallops (e.g., sea, bay, calloo); conch, snails, sea cucumbers; ark shell; oyster (e.g., *C. virginica*, Gulf, New Zealand, Pacific); the class *Gastropoda* such as turban shell, abalone (e.g. green, pink, red); the class *Crustacea* such as lobster, including but not limited to Spiny, Rock, and American; prawn; shrimp, including but not limited to *M. rosenbergii*, *P. styllrolls*, *P. indicus*, *P. jeponious*, *P. monodon*, *P. vannemel*, *M. ensis*, *S. melantho*, and *N. norvegious*, cold water shrimp; crab, including but not limited to Blue, rook, stone, king, queen, snow, brown, dungeness, Jonah, Mangrove, and soft-shelled, squilla, krill, langostinos, crayfish/crawfish, including but not limited to Blue, Marron, Red Claw, Red Swamp, Soft-shelled, and white; the class *Amphibia*, including frogs; and the class *Echinodermata*, including but not limited to sea urchins; as well as aquatic organisms belonging to the phylum *Annelida*, and to the phylum *Chordata*, including but not limited to reptiles such as alligators and turtles.

The present invention provides nucleotide sequences that specifically hybridize to a polynucleotide encoding an aquatic organism GDF-8, for example, SEQ ID NO: 28, 30, 32, 42, 44, 46, 48 or 50, but not to a polynucleotide encoding a non-aquatic organism GDF-8, for example, SEQ ID NO: 11, 13, 18 or 20. Thus, as used herein, the term specifically hybridize means that the nucleotide sequence is able to distinguish such polynucleotides. Based on the present disclosure, the identification and selection of such nucleotide sequences will be a routine matter, which can be performed, for example, by visual examination of the disclosed sequences or, preferably, by subjecting the disclosed sequence to a computerized analysis using the programs disclosed herein.

Screening procedures which rely on nucleic acid hybridization make allow the isolation of any gene sequence from any organism using a probe derived from the polynucleotide sequences provided herein. For example, a probe derived from the zebrafish or salmon sequence, as provided herein, can be used to identify GDF-8 polynucleotides from other aquatic organisms. In particular, due to the conservation in the C-terminal fragment, it can be advantageous to use a nucleic acid probe directed to a polynucleotide sequence encoding this portion of GDF-8 that are unique to aquatic organisms. Oligonucleotide probes, which correspond to a part of the sequence encoding the protein in question, can be synthesized chemically. This requires that short, oligopeptide stretches of amino acid sequence be known. The DNA sequence encoding the protein can be deduced from the genetic code, however, the degeneracy of the code must be taken into account. A mixed addition reaction can be performed when the sequence is degenerate, including a heterogeneous mixture of denatured double stranded DNA. For such screening, hybridization is performed on single stranded DNA or denatured double stranded DNA. Hybridization is particularly useful in the detection of cDNA clones derived from sources where an extremely low amount of mRNA sequences relating to the polypeptide of interest are present. Thus, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace et al., Nucl. Acid Res. 9:879, 1981).

The development of specific polynucleotides encoding GDF-8 polypeptides can also be obtained by: 1) isolation of double stranded DNA sequences from the genomic DNA; 2) chemical manufacture of a DNA sequence to provide the necessary codons for the polypeptide of interest; and 3) in vitro synthesis of a double stranded DNA sequence by reverse transcription of mRNA isolated from a eukaryotic donor cell. In the latter case, a double stranded DNA complement of mRNA is eventually formed which is generally referred to as cDNA. Of these methods, the isolation of genomic DNA isolates is the least common. This is especially true when it is desirable to obtain the microbial expression of mammalian polypeptides, due to the presence of introns in the genomic sequences.

In nucleic acid hybridization reactions, the conditions used to achieve a particular level of stringency will vary, depending on the nature of the polynucleotides being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically. Depending on the species from which the GDF-8 probe is derived, one of skill in the art can use these hybridization guidelines to determine whether or not a positively hybridized sequence is a GDF-8 nucleic acid sequence or not. For example, higher stringency might be used to identify GDF-8 within species than between species. Further, due to the conservation of sequence in the C-terminal region of the polypeptide, probes to nucleotides encoding the C-terminal region can be used at higher stringency.

The synthesis of polynucleotide sequences is frequently the method of choice when the entire sequence of amino acid residues of the desired polypeptide product is known. When the entire sequence of amino acid residues of the desired polypeptide is not known, the direct synthesis of polynucleotide sequences is not possible and the method of choice is the synthesis of cDNA sequences. Among the standard procedures for isolating cDNA sequences of interest is the formation of plasmid-carrying or phage-carrying cDNA libraries, which are derived from reverse transcription of mRNA which is abundant in donor cells that have a high level of genetic expression. When used in combination with PCR technology, even rare expression products can be cloned. In those cases where significant portions of the amino acid sequence of the polypeptide are known, the production of labeled single or double stranded DNA or RNA probe sequences duplicating a sequence putatively present in the target cDNA can be employed in DNA/DNA hybridization procedures, which are carried out on cloned copies of the cDNA that have been denatured into a single stranded form (Jay et al., Nucl. Acid Res., 11:2325, 1983).

A cDNA expression library, such as lambda gt11, can be screened indirectly for GDF-8 peptides having at least one epitope, using antibodies specific for GDF-8. Such antibodies can be either polyclonally or monoclonally derived and used to detect expression product indicative of the presence of GDF-8 cDNA.

A polynucleotide encoding a GDF-8 can be expressed in a cell in culture by introducing the polynucleotide into a suitable host cell. "Host cells" are cells in which a vector can be propagated and, where the vector is an expression vector, a polynucleotide cloned into the vector can be expressed. The term "host cell" includes any progeny of a parental host cell. It is understood that all progeny may not be identical to the parental cell since there can be mutations that occur during replication. Such progeny nevertheless are included when the term "host cell" is used. Methods of stable transfer of a polynucleotide into a cell, wherein the introduced polynucleotides is continuously maintained in the host cell, are well known and routine in the art.

In the present invention, the GDF-8 polynucleotide sequences can be inserted into a recombinant expression vector. The term "recombinant expression vector" refers to a plasmid, virus or other vehicle known in the art that has been manipulated by insertion or incorporation of the GDF-8 genetic sequences. Such expression vectors contain a promoter sequence that facilitates the efficient transcription of the inserted genetic sequence of the host, an origin of replication, and can contain specific gene sequence that allows phenotypic selection of cells containing the vector. Vectors suitable for use in the present invention include, but are not limited to the T7-based expression vector for expression in bacteria (Rosenberg et al., Gene, 56:125, 1987), the pMSXND expression vector for expression in mammalian cells (Lee and Nathans, J. Biol. Chem., 263:3521, 1988) and baculovirus-derived vectors for expression in insect cells. The DNA segment can be present in the vector operably linked to regulatory elements, for example, a promoter such as a T7, metallothionein I or polyhedrin promoter.

Polynucleotide sequences encoding GDF-8 can be expressed in either prokaryotes or eukaryotes. Host cells can include microbial, yeast, insect, and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention. Preferably, the mature C-terminal region of GDF-8 is expressed from a cDNA clone containing the entire coding sequence of GDF-8. Alternatively, the C-terminal portion of GDF-8 can be expressed as a fusion protein with the pro-region of another member of the TGF-β family or co-expressed with another pro-region (see for example, Hammonds et al., Molec. Endocrinol., 5:149, 1991; Gray and Mason, Science, 247:1328, 1990).

Introduction of a polynucleotide into a host cell can be carried out by conventional techniques well known in the art. The host cell can be, for example, a prokaryotic cell, such as E. coli competent cells, which are prepared from cells harvested after exponential growth phase and subsequently treated by the $CaCl_2$ method (or using $MgCl_2$ or RbCl). Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors can be used. Eukaryotic cells can also be cotransformed with DNA sequences encoding the GDF-8 of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (see for example, Eukaryotic Viral Vectors, Cold Spring Harbor Laboratory, Gluzman ed., 1982).

An expression vector (or the polynucleotide) generally contains or encodes a promoter sequence, which can provide constitutive or, if desired, inducible or tissue specific or developmental stage specific expression of the encoding polynucleotide, a poly-A recognition sequence, and a ribosome recognition site or internal ribosome entry site, or other regulatory elements such as an enhancer, which can be tissue specific. The vector also can contain elements required for replication in a prokaryotic or eukaryotic host system or both, as desired. Such vectors, which include plasmid vectors and viral vectors such as bacteriophage, baculovirus, retrovirus, lentivirus, adenovirus, vaccinia virus, semliki forest virus and adeno-associated virus vectors, are well known and can be purchased from a commercial source (Promega, Madison Wis.; Stratagene, La Jolla Calif.; GIBCO/BRL, Gaithersburg Md.) or can be constructed by one skilled in the art (see, for example, Meth. Enzyol., Vol. 185, Goeddel, ed. (Academic Press, Inc., 1990); Jolly, Canc. Gene Ther. 1:51-64, 1994; Flotte, J. Bioenerg. Biomemb. 25:37-42, 1993; Kirshenbaum et al., J. Clin. Invest. 92:381-387, 1993; each of which is incorporated herein by reference).

A tetracycline (tet) inducible promoter can be particularly useful for driving expression of a polynucleotide of the invention, for example, a polynucleotide encoding an antisense GDF-8 molecule or a dominant negative form of a GDF-8 polypeptide, which can reduce or inhibit the interaction of native GDF-8 with a GDF receptor. Upon administration of tetracycline, or a tetracycline analog, to a subject containing a polynucleotide operatively linked to a tet inducible promoter, expression of the encoded antisense molecule or dominant negative GDF-8 peptide is induced, whereby the antisense molecule or the peptide can effect its activity. Such a method can be used, for example, to induce muscle hypertrophy in an adult organism.

The polynucleotide also can be operatively linked to tissue specific regulatory element, for example, a muscle cell specific regulatory element, such that expression of an encoded molecule is restricted to the muscle cells in an individual, or to muscle cells in a mixed population of cells in culture, for example, an organ culture. Muscle cell specific regulatory elements including, for example, the muscle creatine kinase promoter (Sternberg et al., Mol. Cell. Biol. 8:2896-2909, 1988, which is incorporated herein by reference) and the myosin light chain enhancer/promoter (Donoghue et al., Proc. Natl. Acad. Sci., USA 88:5847-5851, 1991, which is incorporated herein by reference) are well known in the art.

Viral expression vectors can be particularly useful for introducing a polynucleotide into a cell, particularly a cell in a subject. Viral vectors provide the advantage that they can infect host cells with relatively high efficiency and can infect specific cell types. For example, a polynucleotide encoding a GDF-8 polypeptide or functional peptide portion thereof can be cloned into a baculovirus vector, which then can be used to infect an insect host cell, thereby providing a means to produce large amounts of the encoded prodomain. The viral vector also can be derived from a virus that infects cells of an organism of interest, for example, vertebrate host cells such as mammalian, avian or piscine host cells. Viral vectors can be particularly useful for introducing a polynucleotide useful in performing a method of the invention into a target cell. Viral vectors have been developed for use in particular hosts, include, for example, retroviral vectors, other lentivirus vectors such as those based on the human immunodeficiency virus (HIV), adenovirus vectors, adeno-associated virus vectors, herpesvirus vectors, vaccinia virus vectors, and the like (see Miller and Rosman, *BioTechniques* 7:980-990, 1992; Anderson et al., *Nature* 392:25-30 Suppl., 1998; Verma and Somia, *Nature* 389:239-242, 1997; Wilson, *New Engl. J. Med*. 334:1185-1187 (1996), each of which is incorporated herein by reference).

When retroviruses, for example, are used for gene transfer, replication competent retroviruses theoretically can develop due to recombination of retroviral vector and viral gene sequences in the packaging cell line utilized to produce the retroviral vector. Packaging cell lines in which the production of replication competent virus by recombination has been reduced or eliminated can be used to minimize the likelihood that a replication competent retrovirus will be produced. All retroviral vector supernatants used to infect cells are screened for replication competent virus by standard assays such as PCR and reverse transcriptase assays. Retroviral vectors allow for integration of a heterologous gene into a host cell genome, which allows for the gene to be passed to daughter cells following cell division.

A polynucleotide, which can be contained in a vector, can be introduced into a cell by any of a variety of methods known in the art (Sambrook et al., *Molecular Cloning: A laboratory manual* (Cold Spring Harbor Laboratory Press 1989); Ausubel et al., *Current Protocols in Molecular Biology*, John Wiley and Sons, Baltimore, Md. (1987, and supplements through 1995), each of which is incorporated herein by reference). Such methods include, for example, transfection, lipofection, microinjection, electroporation and, with viral vectors, infection; and can include the use of liposomes, microemulsions or the like, which can facilitate introduction of the polynucleotide into the cell and can protect the polynucleotide from degradation prior to its introduction into the cell. The selection of a particular method will depend, for example, on the cell into which the polynucleotide is to be introduced, as well as whether the cell is isolated in culture, or is in a tissue or organ in culture or in situ.

Introduction of a polynucleotide into a cell by infection with a viral vector is particularly advantageous in that it can efficiently introduce the nucleic acid molecule into a cell ex vivo or in vivo (see, for example, U.S. Pat. No. 5,399,346, which is incorporated herein by reference). Moreover, viruses are very specialized and can be selected as vectors based on an ability to infect and propagate in one or a few specific cell types. Thus, their natural specificity can be used to target the nucleic acid molecule contained in the vector to specific cell types. As such, a vector based on an HIV can be used to infect T cells, a vector based on an adenovirus can be used, for example, to infect respiratory epithelial cells, a vector based on a herpesvirus can be used to infect neuronal cells, and the like. Other vectors, such as adeno-associated viruses can have greater host cell range and, therefore, can be used to infect various cell types, although viral or non-viral vectors also can be modified with specific receptors or ligands to alter target specificity through receptor mediated events. Additional methods of introducing a transgene into a cell are described below.

The invention includes antibodies immunoreactive with GDF-8 polypeptide or functional peptide portions thereof. Antibody which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler et al., Nature, 256:495, 1975). The term antibody as used in this invention is meant to include intact molecules as well as antigen binding fragments thereof, such as Fab and F(ab')$_2$, Fv and SCA fragments, which can bind an epitopic determinant on GDF-8.

(1) An Fab fragment consists of a monovalent antigen-binding fragment of an antibody molecule, and can be produced by digestion of a whole antibody molecule with the enzyme papain, to yield a fragment consisting of an intact light chain and a portion of a heavy chain.

(2) An Fab' fragment of an antibody molecule can be obtained by treating a whole antibody molecule with pepsin, followed by reduction, to yield a molecule consisting of an intact light chain and a portion of a heavy chain. Two Fab' fragments are obtained per antibody molecule treated in this manner.

(3) An (Fab')$_2$ fragment of an antibody can be obtained by treating a whole antibody molecule with the enzyme pepsin, without subsequent reduction. A (Fab')$_2$ fragment is a dimer of two Fab' fragments, held together by two disulfide bonds.

(4) An Fv fragment is defined as a genetically engineered fragment containing the variable region of a light chain and the variable region of a heavy chain expressed as two chains.

(5) A single chain antibody ("SCA") is a genetically engineered single chain molecule containing the variable region of a light chain and the variable region of a heavy chain, linked by a suitable, flexible polypeptide linker.

As used herein, the term "epitope" refers to an antigenic determinant on an antigen, such as a GDF-8 polypeptide, to which the paratope of an antibody such as an anti-GDF-8 antibody specifically binds. Antigenic determinants usually consist of chemically active surface groupings of molecules, such as amino acids or sugar side chains, and can have specific three dimensional structural characteristics, as well as specific charge characteristics.

As used herein, the term "binds specifically" or "specific binding activity," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, F(ab')$_2$, Fd and Fv fragments of an antibody that retain specific binding activity for an epitope of an aquatic organism GDF-8 polypeptide, are included within the definition of an antibody. For purposes of the present invention, an antibody that reacts specifically with an epitope of an aquatic organism GDF-8 polypeptide, for example, is considered to not substantially react with a non-aquatic organism GDF-8 or with another member of the TGF-β family of proteins if the antibody has at least a two-fold greater binding affinity, generally at least a fivefold greater binding affinity, and particularly at least a ten-fold greater binding affinity for the myostatin receptor as compared to the TGF-β family member. Such antibodies of the invention can be obtained using routine methods, for example, by passing a polyclonal antibody raised against an aquatic organism GDF-8 polypeptide, or epitopic portion thereof, over a column having bound thereto non-aquatic organism GDF-8 polypeptides, TGF-β family members, or the like, and collecting the fraction of antibodies that does not bind to the column bound proteins.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275-1281 (1989), which is incorporated herein by reference). These and other methods of making, for example, chimeric, humanized, CDR-grafted, single chain, and bifunctional antibodies are well known to those skilled in the art (Winter and Harris, *Immunol. Today* 14:243-246, 1993; Ward et al., *Nature* 341:544-546, 1989; Harlow and Lane, *Antibodies: A laboratory manual* (Cold Spring Harbor Laboratory Press, 1988); Hilyard et al., *Protein Engineering: A practical approach* (IRL Press 1992); Borrabeck, *Antibody Engineering*, 2d ed. (Oxford University Press 1995); each of which is incorporated herein by reference).

As indicated above, antigens that can be used in producing GDF-8-specific antibodies include non-aquatic organism GDF-8 polypeptides or GDF-8 polypeptide fragments. The polypeptide or peptide used to immunize an animal can be obtained by standard recombinant, chemical synthetic, or purification methods. As is well known in the art, in order to increase immunogenicity, an antigen can be conjugated to a carrier protein. Commonly used carriers include keyhole limpet hemocyanin (KLH), thyroglobulin, bovine serum albumin (BSA), and tetanus toxoid. The coupled peptide is then used to immunize the animal (e.g., a mouse, a rat, or a rabbit). In addition to such carriers, well known adjuvants can be administered with the antigen to facilitate induction of a strong immune response.

The invention provides a method for detecting a cell proliferative disorder of muscle or adipose tissue which comprises contacting an anti-GDF-8 antibody with a cell suspected of having a GDF-8 associated disorder and detecting binding to the antibody. The term "cell proliferative disorder" is used herein to denote a disorder characterized, at least in part, by the presence of malignant cells or the presence of non-malignant cell populations, which often appear to differ from the surrounding tissue both morphologically and genotypically. Malignant cells (i.e. cancer) develop as a result of a multistep process. A GDF-8 polynucleotide that is an antisense molecule is useful in treating malignancies of the various organ systems, particularly cells in muscle or adipose tissue. Essentially, any disorder which is etiologically linked to altered expression of GDF-8 could be considered susceptible to treatment with a GDF-8 agent (e.g., a suppressing or enhancing agent). One such disorder is a malignant cell proliferative disorder, for example.

An antibody that specifically binds a GDF-8 polypeptide can be labeled with a compound which allows detection of binding to GDF-8. Such an antibody can be used to detect the level of GDF-8 in biological fluids and tissues. Any specimen containing a detectable amount of antigen can be used. A preferred sample of this invention is muscle tissue. The level of GDF-8 in the suspect cell sample can be compared with the level in a normal cell sample to determine whether the subject has a GDF-8-associated cell proliferative disorder. Alternatively, GDF-8 nucleic acid can be detected, for example, by northern blot analysis, to determine the level of mRNA transcribed from GDF-8 polynucleotide.

The antibodies of the invention can be used in any subject in which it is desirable to utilize in vitro or in vivo immunodiagnosis or immunotherapy. The antibodies of the invention are suited for use, for example, in immunoassays in which they can be utilized in liquid phase or bound to a solid phase carrier. In addition, the antibodies in these immunoassays can be detectably labeled in various ways. Examples of types of immunoassays which can utilize antibodies of the invention are competitive and non-competitive immunoassays in either a direct or indirect format. Examples of such immunoassays are the radioimmunoassay (RIA) and the sandwich (immunometric) assay. Detection of the antigens using the antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The antibodies of the invention can be bound to many different carriers and used to detect the presence of an antigen comprising the polypeptide of the invention. Examples of well known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, phosphorescent compounds, and bioluminescent compounds. Those in the art will know of other suitable labels for binding to the antibody, or will be able to ascertain such, using routine experimentation.

Another technique which can also result in greater detection sensitivity consists of coupling the antibodies to low molecular weight haptens. These haptens can then be specifically detected by means of a second reaction. For example, it is common to use such haptens as biotin, which reacts with avidin, or dinitrophenyl, puridoxal, and fluorescein, which can react with specific anti-hapten antibodies.

In using the monoclonal antibodies of the invention for the in vivo detection of antigen, the detectably labeled antibody is given a dose which is diagnostically effective. The term "diagnostically effective" means that the amount of detectably labeled monoclonal antibody is administered in sufficient quantity to enable detection of the site having the antigen comprising a polypeptide of the invention for which the monoclonal antibodies are specific.

The concentration of detectably labeled monoclonal antibody which is administered should be sufficient such that the binding to those cells having the polypeptide is detectable compared to the background. Further, it is desirable that the detectably labeled monoclonal antibody be rapidly cleared from the circulatory system in order to give the best target-to-background signal ratio. In general, the dosage of detectably labeled monoclonal antibody for in vivo diagnosis will vary depending on such factors as age, sex, and extent of disease of the individual. Such dosages can vary, for example, depending on whether multiple injections are given, antigenic burden, and other factors known to those of skill in the art.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that deleterious radiation with respect to the host is minimized. Ideally, a radioisotope used for in vivo imaging will lack a particle emission, but produce a large number of photons in the 140-250 keV range, which can readily be detected by conventional gamma cameras.

For in vivo diagnosis, radioisotopes can be bound to immunoglobulin either directly or indirectly by using an intermediate functional group. intermediate functional groups which often are used to bind radioisotopes which exist as metallic ions to immunoglobulins are the bifunctional chelating agents such as diethylene triaminepentacetic acid (DTPA) and ethylenediaminetetraacetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr, and $^{56}$Fe.

The monoclonal antibodies of the invention can be used in vitro and in vivo to monitor the course of amelioration of a GDF-8-associated disease in a subject. Thus, for example, by measuring the increase or decrease in the number of cells expressing antigen comprising a polypeptide of the invention or changes in the concentration of such antigen present in various body fluids, it would be possible to determine whether a particular therapeutic regimen aimed at ameliorating the GDF-8-associated disease is effective. The term "ameliorate" denotes a lessening of the detrimental effect of the GDF-8-associated disease in the subject receiving therapy.

The present invention identifies polynucleotide sequences that can be expressed in an altered manner as compared to expression in a normal cell. Thus, it is possible to design appropriate therapeutic or diagnostic techniques directed to this polynucleotide sequence. Treatment includes administration of a reagent which modulates GDF-8 levels or activity. The term "modulate" encompasses the suppression or expression of GDF-8 when it is overexpressed, or augmentation of GDF-8 expression when it is underexpressed. When a muscle-associated disorder is associated with GDF-8 overexpression, such suppressive reagents as antisense GDF-8 polynucleotide sequence or GDF-8 binding antibody can be introduced into a cell. In addition, an anti-idiotype antibody which binds to a monoclonal antibody which binds GDF-8 of the invention, or an epitope thereof, can also be used in the therapeutic method of the invention. Alternatively, when a cell proliferative disorder is associated with underexpression or overexpression of a mutant GDF-8 polypeptide, a sense polynucleotide sequence (the DNA coding strand) or GDF-8 polypeptide can be introduced into the cell. Such muscle-associated disorders include cancer, muscular dystrophy, spinal cord injury, traumatic injury, congestive obstructive pulmonary disease (COPD), AIDS or cachexia.

Thus, where a cell proliferative disorder is associated with the expression of GDF-8, nucleic acid sequences that interfere with GDF-8 expression at the translational level can be used. This approach utilizes, for example, antisense nucleic acid and ribozymes to block translation of a specific GDF-8 mRNA, either by masking that mRNA with an antisense nucleic acid or by cleaving it with a ribozyme. Such disorders include neurodegenerative diseases, for example. In addition, dominant-negative GDF-8 mutants can be used to actively interfere with the normal function of native GDF-8 in a cell.

As disclosed herein, antisense molecules, ribozymes or triplexing agents can be useful in performing the methods of the invention. For example, the polynucleotide can be (or can encode) an antisense GDF-8 nucleotide sequence that acts as an antagonist of GDF-8 protein expression, thereby increasing the muscle mass or decreasing the fat content of an organism. Such polynucleotides can be contacted directly with a target cell and, upon uptake by the cell, can effect their antisense, ribozyme or triplexing activity; or can be encoded by a polynucleotide that is introduced into a cell, whereupon the polynucleotide is expressed to produce, for example, an antisense RNA molecule or ribozyme, which effects its activity.

An antisense polynucleotide, ribozyme or triplexing agent is complementary to a target sequence, which can be a DNA or RNA sequence, for example, messenger RNA, and can be a coding sequence, a nucleotide sequence comprising an intron-exon junction, a regulatory sequence such as a Shine-Delgarno sequence, or the like. The degree of complementarity is such that the polynucleotide, for example, an antisense polynucleotide, can interact specifically with the target sequence in a cell. Depending on the total length of the antisense or other polynucleotide, one or a few mismatches with respect to the target sequence can be tolerated without losing the specificity of the polynucleotide for its target sequence. Thus, few if any mismatches would be tolerated in an antisense molecule consisting, for example, of 20 nucleotides, whereas several mismatches will not affect the hybridization efficiency of an antisense molecule that is complementary, for example, to the full length of a target mRNA encoding a cellular polypeptide. The number of mismatches that can be tolerated can be estimated, for example, using well known formulas for determining hybridization kinetics (see Sambrook et al., supra, 1989) or can be determined empirically using methods as disclosed herein or otherwise known in the art, particularly by determining that the presence of the antisense polynucleotide, ribozyme, or triplexing agent in a cell decreases the level of the target sequence or the expression of a polypeptide encoded by the target sequence in the cell.

A polynucleotide useful as an antisense molecule, a ribozyme or a triplexing agent can inhibit translation or cleave the target nucleic acid molecule, thereby decreasing the levels of GDF-8 in cells. An antisense molecule, for example, can bind to an mRNA to form a double stranded molecule that cannot be translated in a cell. Antisense oligonucleotides of at least about 15 to 25 nucleotides are preferred because they are easily synthesized and can hybridize specifically with a target sequence, although longer antisense molecules can be expressed from a polynucleotide introduced into the target cell. Specific nucleotide sequences useful as antisense molecules can be identified using well known methods, for example, gene walking methods (see, for example, Seimiya et al., *J. Biol. Chem.* 272:4631-4636 (1997), which is incorporated herein by reference). Where the antisense molecule is contacted directly with a target cell, it can be operatively associated with a chemically reactive group such as iron-linked EDTA, which cleaves a target RNA at the site of hybridization. A triplexing agent, in comparison, can stall transcription (Maher et al., *Antisense Res. Devel.* 1:227 (1991); Helene, *Anticancer Drug Design* 6:569 (1991)). Thus, a triplexing agent can be designed to recognize a sequence of a GDF-8 gene regulatory element, thereby reducing or inhibiting the expression of GDF-8 polypeptide in the cell.

Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double stranded molecule. The antisense nucleic acids interfere with the translation of the mRNA, since the cell will not translate a mRNA that is double stranded.

Antisense oligomers of about 15 nucleotides are preferred, since they are easily synthesized and are less likely to cause problems than larger molecules when introduced into the target GDF-8-producing cell. The use of antisense methods to inhibit the in vitro translation of genes is well known in the art (Marcus-Sakura, Anal. Biochem., 172:289, 1988).

Ribozymes are RNA molecules possessing the ability to specifically cleave other single stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences which are four bases in length, while "hammerhead"-type ribozymes recognize base sequences 11 to 18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18 base recognition sequences are preferable to shorter recognition sequences.

The present invention also provides gene therapy for the treatment of cell proliferative or immunologic disorders which are mediated by GDF-8. Such therapy achieves its therapeutic effect by introduction of the GDF-8 antisense polynucleotide into cells exhibiting or associated with the proliferative disorder. Delivery of antisense GDF-8 polynucleotide can be achieved using a recombinant expression vector such as a chimeric virus or a colloidal dispersion system. Especially preferred for therapeutic delivery of antisense oligonucleotide sequences is the use of targeted liposomes. In contrast, when it is desirable to enhance GDF-8 production, GDF-8 polynucleotide is introduced into the appropriate cell or cells.

Various viral vectors that can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to, Moloney murine leukemia virus, Harvey murine sarcoma virus, murine mammary tumor virus, and Rous sarcoma virus. A number of additional retroviral vectors can incorporate multiple genes. All of these vectors can transfer or incorporate a gene for a selectable marker so that transduced cells can be identified and generated. By inserting a GDF-8 polynucleotide sequence of interest into the viral vector, along with another polynucleotide encoding a ligand for a receptor on a specific target cell, the vector is rendered target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the GDF-8 antisense polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsulation. Helper cell lines which have deletions of the packaging signal include, but are not limited to $\psi 2$, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for GDF-8 antisense polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 µm can encapsulate a substantial percentage of an aqueous buffer containing large macromolecules. RNA, DNA and intact virions can be encapsulated within the aqueous interior and be delivered to cells in a biologically active form (Fraley et al., Trends Biochem. Sci., 6:77, 1981). In addition to mammalian cells, liposomes have been used for delivery of polynucleotides in plant, yeast and bacterial cells. in order for a liposome to be an efficient gene transfer vehicle, the following characteristics should be present: 1) encapsulation of the genes of interest at high efficiency while not compromising their biological activity; 2) preferential and substantial binding to a target cell in comparison to non-target cells; 3) delivery of the aqueous contents of the vesicle to the target cell cytoplasm at high efficiency; and 4) accurate and effective expression of genetic information (Manning et al., BioTechniques, 6:682, 1988).

The composition of the liposome is usually a combination of phospholipids, particularly high-phase-transition-temperature phospholipids, usually in combination with steroids, especially cholesterol. Other phospholipids or other lipids can also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system can be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Due to the expression of GDF-8 in muscle and adipose tissue, there are a variety of applications using the polypeptide, polynucleotide, and antibodies of the invention, related to these tissues. Such applications include treatment of cell proliferative disorders involving these and other tissues, such as neural tissue. In addition, GDF-8 can be useful in various gene therapy procedures. In embodiments where GDF-8 polypeptide is administered to a subject, the dosage range is about 0.1 µg/kg to 100 mg/kg; more preferably from about 1 µg/kg to 75 mg/kg and most preferably from about 10 mg/kg to 50 mg/kg.

The human GDF-8 gene is located on chromosome 2 (see Example 6). By comparing the chromosomal location of GDF-8 with the map positions of various human disorders, a role for mutations in the GDF-8 gene in the etiology of human diseases can be determined. For example, an autosomal recessive form of juvenile amyotrophic lateral sclerosis maps to chromosome 2 (Hentati et al., Neurology, 42, Suppl. 3:201, 1992). More precise mapping of GDF-8 and analysis of DNA from these patients can confirm that GDF-8 is, in fact, the gene affected in this disease. In addition, GDF-8 is useful for distinguishing chromosome 2 from other chromosomes.

The present invention also provides transgenic non-human animals, particularly transgenic aquatic organisms, expressing altered levels of GDF-8 as compared to the level normally expressed by a corresponding non-transgenic animal. Various methods to make the transgenic animals of the subject invention can be employed. Generally speaking, three such methods can be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191, and can be adapted for purposes of the present invention. In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, a recently published procedure by Love et al., (Biotechnology, 12, January 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

A non-human transgenic animal of the invention can be a bovine, porcine, or ovine, or an avian animal, and preferably is an aquatic organism such as a piscine, which can be produced by introducing a transgene into the germline of the animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal containing exogenous genetic material within all of its cells. A transgenic animal can be produced by cross-breeding two chimeric animals containing the exogenous genetic material in their reproductive cells. Twenty-five percent of the resulting offspring will be transgenic, i.e., animals which include the exogenous genetic material within all of their cells in both alleles. Fifty percent of the resulting animals will include the exogenous genetic material within one allele and 25% will include no exogenous genetic material.

In the microinjection method useful in the practice of the subject invention, the transgene is digested and purified free from any vector DNA, for example, by gel electrophoresis. It is preferred that the transgene include an operatively associated promoter which interacts with cellular proteins involved in transcription, ultimately resulting in constitutive expression. Promoters useful in this regard include those from cytomegalovirus, Moloney leukemia virus, or herpes virus, as well as those from the genes encoding metallothionein, skeletal actin, phosphoenolpyruvate carboxylase, phosphoglycerate, dihydrofolate reductase, and thymidine kinase. Promoters for viral long terminal repeats such as Rous sarcoma virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce the transgene into a non-human animal, as described above. The developing non-human embryo can be cultured in vitro to the blastocyst stage. During this time, the blastomeres can be targets for retroviral infection (Jaenich, Proc. Natl. Acad. Sci USA 73:1260-1264, 1976). Efficient infection of the blastomeres is obtained by enzymatic treatment to remove the zona pellucida (Hogan et al. (1986) in Manipulating the Mouse Embryo, Cold Spring Harbor Laboratory Press, Cold Spring Harbor N.Y.). The viral vector system used to introduce the transgene is typically a replication-defective retrovirus carrying the transgene (Jahner et al., Proc. Natl. Acad. Sci. USA 82:6927-6931, 1985; Van der Putten et al., Proc. Natl. Acad. Sci USA 82:6148-6152, 1985). Transfection is easily and efficiently obtained by culturing the blastomeres on a monolayer of virus producing cells (Van der Putten, supra, 1985; Stewart et al., EMBO J. 6:383-388, 1987). Alternatively, infection can be performed at a later stage. Virus or virus producing cells can be injected into the blastocoele (Jahner et al., Nature 298:623-628, 1982). Most of the founders will be mosaic for the transgene since incorporation occurs only in a subset of the cells which formed the transgenic nonhuman animal. Further, the founder can contain various retroviral insertions of the transgene at different positions in the genome which generally will segregate in the offspring. In addition, it is also possible to introduce transgenes into the germ line, albeit with low efficiency, by intrauterine retroviral infection of the midgestation embryo (Jahner et al., supra, 1982).

A third type of target cell for transgene introduction is the embryonal stem cell (ES). ES cells are obtained from pre-implantation embryos cultured in vitro and fused with embryos (Evans et al. Nature 292:154-156, 1981; Bradley et al., Nature 309: 255-258, 1984; Gossler et al., Proc. Natl. Acad. Sci USA 83: 9065-9069, 1986; and Robertson et al., Nature 322:445-448, 1986). Transgenes can be efficiently introduced into the ES cells by DNA transfection or by retrovirus mediated transduction. Such transformed ES cells can thereafter be combined with blastocysts from a nonhuman animal. The ES cells thereafter colonize the embryo and contribute to the germ line of the resulting chimeric animal (for review, see Jaenisch, Science 240:1468-1474, 1988). As used in reference to transgenic animals, the term "transformed" means a cell into which (or into an ancestor of which) has been introduced, by means of recombinant nucleic acid techniques, a heterologous nucleic acid molecule; and the term "heterologous" means a polynucleotide that either originates from another species or is modified from either its original form or the form primarily expressed in the cell.

The term "transgene" is used to refer to any polynucleotide that is inserted by artifice into a cell, and becomes part of the genome of the organism (i.e., either stably integrated or as a stable extrachromosomal element) that develops from the cell. A transgene can be a gene, which is partly or entirely heterologous (i.e., foreign) to the transgenic organism, or can represent a gene homologous to an endogenous gene of the organism. Included within this definition is a transgene created by providing an RNA sequence that is transcribed into DNA and incorporated into the genome. The transgenes of the invention include polynucleotide encoding GDF-8, either sense or antisense polynucleotides, which can be expressed in a transgenic non-human animal.

The term "transgenic" as used herein additionally includes any non-human organism, particularly an aquatic organism, whose genome has been altered by in vitro manipulation of the early embryo or fertilized egg or by any transgenic technology to induce a specific gene knockout. The term "gene knockout" refers to the targeted disruption of a gene in vivo with complete loss of function that has been achieved by any transgenic technology familiar to those in the art. In one embodiment, transgenic animals having gene knockouts are those in which the target gene has been rendered nonfunctional by an insertion targeted to the gene to be rendered non-functional by homologous recombination. As used herein, the term "transgenic" includes any transgenic technology familiar to those in the art which can produce a non-human organism carrying an introduced transgene or one in which an endogenous gene has been rendered non-functional or "knocked out."

The transgene to be used in the practice of the subject invention is a polynucleotide comprising a modified GDF-8 coding sequence. In a preferred embodiment, the endogenous GDF-8 gene is disrupted by homologous targeting in embryonic stem cells. For example, the entire mature C-terminal region of the GDF-8 gene can be deleted as described below (see Example 8). Optionally, the GDF-8 disruption or deletion can be accompanied by insertion of or replacement with another polynucleotide, such as a non-functional GDF-8 sequence (e.g., encoding a dominant negative GDF-8 polypeptide). In other embodiments, the transgene comprises an antisense molecule to a portion of a GDF-8 gene or transcript. In another embodiment, the transgene comprises DNA encoding an antibody or receptor peptide sequence that can specifically bind GDF-8. The polynucleotide and polypeptide sequences of GDF-8 are disclosed herein or otherwise known in the art, as are their cellular localization and activity (see, for example, Intl. Publ. WO94/21681, which is incorporated herein by reference). Where appropriate, polynucleotides that encode proteins having GDF-8 activity but differ in nucleic acid sequence due to the degeneracy of the genetic code can also be used herein, as can truncated forms, allelic variants and interspecies homologues.

In a particular embodiment, the transgenic organisms of the invention are aquatic organisms. Methods for producing transgenic aquatic organisms, such as finfish, mollusks, and the like are known in the art (see, for example, U.S. Pat. No. 5,675,061, transgenic abalone; U.S. Pat. No. 5,545,808, transgenic salmon; see, also, Hackett, "The Molecular Biology of Transgenic Fish" in Molecular Biology of Fishers, Vol. 2 (Hochachka and Mommsen, eds. 1993); Hahn, in Handbook of Culture of Abalone and Other Marine Gastropods (Hahn, ed., CRC Press, Inc., Boca Raton Fla. 1989) see pages 71-98; Moav, et al., in "Expression of Heterologous Genes in Transgenic Fish" in Transgenic Fish (Hew, ed. World Scientific Publishing Co., Singapore, 1992a) see pages 120-141; Chen et al. (1990) "Gene transfer, expression and inheritance of rainbow trout and human growth hormone genes in carp and loach" in "Transgenic Models in Medicine and Agriculture" (Wiley-Liss, Inc.), pages 127-139; Chen and Evans, BioTechniques, 8:32-33, 1990; Chong and Vielkind, Theor. Appl. Genet. 78: 369-380 (1989); Davies et al., in "Methods in Molecular Biology" (Elsevier Science Publishing Co. 1986); Davies et al., "Fish antifreeze protein genes and their use in transgenic studies" in "Oxford Surveys on Eukaryotic Genes" 6:85-110 (ed. Norman Maclean, Oxford University Press 1989); each of which is incorporated herein by reference.

The transgenic organisms of the invention also include those having heterozygous mutations in an GDF-8 gene. A heterozygous transgenic has an intermediate increase in muscle mass as compared to an organism having a homozygous disruption (maximum increase) or a wild-type organism (normal muscle) not having an interrupted GDF-8.

After an embryo has been microinjected, colonized with transfected embryonic stem cells or infected with a retrovirus containing the transgene (except for practice of the subject invention in avian species which is addressed elsewhere herein) the embryo is implanted into the oviduct of a pseudopregnant female. The consequent progeny are tested for incorporation of the transgene by Southern blot analysis of blood samples using transgene specific probes. PCR is particularly useful in this regard. Positive progeny (G0) are crossbred to produce offspring (G1), which are analyzed for transgene expression by northern blot analysis of tissue samples. To facilitate distinguishing expression of like-species transgenes from expression of the endogenous GDF-8 gene(s) in a transgenic animal, a marker gene fragment can be included in the construct in the 3' untranslated region of the transgene and the northern blot probe can be designed to detect the marker gene fragment. The serum levels of GDF-8 can also be measured in the transgenic animal to establish appropriate expression. Expression of the GDF-8 transgenes, thereby decreasing the GDF-8 in the tissue and serum levels of the transgenic animals and consequently increasing the muscle tissue content results in the foodstuffs from these animals (i.e., eggs, beef, pork, fish, poultry meat, milk, etc.) having markedly increased muscle content, and preferably without increased, and more preferably, reduced levels of fat and cholesterol. By practice of the subject invention, a statistically significant increase in muscle content, preferably at least a 2% increase in muscle content (e.g., in chickens), more preferably a 25% increase in muscle content as a percentage of body weight, more preferably greater than 40% increase in muscle content in these foodstuffs can be obtained.

Thus, the present invention includes methods for increasing muscle mass in domesticated or commercially valuable animals characterized by inactivation or deletion of the gene encoding GDF-8. The domesticated or commercially valuable animal can be an ovine, bovine, porcine, or avian species, and preferably is an aquatic organism such as a piscine. The animal can be treated with an isolated polynucleotide sequence encoding GDF-8, wherein the polynucleotide sequence is also from a domesticated or commercially valuable animal selected from an ovine, bovine, porcine, or avian species, an aquatic organism such as a piscine species, or is from any other species.

The present invention further includes methods for increasing the muscle mass in such animals by administering to the animal antibodies that specifically bind a GDF-8 polypeptide, preferably an antibody that specifically binds an aquatic organism GDF-8. The antibody can be an anti-GDF-8 antibody, and can be either a monoclonal antibody or a polyclonal antibody. The invention also includes methods of using an anti-GDF-8 monoclonal antibody as a therapeutic agent to inhibit the growth regulating actions of GDF-8 on muscle cells. Muscle cells are defined to include fetal or adult muscle cells, as well as progenitor cells which are capable of differentiation into muscle. As discussed above, the monoclonal antibody can be a humanized (e.g., either fully or a chimeric) monoclonal antibody, or of any species origin, such as murine, ovine, bovine, porcine or avian. Methods of producing antibody molecules with various combinations of "humanized" antibodies are well known in the art and include combining murine variable regions with human constant regions (Cabily et al. Proc. Natl. Acad. Sci. USA, 81:3273, 1984), or by grafting the murine-antibody complementary determining regions (CDRs) onto the human framework (Richmann et al., Nature 332:323, 1988). Other general references which teach methods for creating humanized antibodies include Morrison et al., Science, 229:1202, 1985; Jones et al., Nature, 321:522, 1986; Monroe et al., Nature 312:779, 1985; Oi et al., BioTechniques, 4:214, 1986; European Patent Application No. 302,620; and U.S. Pat. No. 5,024,834. Therefore, by humanizing the monoclonal antibodies of the invention for in vivo use, an immune response to the antibodies would be greatly reduced.

A monoclonal antibody, GDF-8 polypeptide, or GDF-8 polynucleotide (all GDF-8 agents) can have the effect of increasing the development of skeletal muscles. In preferred embodiments of the claimed methods, the GDF-8 monoclonal antibody, polypeptide, or polynucleotide is administered to a patient suffering from a disorder such as a muscle wasting disease, neuromuscular disorder, or muscle atrophy, or from aging. The GDF-8 agent can also be administered to a patient suffering from a disorder such as muscular dystrophy, spinal cord injury, traumatic injury, congestive obstructive pulmonary disease (COPD), AIDS or cachexia. In a preferred embodiment, the GDF-8 agent is administered to a patient with muscle wasting disease or disorder by intravenous, intramuscular or subcutaneous injection; preferably, a monoclonal antibody is administered within a dose range between about 0.1 mg/kg to about 100 mg/kg; more preferably between about 1 μg/kg to 75 mg/kg; most preferably from about 10 mg/kg to 50 mg/kg. The antibody can be administered, for example, by bolus injunction or by slow infusion. Slow infusion over a period of 30 minutes to 2 hours is preferred. The GDF-8 agent can be formulated in a formulation suitable for administration to a patient. Such formulations are known in the art.

The dosage regimen will be determined by the attending physician considering various factors which modify the action of the GDF-8 protein, e.g., amount of tissue desired to be formed, the site of tissue damage, the condition of the damaged tissue, the size of a wound, type of damaged tissue, the patient's age, sex, and diet, the severity of any infection, time of administration and other clinical factors. The dosage can vary with the type of matrix used in the reconstitution and the types of agent, such as anti-GDF-8 antibodies, to be used in the composition. Generally, systemic or injectable administration, such as intravenous, intramuscular or subcutaneous injection. Administration will generally be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that appears. The addition of other known growth factors, such as insulin like growth factor-1, or human, bovine, or chicken growth hormone, which can aid in increasing muscle mass, to the final composition or prior to or after the GDF-8 agent, can also affect the dosage. In the embodiment where an anti-GDF-8 antibody is administered, the anti-GDF-8 antibody is generally administered within a dose range of about 0.1 µg/kg to about 100 mg/kg.; more preferably between about 10 mg/kg to 50 mg/kg.

Progress can be monitored by periodic assessment of tissue growth and/or repair. The progress can be monitored, for example, X-rays, histomorphometric determinations and tetracycline labeling.

All references cited herein are hereby incorporated by reference in their entirety.

The following examples are intended to illustrate but not limit the invention. While they are typical of those that might be used, other procedures known to those skilled in the art can alternatively be used.

EXAMPLE 1

Identification and Isolation of a Novel TGF-β Family Member

To identify a new member of the TGF-β superfamily, degenerate oligonucleotides were designed which corresponded to two conserved regions among the known family members: one region spanning the two tryptophan residues conserved in all family members except MIS and the other region spanning the invariant cysteine residues near the C-terminus. These primers were used for polymerase chain reactions on mouse genomic DNA followed by subcloning the PCR products using restriction sites placed at the 5' ends of the primers, picking individual E. coli colonies carrying these subcloned inserts, and using a combination of random sequencing and hybridization analysis to eliminate known members of the superfamily.

GDF-8 was identified from a mixture of PCR products obtained with the primers:

```
SJL141:                          (SEQ ID NO: 1)
5'-CCGGAATTCGGITGG(G/C/A)A(G/A/T/C)(A/G)A(T/C)
TGG(A/G)TI(A/G)TI(T/G)CICC-3'

SJL147:                          (SEQ ID NO: 2)
5'-CCGGAATTC(G/A)CAI(G/C)C(G/A)CA(G/A)CT(GIA/T/C)
TCIACI(G/A)(T/C)CAT-3'
```

PCR using these primers was carried out with 2 µg mouse genomic DNA at 94° C. for 1 min, 50° C. for 2 min, and 72° C. for 2 min for 40 cycles.

PCR products of approximately 280 bp were gel purified, digested with Eco RI, gel purified again, and subcloned in the pBluescript vector (Stratagene, San Diego, Calif.). Bacterial colonies carrying individual subclones were picked into 96 well microtiter plates, and multiple replicas were prepared by plating the cells onto nitrocellulose. The replicate filters were hybridized to probes representing known members of the family, and DNA was prepared from non-hybridizing colonies for sequence analysis.

The primer combination of SJL141 and SJL147, encoding the amino acid sequences GW(H/Q/N/K/D/E)(D/N)W(V/I/M)(V/I/M)(A/S)P (SEQ ID NO:9) and M(V/I/M/T/A)V(D/E)SC(G/A)C (SEQ ID NO:10), respectively, yielded four previously identified sequences (BMP-4, inhibin-β, GDF-3 and GDF-5) and one novel sequence, which was designated GDF-8, among 110 subclones analyzed.

Human GDF-8 was isolated using the primers:

```
                                 (SEQ ID NO:3)
ACM13:  5'-CGCGGATCCAGAGTCAAGGTGACAGACACAC-3';
and
                                 (SEQ ID NO:4)
ACM14:  5'-CGCGGATCCTCCTCATGAGCACCCACAGCGGTC-3'
```

PCR using these primers was carried out with one µg human genomic DNA at 94° C. for 1 min, 58° C. for 2 min, and 72° C. for 2 min for 30 cycles. The PCR product was digested with Bam HI, gel purified, and subcloned in the pBluescript vector (Stratagene, San Francisco, Calif.).

EXAMPLE 2

Expression Pattern and Sequence of GDF-8

To determine the expression pattern of GDF-8, RNA samples prepared from a variety of adult tissues were screened by northern blot analysis. RNA isolation and northern blot analysis were carried out as described previously (Lee, Mol. Endocrinol., 4:1034, 1990) except that hybridization was carried out in 5×SSPE, 10% dextran sulfate, 50% formamide, 1% SDS, 200 µg/ml salmon DNA, and 0.1% each of bovine serum albumin, ficoll, and polyvinylpyrrolidone. Five micrograms of twice poly A-selected RNA prepared from each tissue (except for muscle, for which only 2 µg RNA was used) were electrophoresed on formaldehyde gels, blotted, and probed with GDF-8. As shown in FIG. 1, the GDF-8 probe detected a single mRNA species expressed at highest levels in muscle and at significantly lower levels in adipose tissue.

To obtain a larger segment of the GDF-8 gene, a mouse genomic library was screened with a probe derived from the GDF-8 PCR product. The partial sequence of a GDF-8 genomic clone is shown in FIG. 2a. The sequence contains an open reading frame corresponding to the predicted C-terminal region of the GDF-8 precursor protein. The predicted GDF-8 sequence contains two potential proteolytic processing sites, which are boxed. Cleavage of the precursor at the second of these sites would generate a mature C-terminal fragment 109 amino acids in length with a predicted molecular weight of 12,400 Daltons. The partial sequence of human GDF-8 is shown in FIG. 2b. Assuming no PCR-induced errors during the isolation of the human clone, the human and mouse amino acid sequences in this region are 100% identical.

The C-terminal region of GDF-8 following the putative proteolytic processing site shows significant homology to the known members of the TGF-β superfamily (FIG. 3). FIG. 3 shows the alignment of the C-terminal sequences of GDF-8 with the corresponding regions of human GDF-1 (Lee, Proc. Natl. Acad. Sci. USA, 88:4250-4254, 1991), human BMP-2 and 4 (Wozney et al., Science, 242:1528-1534, 1988), human Vgr-1 (Celeste et al. Proc. Natl. Acad. Sci. USA, 87:9843-9847, 1990), human OP-1 (Ozkaynak et al., EMBO J., 9:2085-2093, 1990), human BMP-5 (Celeste et al., Proc. Natl. Acad. Sci. USA, 87:9843-9847, 1990), human BMP-3 (Wozney et al., supra, 1988), human MIS (Cate et al. Cell, 45:685-698,1986), human inhibin-α and inhibin-β (Mason et al., Biochem. Biophys. Res. Comm., 135:957-964, 1986), human TGF-β1 (Derynck et al., Nature, 316:701-705, 1985), human TGF-β2 (deMartin et al., EMBO J., 6:3673-3677, 1987), and human TGF-β3 (ten Dijke et al., Proc. Natl. Acad. Sci. USA, 85:4715-4719, 1988). The conserved cysteine residues are boxed. Dashes denote gaps introduced in order to maximize the alignment.

GDF-8 contains most of the residues that are highly conserved in other family members, including the seven cysteine residues with their characteristic spacing. Like the TGF-βs and inhibin βs, GDF-8 also contains two additional cysteine residues. In the case of TGF-β2, these two additional cysteine residues are known to form an intramolecular disulfide bond (Daopin et al., Science, 257:369, 1992; Schlunegger and Grutter, Nature, 358:430, 1992).

FIG. 4 shows the amino acid homologies among the different members of the TGF-β superfamily. Numbers represent percent amino acid identities between each pair calculated from the first conserved cysteine to the C terminus. Boxes represent homologies among highly-related members within particular subgroups. In this region, GDF-8 is most homologous to Vgr-1 (45% sequence identity).

EXAMPLE 3

Isolation of cDNA Clones Encoding Murine and Human GDF-8

In order to isolate full length cDNA clones encoding murine and human GDF-8, cDNA libraries were prepared in the lambda ZAP II vector (Stratagene) using RNA prepared from skeletal muscle. From 5 µg of twice poly A-selected RNA prepared from murine and human muscle, cDNA libraries consisting of 4.4 million and 1.9 million recombinant phage, respectively, were constructed according to the instructions provided by Stratagene. These libraries were screened without amplification. Library screening and characterization of cDNA inserts were carried out as described previously (Lee, Mol. Endocrinol., 4:1034-1040).

Figure 6A:
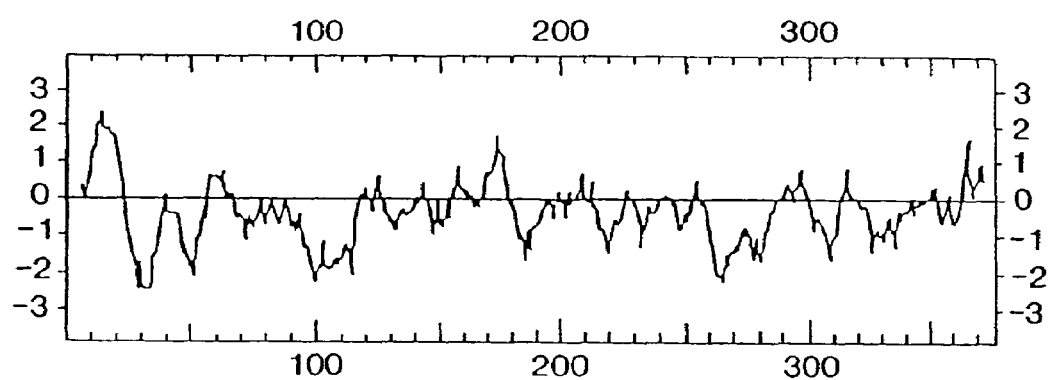
FIGS. 6a and 6b show a hydropathicity profile of GDF-8. Average hydrophobicity values for murine (FIG. 6a) and human (FIG. 6b) GDF-8 were calculated using the method of Kyte and Doolittle (J. Mol. Biol., 157:105-132, 1982). Positive numbers indicate increasing hydrophobicity.

From $2.4 \times 10^6$ recombinant phage screened from the murine muscle cDNA library, greater than 280 positive phage were identified using a murine GDF-8 probe derived from a genomic clone, as described in Example 1. The entire nucleotide sequence of the longest cDNA insert analyzed is shown in FIG. 5a and SEQ ID NO:11. The 2676 base pair sequence contains a single long open reading frame beginning with a methionine codon at nucleotide 104 and extending to a TGA stop codon at nucleotide 1232. Upstream of the putative initiating methionine codon is an in-frame stop codon at nucleotide 23. The predicted pre-pro-GDF-8 protein is 376 amino acids in length. The sequence contains a core of hydrophobic amino acids at the N-terminus suggestive of a signal peptide for secretion (FIG. 6a), one potential N-glycosylation site at asparagine 72, a putative RXXR proteolytic cleavage site at amino acids 264-267, and a C-terminal region showing significant homology to the known members of the TGF-β superfamily. Cleavage of the precursor protein at the putative RXXR site would generate a mature C-terminal GDF-8 fragment 109 amino acids in length with a predicted molecular weight of approximately 12,400 Daltons.

Figure 6B:
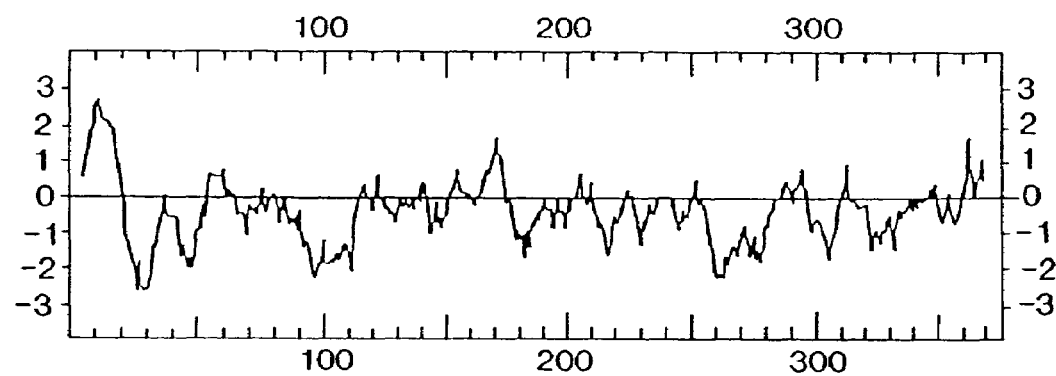

From $1.9 \times 10^6$ recombinant phage screened from the human muscle cDNA library, 4 positive phage were identified using a human GDF-8 probe derived by polymerase chain reaction on human genomic DNA. The entire nucleotide sequence of the longest cDNA insert is shown in FIGS. 5b and SEQ ID NO:13. The 2743 base pair sequence contains a single long open reading frame beginning with a methionine codon at nucleotide 59 and extending to a TGA stop codon at nucleotide 1184. The predicted pre-pro-GDF-8 protein is 375 amino acids in length. The sequence contains a core of hydrophobic amino acids at the N-terminus suggestive of a signal peptide for secretion (FIG. 6b), one potential N-glycosylation site at asparagine 71, and a putative RXXR proteolytic cleavage site at amino acids 263-266. FIG. 7 shows a comparison of the predicted murine (top) and human (bottom) GDF-8 amino acid sequences. Numbers indicate amino acid position relative to the N-terminus. Identities between the two sequences are denoted by a vertical line. Murine and human GDF-8 are approximately 94% identical in the predicted pro-regions and 100% identical following the predicted RXXR cleavage sites.

EXAMPLE 4

Dimerization Of GDF-8

To determine whether the processing signals in the GDF-8 sequence are functional and whether GDF-8 forms dimers like other members of the TGF-13 superfamily, the GDF-8 cDNA was stably expressed in CHO cells. The GDF-8 coding sequence was cloned into the pMSXND expression vector (Lee and Nathans, J. Biol. Chem., 263:3521, (1988) and transfected into CHO cells. Following G418 selection, the cells were selected in 0.2 µM methotrexate, and conditioned medium from resistant cells was concentrated and electrophoresed on SDS gels. Conditioned medium was prepared by Cell Trends, Inc. (Middletown, Md.). For preparation of anti-GDF-8 serum, the C-terminal region of GDF-8 (amino acids 268 to 376) was expressed in bacteria using the RSET vector (Invitrogen, San Diego, Calif.), purified using a nickel chelate column, and injected into rabbits. All immunizations were carried out by Spring Valley Labs (Woodbine, Md.).

Western blot analysis using (125I)-protein A was carried out as described (Burnette, Anal. Biochem., 112:195, 1981). Western analysis of conditioned medium prepared from these cells using an antiserum raised against a bacterially expressed C-terminal fragment of GDF-8 detected two protein species with apparent molecular weights of approximately 52 kD and 15 kD under reducing conditions, consistent with unprocessed and processed forms of GDF-8, respectively. No bands were obtained either with preimmune serum or with conditioned medium from CHO cells transfected with an antisense construct. Under non-reducing conditions, the GDF-8 antiserum detected two predominant protein species with apparent molecular weights of approximately 101 kD and 25 kD, consistent with dimeric forms of unprocessed and processed GDF-8, respectively. Hence, like other TGF-13 family members, GDF-8 appears to be secreted and proteolytically processed, and the C-terminal region appears to be capable of forming a disulfide-linked dimer.

EXAMPLE 5

Figure 8:
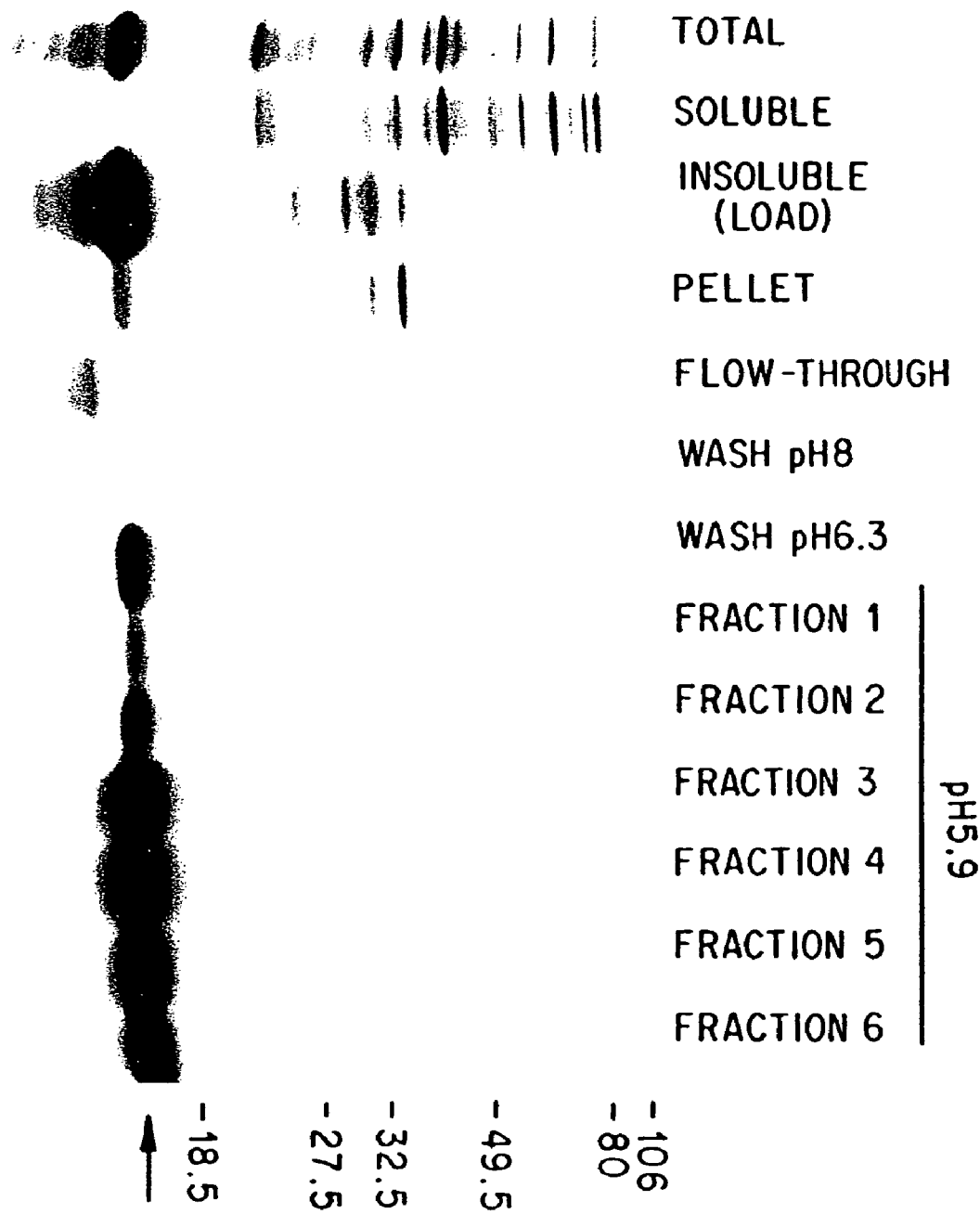
FIG. 8 shows the expression of GDF-8 in bacteria. BL21 (DE3) (pLysS) cells carrying a pRSET/GDF-8 expression plasmid were induced with isopropylthio-N-galactoside, and the GDF-8 fusion protein was purified by metal chelate chromatography. Lanes: total=total cell lysate; soluble=soluble protein fraction; insoluble=insoluble protein fraction (resuspended in 10 Mm Tris pH 8.0, 50 mM sodium phosphate, 8 M urea, and 10 mM β-mercaptoethanol (buffer B)) loaded onto the column; pellet=insoluble protein fraction discarded before loading the column; flowthrough=proteins not bound by the column; washes=washes carried out in buffer B at the indicated pH's. Positions of molecular weight standards are shown at the right. Arrow indicates the position of the GDF-8 fusion protein.

Preparation of Antibodies Against GDF-8 and Expression of GDF-8 in Mammalian Cells In order to prepare antibodies against GDF-8, GDF-8 antigen was expressed as a fusion protein in bacteria. A portion of murine GDF-8 cDNA spanning amino acids 268-376 (mature region) was inserted into the pRSET vector (Invitrogen) such that the GDF-8 coding sequence was placed in frame with the initiating methionine codon present in the vector; the resulting construct created an open reading frame encoding a fusion protein with a molecular weight of approximately 16,600 kD. The fusion construct was transformed into BL21 (DE3) (pLysS) cells, and expression of the fusion protein was induced by treatment with isopropylthio-N-galactoside as described (Rosenberg et al., Gene, 56:125-135). The fusion protein was then purified by metal chelate chromatography according to the instructions provided by Invitrogen. A Coomassie blue stained gel of unpurified and purified fusion proteins is shown in FIG. 8.

The purified fusion protein was used to immunize both rabbits and chickens. Immunization of rabbits was carried out by Spring Valley Labs (Sykesville, Md.), and immunization of chickens was carried out by HRP, Inc. (Denver, Pa.). Western blot analysis of sera both from immunized rabbits and from immunized chickens demonstrated the presence of antibodies directed against the fusion protein.

To express GDF-8 in mammalian cells, the murine GDF-8 cDNA sequence from nucleotides 48-1303 was cloned in both orientations downstream of the metallothionein I promoter in the pMSXND expression vector; this vector contains processing signals derived from SV40, a dihydrofolate reductase gene, and a gene conferring resistance to the antibiotic G418 (Lee and Nathans, J. Biol. Chem., 263: 3521-3527). The resulting constructs were transfected into Chinese hamster ovary cells, and stable transfectants were selected in the presence of G418. Two milliliters of conditioned media prepared from the G418 resistant cells were dialyzed, lyophilized, electrophoresed under denaturing, reducing conditions, transferred to nitrocellulose, and incubated with anti-GDF-8 antibodies (described above) and ($^{125}$I)-protein A.

Figure 9:
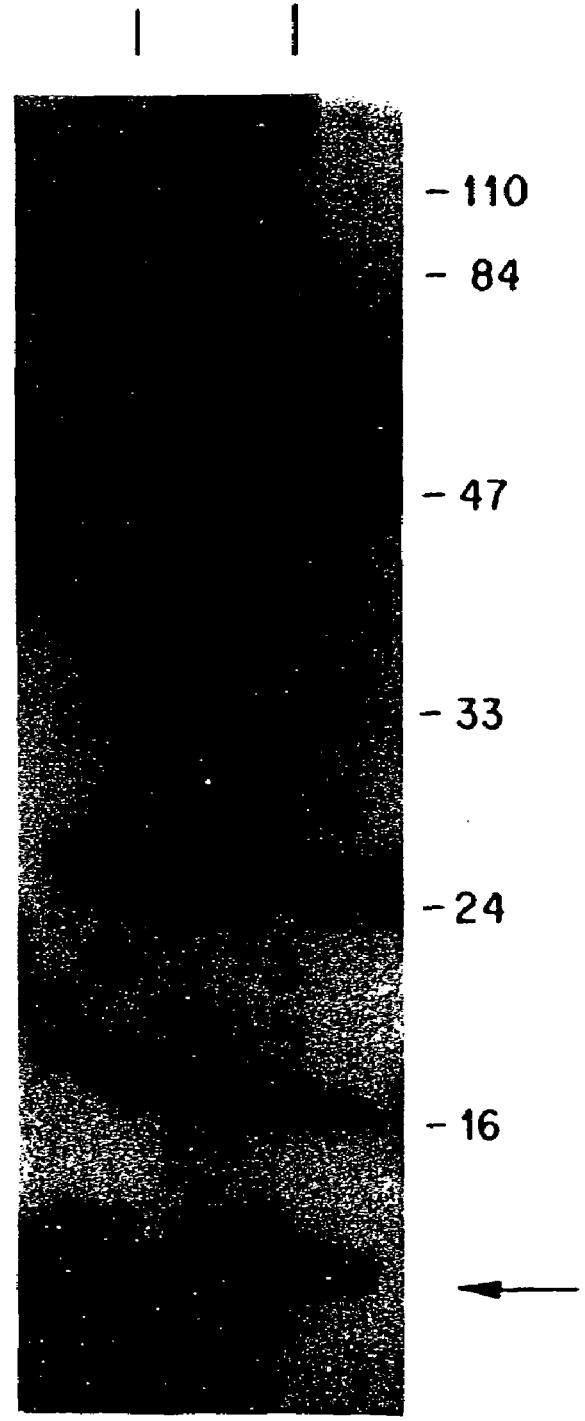
FIG. 9 shows the expression of GDF-8 in mammalian cells. Chinese hamster ovary cells were transfected with pMSXND/GDF-8 expression plasmids and selected in G418. Conditioned media from G418-resistant cells (prepared from cells transfected with constructs in which GDF-8 was cloned in either the antisense or sense orientation) were concentrated, electrophoresed under reducing conditions, blotted, and probed with anti-GDF-8 antibodies and ($^{125}$I)-protein A. Arrow indicates the position of the processed GDF-8 protein.

As shown in FIG. 9, the rabbit GDF-8 antibodies (at a 1:500 dilution) detected a protein of approximately the predicted molecular weight for the mature C-terminal fragment of GDF-8 in the conditioned media of cells transfected with a construct in which GDF-8 had been cloned in the correct (sense) orientation with respect to the metallothionein promoter (lane 2); this band was not detected in a similar sample prepared from cells transfected with a control antisense construct (lane 1). Similar results were obtained using antibodies prepared in chickens. Hence, GDF-8 is secreted and proteolytically processed by these transfected mammalian cells.

EXAMPLE 6

Expression Pattern of GDF-8

Figure 10A:
FIGS. 10a and 10b show the expression of GDF-8 mRNA. Poly A-selected RNA (5 Tg each) prepared from adult tissues (FIG. 10a) or placentas and embryos (FIG. 10b) at the indicated days of gestation was electrophoresed on formaldehyde gels, blotted, and probed with full length murine GDF-8.
Figure 10B:
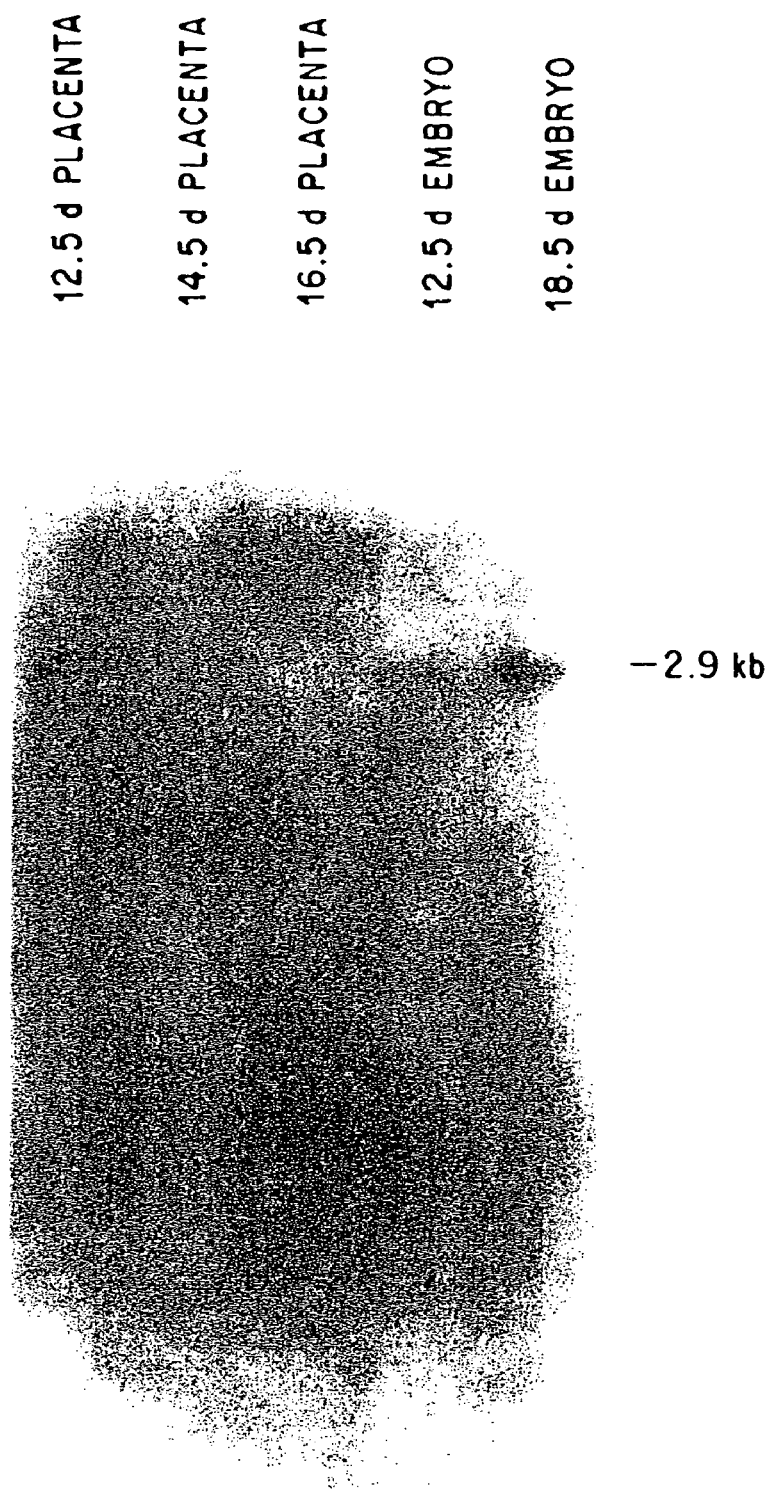

To determine the pattern of GDF-8, 5 µg of twice poly A-selected RNA prepared from a variety of murine tissue sources were subjected to northern blot analysis. As shown in FIG. 10a (and as shown previously in Example 2), the GDF-8 probe detected a single mRNA species present almost exclusively in skeletal muscle among a large number of adult tissues surveyed. On longer exposures of the same blot, significantly lower but detectable levels of GDF-8 mRNA were seen in fat, brain, thymus, heart, and lung. These results confirm the high degree of specificity of GDF-8 expression in skeletal muscle. GDF-8 mRNA was also detected in mouse embryos at both gestational ages (day 12.5 and day 18.5 post-coital) examined but not in placentas at various stages of development (FIG. 10b).

To further analyze the expression pattern of GDF-8, in situ hybridization was performed on mouse embryos isolated at various stages of development. For all in situ hybridization experiments, probes corresponding to the C-terminal region of GDF-8 were excluded in order to avoid possible crossreactivity with other members of the superfamily. Whole mount in situ hybridization analysis was carried out as described (Wilkinson, In Situ Hybridization, A Practical Approach, pages 75-83, IRL Press, Oxford, 1992) except that blocking and antibody incubation steps were carried out as in Knecht et al. (Development, 121:1927, 1955). Alkaline phosphatase reactions were carried out for 3 hours for day 10.5 embryos and overnight for day 9.5 embryos. Hybridization was carried out using digoxigenin-labeled probes spanning nucleotides 8-811 and 1298-2676, which correspond to the pro-region and 3'-untranslated regions, respectively. In situ hybridization to sections was carried out as described (Wilkinson et al., Cell, 50:79, 1987) using $^{35}$S-labelled probes ranging from approximately 100-650 bases in length and spanning nucleotides 8-793 and 1566-2595. Following hybridization and washing, slides were dipped in NTB-3 photographic emulsion, exposed for 16-19 days, developed and stained with either hematoxylin and eosin or toluidine blue. RNA isolation, poly A selection, and northern blot analysis were carried out as described previously (McPherron and Lee, J. Biol. Chem., 268:3444, 1993).

At all stages examined, the expression of GDF-8 mRNA appeared to be restricted to developing skeletal muscle. At early stages, GDF-8 expression was restricted to developing somites. By whole mount in situ hybridization analysis, GDF-8 mRNA could first be detected as early as day 9.5 post coitum in approximately one-third of the somites. At this stage of development, hybridization appeared to be restricted to the most mature (9 out of 21 in this example), rostral somites. By day 10.5 p.c., GDF-8 expression was clearly evident in almost every somite (28 out of 33 in this example shown). Based on in situ hybridization analysis of sections prepared from day 10.5 p.c. embryos, the expression of GDF-8 in somites appeared to be localized to the myotome compartment. At later stages of development, GDF-8 expression was detected in a wide range of developing muscles.

GDF-8 continues to be expressed in adult animals as well. By northern blot analysis, GDF-8 mRNA expression was seen almost exclusively in skeletal muscle among the different adult tissues examined. A significantly lower though clearly detectable signal was also seen in adipose tissue. Based on northern blot analysis of RNA prepared from a large number of different adult skeletal muscles, GDF-8 expression appeared to be widespread although the expression levels varied among individual muscles.

EXAMPLE 7

Chromosomal Localization of GDF-8

In order to map the chromosomal location of GDF-8, DNA samples from human/rodent somatic cell hybrids (Drwinga et al., Genomics, 16:311-413, 1993; Dubois and Naylor, Genomics, 16:315-319, 1993) were analyzed by polymerase chain reaction followed by Southern blotting. Polymerase chain reaction was carried out using primer #83, 5'-CGCGGATCCGTGGATCTAAATGAGAA-CAGTGAGC-3' (SEQ ID NO: 15) and primer #84, 5'-CGC-GAATTCTCAGGTAATGATTGTTTCCGTTGTAGCG-3' (SEQ ID NO:16) for 40 cycles at 94° C. for 2 minutes, 60°

C. for 1 minute, and 72° C. for 2 minutes. These primers correspond to nucleotides 119 to 143 (flanked by a Bam HI recognition sequence), and nucleotides 394 to 418 (flanked by an Eco RI recognition sequence), respectively, in the human GDF-8 cDNA sequence. PCR products were electrophoresed on agarose gels, blotted, and probed with oligonucleotide #100, 5'-ACACTAAATCTTCAAGAATA-3' (SEQ ID NO:17), which corresponds to a sequence internal to the region flanked by primer #83 and #84. Filters were hybridized in 6×SSC, 1× Denhardt's solution, 100 µg/ml yeast transfer RNA, and 0.05% sodium pyrophosphate at 50° C.

As shown in FIG. 11, the human-specific probe detected a band of the predicted size (approximately 320 base pairs) in the positive control sample (total human genomic DNA) and in a single DNA sample from the human/rodent hybrid panel. This positive signal corresponds to human chromosome 2. The human chromosome contained in each of the hybrid cell lines is identified at the top of each of the first 24 lanes (1-22, X, and Y). In the lanes designated M, CHO, and H, the starting DNA template was total genomic DNA from mouse, hamster, and human sources, respectively. In the lane marked B1, no template DNA was used. Numbers at left indicate the mobilities of DNA standards. These data show that the human GDF-8 gene is located on chromosome 2.

EXAMPLE 8

GDF-8 Transgenic Knockout Mice

Figure 12A:
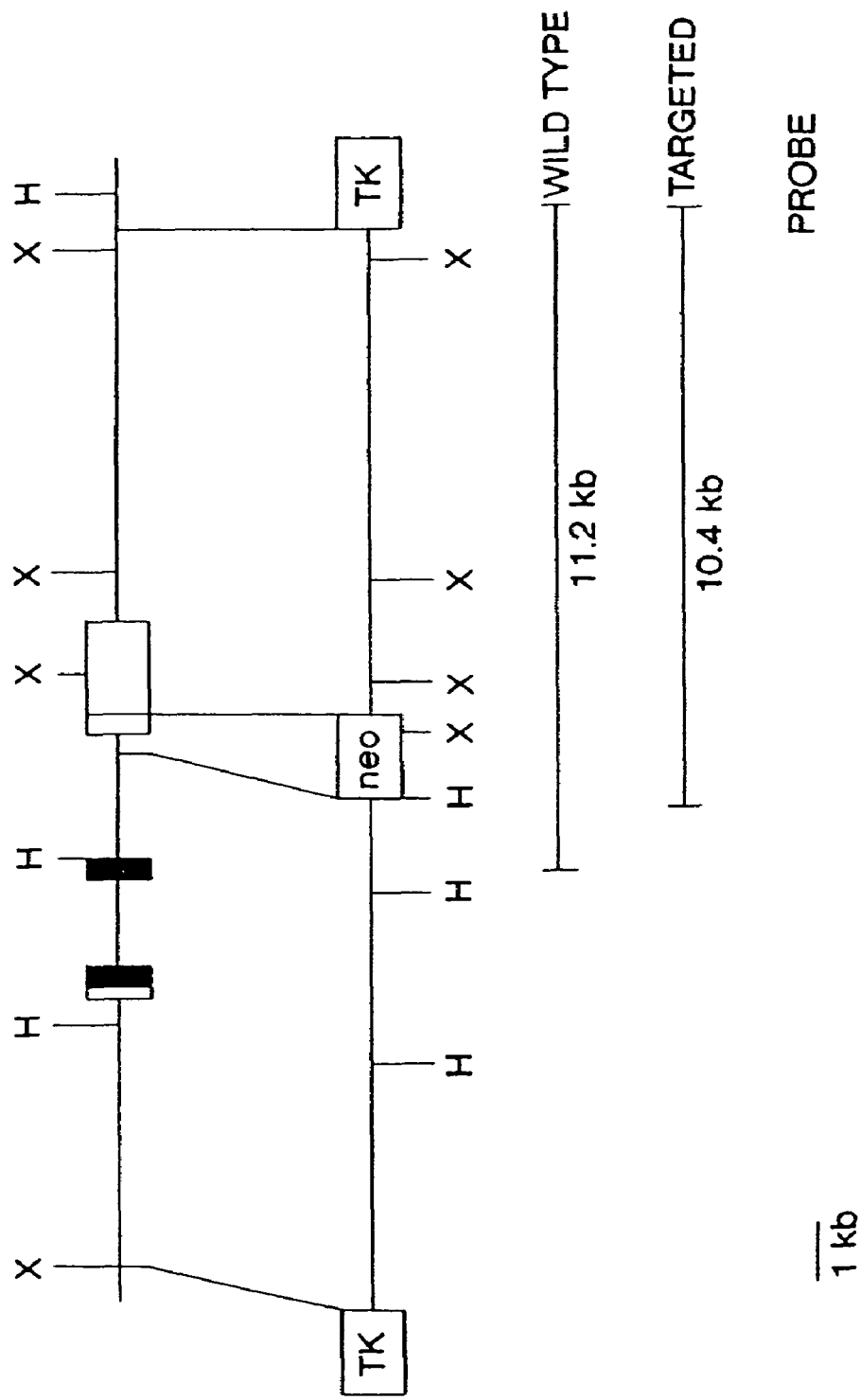
FIG. 12a shows a map of the GDF-8 locus (top line) and targeting construct (second line). The black and stippled boxes represent coding sequences for the pro-region and C-terminal region, respectively. The white boxes represent 5'-untranslated and 3'-untranslated sequences. A probe derived from the region downstream of the 3'-homology fragment and upstream of the most distal HindIII site shown hybridizes to an 11.2 kilobase (kb) HindIII fragment in the GDF-8 gene and a 10.4 kb fragment in an homologously targeted gene. Abbreviations: H, HindIII; X, Xba I.

The GDF-8, we disrupted the GDF-8 gene was disrupted by homologous targeting in embryonic stem cells. To ensure that the resulting mice would be null for GDF-8 function, the entire mature C-terminal region was deleted and replaced by a neo cassette (FIG. 12a). A murine 129 SV/J genomic library was prepared in lambda FIX II according to the instructions provided by Stratagene (La Jolla, Calif.). The structure of the GDF-8 gene was deduced from restriction mapping and partial sequencing of phage clones isolated from this library. R1 ES cells were transfected with the targeting construct, selected with gancyclovir (2 µM) and G418 (250 µg/ml), and analyzed by Southern blot analysis. Homologously targeted clones were injected into C57BL/6 blastocysts and transferred into pseudopregnant females. Germline transmission of the targeted allele was obtained in a total of 9 male chimeras from 5 independently derived ES clones. Genomic Southern blots were hybridized at 42° C. as described above and washed in 0.2×SSC, 0.1% SDS at 42° C.

For whole leg analysis, legs of 14 week old mice were skinned, treated with 0.2 M EDTA in PBS at 4° C. for 4 weeks followed by 0.5 M sucrose in PBS at 4° C. For fiber number and size analysis, samples were directly mounted and frozen in isopentane as described (Brumback and Leech, Color Atlas of Muscle Histochemistry, pages 9-33, PSG Publishing Company, Littleton, Mass., 1984). Ten to 30 µm sections were prepared using a cryostat and stained with hematoxylin and eosin. Muscle fiber numbers were determined from sections taken from the widest part of the tibialis cranialis muscle. Muscle fiber sizes were measured from photographs of sections of tibialis cranialis and gastrocnemius muscles. Fiber type analysis was carried out using the myosin ATPase assay after pretreatment at pH 4.35 as described (Cumming et al., Color Atlas of Muscle Pathology, pp. 184-185, 1994) and by immunohistochemistry using an antibody directed against type I myosin (MY32, Sigma) and the Vectastain method (Vector Labs); in the immunohistochemical experiments, no staining was seen when the primary antibodies were left out. Carcasses were prepared from shaved mice by removing the all of the internal organs and associated fat and connective tissue. Fat content of carcasses from 4 month old males was determined as described (Leshner et al., Physiol. Behavior, 9:281, 1972).

For protein and DNA analysis, tissue was homogenized in 150 mM NaCl, 100 mM EDTA. Protein concentrations were determined using the Biorad protein assay. DNA was isolated by adding SDS to 1%, treating with 1 mg/ml proteinase K overnight at 55° C., extracting 3 times with phenol and twice with chloroform, and precipitating with ammonium acetate and EtOH. DNA was digested with 2 mg/ml RNase for 1 hour at 37° C., and following proteinase K digestion and phenol and chloroform extractions, the DNA was precipitated twice with ammonium acetate and EtOH.

Figure 12B:
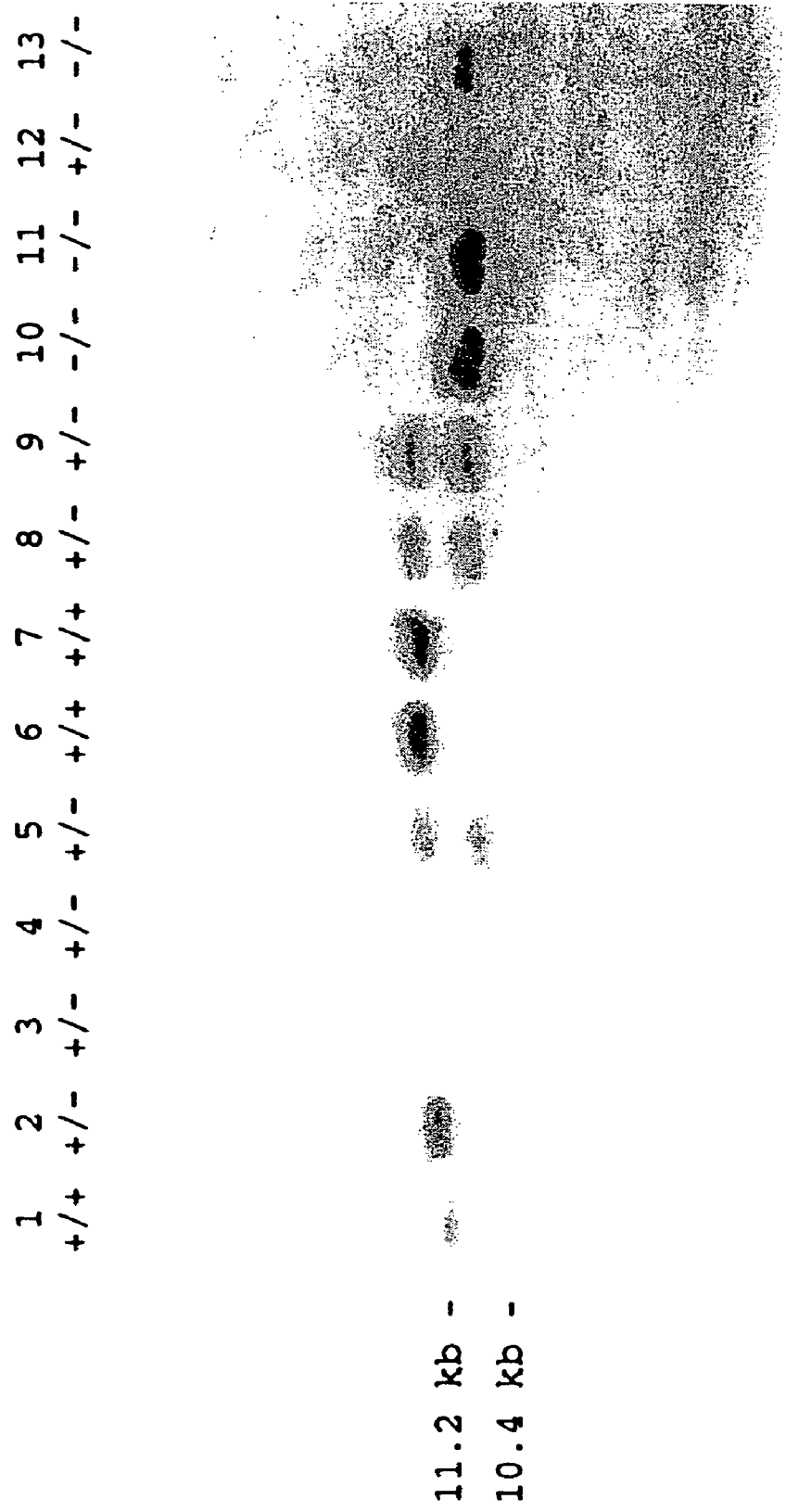
FIG. 12b shows a Southern blot analysis of offspring derived from a mating of heterozygous mutant mice. The lanes are as follows: DNA prepared from wild type 129 SV/J mice (lane 1), targeted embryonic stem cells (lane 2), F1 heterozygous mice (lanes 3 and 4), and offspring derived from a mating of these mice (lanes 5-13).

Homologous targeting of the GDF-8 gene was seen in 13/131 gancyclovir/G418 doubly-resistant ES cell clones. Following injection of these targeted clones into blastocysts, we obtained chimeras from 5 independently derived ES clones that produced heterozygous pups when crossed to C57BL/6 females (FIG. 12b). Genotypic analysis of 678 offspring derived from crosses of F1 heterozygotes showed 170+/+(25%), 380+/−(56%), and 128−/− (19%). Although the ratio of genotypes was close to the expected ratio of 1:2:1, the smaller than expected number of homozygous mutants appeared to be statistically significant (p<0.001).

Homozygous mutants were viable and fertile when crossed to C57BL/6 mice and to each other. Homozygous mutant animals, however, were approximately 30% larger than their heterozygous and wild type littermates (McPherron et al., Nature 387:83-90, 1997, which is incorporated herein by reference; see Table 1). The difference between mutant and wild type body weights appeared to be relatively constant irrespective of age and sex in adult animals. Adult mutants also displayed an abnormal body shape, with pronounced shoulders and hips. When the skin was removed from animals that had been sacrificed, it was apparent that the muscles of the mutants were much larger than those of wild type animals. The increase in skeletal muscle mass appeared to be widespread throughout the body. Individual muscles isolated from homozygous mutant animals weighed approximately 2-3 times more than those isolated from wild type littermates (McPherron et al., supra, 1997; see Table 2). Although the magnitude of the weight increase appeared to roughly correlate with the level of GDF-8 expression in the muscles examined. To determine whether the increased muscle mass could account for the entire difference in total body weights between wild type and mutant animals or whether many tissues were generally larger in the mutants, we compared the total body weights to carcass weights. The difference in carcass weights between wild type and mutant animals was comparable to the difference in total body weights (McPherron et al., supra, 1997; see Table 3). Moreover, because the fat content of mutant and wild type animals was similar, these data are consistent with all of the total body weight difference resulting from an increase in skeletal muscle mass, although we have not formally ruled out the possibility that differences in bone mass might also contribute to the differences in total body mass. Mice having a heterozygous knockout had a phenotype of intermediate muscle mass, between the wild-type and the homozygous knockout.

Figure 13A:
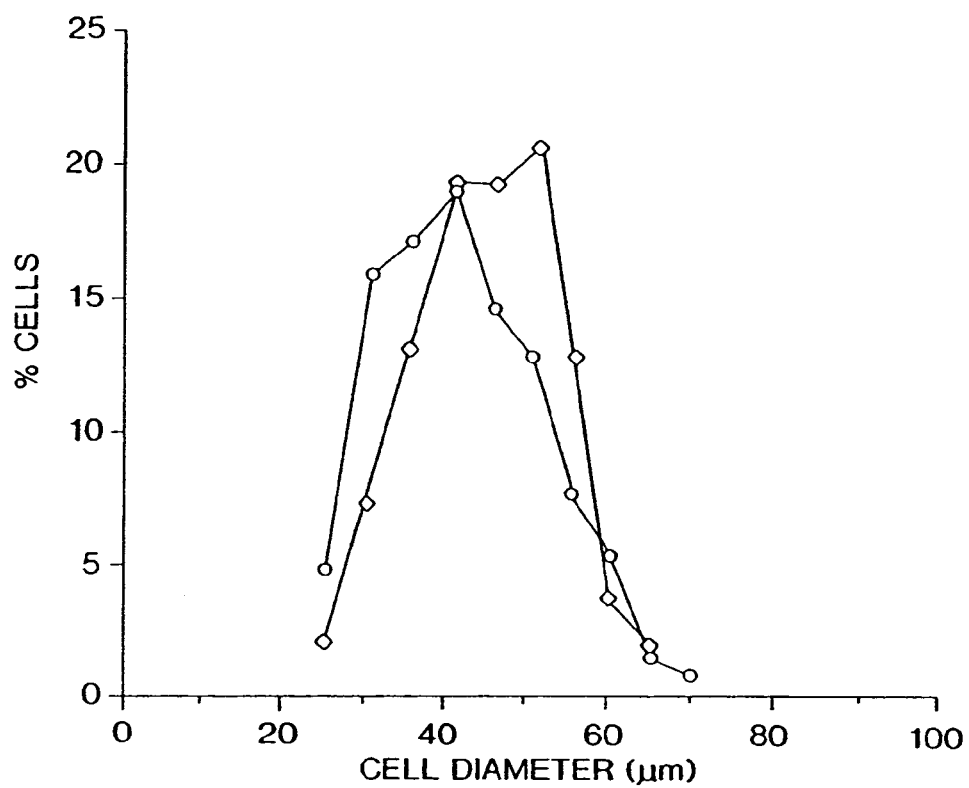
FIGS. 13a and 13b show the muscle fiber size distribution in mutant and wild type littermates. Smallest cross-sectional fiber widths were measured for (a) wild type (n=1761) and mutant (n=1052) tibialis cranialis or (b) wild type (n=900) and mutant (n=900) gastrocnemius muscles, and fiber sizes were plotted as a percent of total fiber number. Standard deviations were 9 and 10 Tm, respectively, for wild type and mutant tibialis cranial is and 11 and 9 Tm, respectively, for wild type and mutant gastrocnemius muscles. Legend: o-o, wild type; [-[, mutant.
Figure 13B:
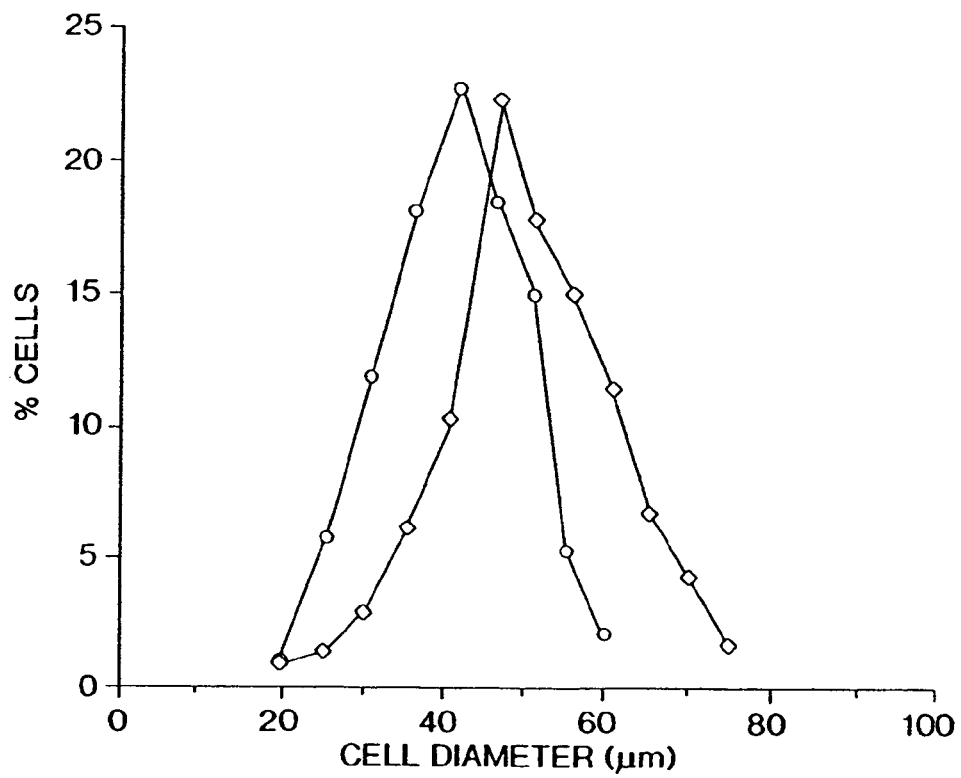

To determine whether the increase in skeletal muscle mass resulted from hyperplasia or from hypertrophy, histologic analysis of several different muscle groups was performed. The mutant muscle appeared grossly normal. No excess connective tissue or fat was seen nor were there any obvious signs of degeneration, such as widely varying fiber sizes (see below) or centrally placed nuclei. Quantitation of the number of muscle fibers showed that at the widest portion of the tibialis cranialis muscle, the total cell number was 86% higher in mutant animals compared to wild type littermates (mutant=5470+/−121 (n=3), wild type=2936+/−288 (n=3); p<0.01). Consistent with this result was the finding that the amount of DNA extracted from mutant muscle was roughly 50% higher than from wild type muscle (mutant=350 µg (n=4), wild type=233 µg (n=3) from pooled gastrocnemius, plantaris, triceps brachii, tibialis cranialis, and pectoralis muscles; p=0.05). Hence, a large part of the increase in skeletal muscle mass resulted from muscle cell hyperplasia. However, muscle fiber hypertrophy also appeared to contribute to the overall increase in muscle mass. As shown in FIG. 13, the mean fiber diameter of the tibialis cranialis muscle and gastrocnemius muscle was 7% and 22% larger, respectively, in mutant animals compared to wild type littermates, suggesting that the cross-sectional area of the fibers was increased by approximately 14% and 49%, respectively. Notably, although the mean fiber diameter was larger in the mutants, the standard deviation in fiber sizes was similar between mutant and wild type muscle, consistent with the absence of muscle degeneration in mutant animals. The increase in fiber size was also consistent with the finding that the protein to DNA ratio (w/w) was slightly increased in mutant compared to wild type muscle (mutant=871+/−111 (n=4), wild type=624+/−85 (n=3); p<0.05).

Finally, fiber type analysis of various muscles was carried out to determine whether the number of both type I (slow) and type II (fast) fibers was increased in the mutant animals. In most of the muscles examined, including the tibialis cranialis muscle, the vast majority of muscle fibers were type II in both mutant and wild type animals. Hence, based on the cell counts discussed above, the absolute number of type II fibers were increased in the tibialis cranialis muscle. In the soleus muscle, where the number of type I fibers was sufficiently high that we could attempt to quantitate the ratio of fiber types could be quantitated, the percent of type I fibers was decreased by approximately 33% in mutant compared to wild type muscle (wild type=39.2+/−8.1 (n=3), mutant=26.4+/−9.3 (n=4)); however, the variability in this ratio for both wild type and mutant animals was too high to support any firm conclusions regarding the relative number of fiber types.

EXAMPLE 9

Isolation of Rat, Chicken and Fish GDF-8

In order to isolate rat and chicken GDF-8 cDNA clones, skeletal muscle cDNA libraries prepared from these species were obtained from Stratagene and screened with a murine GDF-8 probe. Library screening was carried out as described previously (Lee, Mol. Endocrinol., 4:1034-1040) except that final washes were carried out in 2×SSC at 65° C. Partial sequence analysis of hybridizing clones revealed the presence of open reading frames highly related to murine and human GDF-8. Partial sequences of rat and chicken GDF-8 are shown in FIGS. 2c and 2d, respectively, and an alignment of the predicated rat and chicken GDF-8 amino acid sequences with those of murine and human GDF-8 are shown in FIG. 3b. All four sequences contain an RSRR (SEQ ID NO:52) sequence that is likely to represent the proteolytic processing site. Following this RSRR (SEQ ID NO:53) sequence, the sequences contain a C-terminal region that is 100% conserved among all four species. The absolute conservation of the C-terminal region between species as evolutionarily far apart as humans and chickens suggests that this region will be highly conserved in many other species as well.

Sequences for finfish GDF-8 were obtained by preparing libraries from zebrafish and salmon polyA RNA (see McPherron and Lee, Proc. Natl. Acad. Sci., USA, 94:12457, 1997, which is incorporated herein by reference). Zebrafish GDF-8 is deposited in GenBank as accession no. AF019626. GDF-8 in salmon appears to have at least 2 alleles, since there were several clones having the sequence of allele 1 and several having the sequence of allele 2. The nucleic acid sequences and deduced amino acid sequences for zebrafish, allele 1 of salmon, and allele 2 of salmon, are shown in FIGS. 2e, 2f, and 2g, respectively. FIGS. 3c and 3d show an amino acid sequence alignment between murine, zebrafish, and salmon (alleles 1 and 2) GDF-8. The C-terminal sequences are highly conserved. Cleavage of the precursor at the downstream site would generate a mature biologically active C-terminal fragment of 109 amino acids for murine GDF-8. Comparing the fish sequences with murine in the C-terminal fragment, there are only 14 amino acid differences, which is approximately 88% identity.

EXAMPLE 10

Gene Transfer and Retention in Fish

The most common method for producing transgenic fish used to date is microinjection. To transfer DNA into the germ line of salmonids, the transgene constrct is microinjected into the cytoplasm of fertilized eggs in early development. Linear DNA is retained more effectively than the circular DNA in early development (Iyengar et al., Mol. Mar. Biol. Biotech., 4:248-254, 1995). The frequency of germline transformation usually is very low for circular DNA. Therefore, linear DNA, from which all the vector sequences are removed, is prefered. According to the availability of fish eggs, the gene is transferred into cutthrout trout (or coho salmon) eggs, by way of example only, using an established microinjection procedure.

Briefly, fertilized eggs which have been developmently arrested and retain soft chorions are microinjected with 2 nL of DNA solution (containing $10^7$ copies of the gene construct) into the perimycropylar region, through the chorion and vitelline memberane into the egg cytoplasm. By this method, DNA is introduced into the vicinity of both the male and female pronuclei, and integration into host chromosomes occurs on average during the first through third cleavage divisions. More than 80 eggs (and up to 1000 eggs) are microinjected. Injected eggs are allowed to develop into fry over approximately 4-6 months. With other constrcts that do not have an effect on viability, a typical survival rate would be approximately 70% at this stage with 1-2% transgenic salmonids.

One way to identify the transgenic individuals, fish transfected with the construct are bled to obtain plasma. The plasma samples are analyzed by PCR using construct-specific oligonucleotide primers.

Although the invention has been described with reference to the presently preferred embodiment, it should be understood that various modifications can be made without departing from the spirit of the invention. Accordingly, the invention is limited only by the following claims.

What is claimed is:

1. A substantially purified GDF-8 polypeptide from a piscine or *Xenopus* organism, wherein the polypeptide has from about 85% to 95% identity to amino acid residues 268-376 of murine GDF-8 (SEQ ID NO: 12), and wherein the polypeptide regulates muscle growth in the organism.

2. The polypeptide of claim 1, wherein the polypeptide comprises SEQ ID NO:29, SEQ ID NO:31, SEQ ID NO:33, SEQ ID NO:43, SEQ ID NO:45, SEQ ID NO:47, SEQ ID NO:49, or SEQ ID NO:51.

* * * * *